US006897045B2

(12) United States Patent
Engelhardt et al.

(10) Patent No.: US 6,897,045 B2
(45) Date of Patent: *May 24, 2005

(54) ADENO-ASSOCIATED VIRUS VECTORS

(75) Inventors: John F. Engelhardt, Iowa City, IA (US); Dongsheng Duan, Iowa City, IA (US)

(73) Assignee: University of Iowa Research Foundation, Iowa City, IA (US)

(*) Notice: Subject to any disclaimer, the term of this patent is extended or adjusted under 35 U.S.C. 154(b) by 332 days.

This patent is subject to a terminal disclaimer.

(21) Appl. No.: 10/054,665

(22) Filed: Jan. 22, 2002

(65) Prior Publication Data

US 2002/0197237 A1 Dec. 26, 2002

Related U.S. Application Data

(63) Continuation of application No. 09/276,625, filed on Mar. 25, 1999, now Pat. No. 6,436,392.
(60) Provisional application No. 60/086,166, filed on May 20, 1998.

(51) Int. Cl.$^7$ ...................... C12N 15/864; C12N 15/63; C12P 21/02
(52) U.S. Cl. .................... 435/69.6; 435/320.1; 435/455; 435/456; 435/457; 435/69.1; 435/183; 435/325; 435/349; 435/350; 435/351; 435/366; 435/363; 435/368; 435/370; 435/371; 435/372
(58) Field of Search .............................. 435/320.1, 455, 435/456, 457, 69.1, 69.6, 183, 325, 349, 350, 351, 363, 366, 368, 370, 371, 372

(56) References Cited

U.S. PATENT DOCUMENTS

| | | | |
|---|---|---|---|
| 5,604,090 A | 2/1997 | Alexander et al. ............. 435/5 |
| 5,691,176 A | 11/1997 | Lebkowski et al. | |
| 5,801,030 A | * 9/1998 | McVey et al. ............... 435/456 |
| 5,834,182 A | 11/1998 | Alexander et al. ............. 435/5 |
| 5,843,742 A | * 12/1998 | Natsoulis et al. ........... 435/465 |
| 6,083,702 A | 7/2000 | Mitchell et al. | |
| 6,156,303 A | 12/2000 | Russell et al. ............. 424/93.2 |
| 6,200,560 B1 | 3/2001 | Couto et al. | |
| 6,287,569 B1 | 9/2001 | Kipps et al. ............. 424/199.1 |
| 6,436,392 B1 | 8/2002 | Engelhardt et al. ........ 424/93.2 |
| 6,544,786 B1 | 4/2003 | Xiao et al. .................. 435/325 |
| 2002/0131956 A1 | 9/2002 | Walsh et al. ............... 424/93.2 |
| 2003/0103939 A1 | 6/2003 | Engelhardt et al. ........ 424/93.2 |

FOREIGN PATENT DOCUMENTS

| | | |
|---|---|---|
| WO | 94/13788 | 12/1992 |
| WO | 95/07351 | 9/1993 |
| WO | WO-95/15384 A1 | 6/1995 |
| WO | 98/09657 | 9/1996 |
| WO | 97/22250 | 12/1996 |
| WO | WO-98/24479 A1 | 6/1998 |
| WO | WO-00/75365 A2 | 12/2000 |
| WO | WO-01/25465 A1 | 4/2001 |
| WO | WO-01/83692 A2 | 11/2001 |
| WO | WO-03/006616 A2 | 1/2003 |

OTHER PUBLICATIONS

"PCT International Search Report from International Application No. PCT/US02/21926", (Oct. 15, 2002), 4 pages.

Bartlett, J S., et al., "Targeted adeno–associated virus vector transduction of nonpermissive cells mediated by a bispecific F(ab'gamma)2 antibody", *Nature Biotechnology*, 17, (1999), pp. 181–186.

Chu, Q, et al., "Binding and uptake of Cationic Lipid: pDNA Complexes by Polarized Airway Epithelial Cells", *Human Gene Therapy*, 10, (1999), pp. 25–36.

Coonrod, A, et al., "On the mechanism of DNA transfection: efficent gene transfer without viruses", *Gene Therapy*, 4, 1997), pp. 1313–1321.

Duan, Dongsheng, et al., "Dynamin is required for recombinant adeno–associated virus type 2 infection", *J of Virology*, vol. 73, No. 12, XP002154342, (Dec. 1999), 10371–10376).

Duan, D, et al., "Response to "Polarity Influences the Efficiency of Recombinant Adenoassociated Virus Infection in Differentiated Airway Epithelia""", *Human Gene Therapy*, 10, (1999), pp. 1553–1557.

Fasbender, Al, et al., "Complexes of adenovirus with polycationic polymers and cationic lipids increase the efficiency of gene transfer in vitro and in vivo", *The Journal of Biological Chemistry*, 272 (10), (Mar. 7, 1997), 6479–6489.

Ferrari, F K., et al., "Second–Strand Synthesis Is a Rate Limiting Step for Efficient Transduction by Recombinant Adeno–Associated Virus Vectors", *Journal of Virology*, 70 (5), (1996), pp. 3227–3234.

Fisher, K J., et al., "Transduction with Recombinant Adeno–Associated Virus for Gene Therapy Is Limited by Leading–Strand Synthesis", *Journal of Virology*, 70 (1), (1996), pp. 520–532.

Gabizon, Alberto, "Long–circulating liposomes for drug delivery in cancer therapy: a review of biodistribution studies in tumor–bearing animals", *Advanced Drug Delivery Reviews*, (1997), 337–344.

(Continued)

*Primary Examiner*—David Guzo
(74) *Attorney, Agent, or Firm*—Schwegman, Lundberg, Woessner & Kluth, P.A.

(57) ABSTRACT

The invention provides an isolated and purified DNA molecule comprising at least one DNA segment, a biologically active subunit or variant thereof, of a circular intermediate of adeno-associated virus, which DNA segment confers increased episomal stability, persistence or abundance of the isolated DNA molecule in a host cell. The invention also provides a composition comprising at least two adeno-associated virus vectors.

21 Claims, 45 Drawing Sheets

OTHER PUBLICATIONS

Gottlieb, T A., et al., "Actin Microfilaments Play a Critical Role in Endocytosis at the Apical but not the Basolateral Surface of Polarized Epithelial Cells", *The Journal of Cell Biology*, 120 (3), (1993),pp. 695–710.

Kaplan, Johanne M., et al., "Potentiation of gene transfer to the mouse lung by complexes of adenvirus vector and polycations improves therapeutic potential", *Human Gene Therapy*, vol. 9, No. 10, XP000972242, (Jul. 1, 1998), 1469–1479.

Lebkowski, J., "Adeno–Associated Virus: a Vector System for Efficient Introduction and Integration of DNA into a Variety of Mammalian Cell Types", *Molecular and Cellular Biology*, vol. 8, No. 10,(Oct. 1988),3988–3996.

Liang, E., et al., "Oligonucleotide delivery: a cellular prospective", *Pharmazie*, vol. 54, No. 8, XP000965598, (Aug. 1999),559–566.

Mah, C, et al., "Adeno–Associated Virus Type 2–Mediated Gene Transfer: Role of Epidermal Growth Factor Receptor Protein Tyrosine Kinase in Transgene Expression", *Journal of Virology*, 72 (12), (1998),pp. 9835–9843.

Pickles, R J., et al., "Limited Entry of Adenovirus Vectors into Well–Differentiated Airway Epithelium Is Responsible for Inefficient Gene Transfer", *Journal of Virology*, 72 (7), (1998),pp. 6014–6023.

Russell, D W., et al., "DNA synthesis and topoisomerase inhibitors increase transduction by adeno–associated virus vectors", *PNAS*, 92, (1995),pp. 5719–5723.

Sanlioglu, S , et al., "Cellular redox state alters recombinant adeno–associated virus transduction through tyrosine phosphatase pathways", *Gene Therapy*, 6, (1999),pp. 1427–1437.

Teramoto, S., et al., "Factors influencing adeno–associated virus–mediated gene transfer to human cystic fibrosis airway epithelial cells: comparison with adenovirus vectors", *J. ofVirology*, vol. 72, No. 11, XP002154339, (Nov. 1998), 8904–8912.

Vihinen–Ranta, M, et al., "Intracellular Route of Canine Parvovirus Entry", *Journal of Virology*, 72 (1), (1998),pp. 802–806.

Walters, R W., et al., "Basolateral Localization of Fiber Receptors Limits Adenovirus Infection from the Apical Surface of Airway Epithelia", *The Journal of Biological Chemistry*, 274 (15), (1999),pp. 10219–10226.

Wickham, T J., et al., "Adenovirus targeted to heparan–containing receptors increases its gene delivery efficiency to multiple cell types", *Nature Biotechnology*, 14, (1996),pp. 1570–1573.

Wickham, T J., et al., "Targeted Adenovirus Gene Transfer to Endothelial and Smooth Muscle Cells by Using Bispecific Antibodies", *Journal of Virology*, 70 (10), (1996),pp. 6831–6838.

Xiao, W, et al., "Adeno–Associated Virus as a Vector for Liver–Directed Gene Threapy", *Journal of Virology*, 72 (12), (1998),pp. 10222–10226.

Yang, Jusan , et al., "Concatamerization of adeno–associated virus circular genomes occurs tghroug intermolecular recombination", *J. of Virology*, 73 (11), (Nov. 1999),pp. 9468–9477.

Zabner, J , et al., "Adenovirus–Mediated Gene Transfer to Ciliated Airway Epithelia Requires Prolonged Incubation Time", *Journal of Virology*, 70 (10), (1996),pp. 6994–7003.

Zabner, J , et al., "Adenovirus–mediated generation of cAMP–stimulated Cl–transport in cystic fibrosis airway epithelia in vitro: effect of promoter and administration method", *Gene Therapy*, 3, (1996),pp. 458–465.

Afione, S.A., et al., "In Vivo Model of Adeno–Associated Virus Vector Persistence and Rescue", *Journal of Virology*, 70 (5), pp. 3235–3241, (May 1996).

Ali, R.R., et al., "Gene transfer into the mouse retina mediated by an adeno–associated viral vector", *Human Molecular Genetics*, 5 (5), pp. 591–594, (1996).

Bennett, J., et al., "Real–Time, Noninvasive In Vivo Assessment of Adeno–Associated Virus–Mediated Retinal Transduction", *Investigative Ophthalmology & Visual Science*, 38 (13), pp. 2857–2863, (Dec. 1997).

Berns, K.I., "Parvovirus Replication", *Microbiological Reviews*, 54 (3), pp. 316–329, (Sep. 1990).

Berns, K.I., et al., "Biology of Adeno–associated Virus", In: *Current Topics in Microbiology and Immunology*, 218, Springer–Verlag, Berlin: R.W. Compans, et al., (Eds.), pp. 1–23, (1996).

Clark, K.R., et al., "Recombinant Adeno–Associated Viral Vectors Mediate Long–Term Transgene Expression in Muscle", *Human Gene Therapy*, 8, pp. 659–669, (Apr. 10, 1997).

Conrad, C.K., et al.,"Safety of single–dose administration of an adeno–associated virus (AAV)–CFTR vector in the primate lung", *Gene Therapy*, 3, pp. 658–668, (1996).

Duan, D., et al., "Circular intermediates of recombinant adeno–associated virus having defined structural characteristics responsible for long–term episomal persistence in muscle tissue", *J. of Virology*, 72 (11), , pp. 8568–8577, (Nov. 1998).

Duan, D., et al., "Formation of adeno–associated virus circular genomes is differentially regulated by adenovirus E4 ORF6 and E2a gene expression", *J. Virology*, 73 (1), pp. 161–169, (Jan. 1999).

Duan, D., et al., "Polarity Influences the Efficiency of Recombinant Adenoassociated Virus Infection in Differentiated Airway Epithelia", *Human Gene Therapy*, 9, pp. 2761–2776, (Dec. 10, 1998).

Duan, D., et al., "Structural Analysis of adeno–associated virus transduction circular intermediates", *Virology*, 261 (1),, pp. 8–14, (Aug. 1999).

Duan, D., et al., "Structural and functional heterogeneity of intregrated recombinant AAV genomes", *Virus Research*, 48 (1), , pp. 41–56, (Jan. 1997).

Fisher, K., et al., "Recombinant adeno–associated virus for muscle directed gene therapy", *Nature Medicine*, 3 (3), , pp. 306–312, (Mar. 1997).

Fisher–Adams, G., et al., "Integration of Adeno–Associated Virus Vectors in CD34+ Human Hematopoietic Progenitor Cells After Transduction", *Blood*, 88 (2), pp. 492–504, (Jul. 15, 1996).

Flotte, T.R., et al., "Adeno–Associated Virus Vector Gene Expression Occurs in Nondividing Cells in the Absence of Vector DNA Integration", *American Journal of Respiratory Cell and Molecular Biology*, 11, pp. 517–521, (1994).

Giraud, C., et al., "Recombinant junctions formed by site–specific integration of adeno–associated virus into an episome", *J. of Virology*, 69 (11), , pp. 6917–6924, (Nov. 1995).

Halbert, C.L., et al., "Transduction by Adeno–Associated Virus Vectors in the Rabbit Airway: Efficiency, Persistence, and Readministration", *Journal of Virology*, 71 (8), pp. 5932–5941, (Aug. 1997).

Herzog, R.W., et al., "Stable gene transfer and expressionof human blood coagulation factor IX after intramuscular injection of recombinant adeno–associated virus", *PNAS*, 94, pp. 5804–5809, (May 1997).

Kaplitt, M.G., et al., "Long–term gene expression and phenotypic correction using adeno–associated virus vectors in the mammalian brain", *Nature Genetics*, 8, pp. 148–154, (Oct. 1994).

Kearns, W.G., et al., "Recombinant adeno–assicated virus (AAV–CFTR) vectors do not integrate in a site–specific fachion in an immortalized epithelial cell line", *Gene Therapy*, 3, pp. 748–755, (1996).

Kessler, P.D., et al., "Gene delivery to skeletal muscle results in sustained expression and systemic delivery of a therapeutic protein", *PNAS*, 93, pp. 14082–14087, (Nov. 1996).

Kotin, R.M., et al., "Characterization of a preferred site on human chromosome 19q for integration of adeno–associated virus DNA by non–homologous recombination", *The EMBO Journal*, 11 (13), pp. 5071–5078, (1992).

Linden, R.M., et al., "Site–specific integration by adeno–associated virus", *PNAS*, 93, pp. 11288–11294, (Oct. 1994).

Linden, R.M., et al., "The recombinant signals for adeno–associated virus site–specific integration", *PNAS*, 93, pp. 7966–7972, (Jul. 1996).

McLaughlin, S.K., et al., "Adeno–associated virus general transduction vectors: analysis of proviral structures", *Journal of Virology*, 62 (6), pp. 1963–1973, (Jun. 1988).

Muzyczka, N., "Use of Adeno–Associated Virus as a General Transduction Vector for Mammalian Cells", In: *Current Topics in Microbiology and Immunology*, 158, Springer–Verlag, Berlin: R.W. Compans, et al., (Eds.), pp. 97–129, (1992).

Ponnazhagan, S., et al., "Lack of Site–Specific Integration of the Recombinant Adeno–Associated Virus 2 Genomes in Human Cells", *Human Gene Therapy*, 8, pp. 275–284, (Feb. 10, 1997).

Puttaraju, M., et al., "Spliceosome–mediated RNA trans–splicing as a tool for gene therapy", *Nature Biotechnology*, 17 (3), pp. 246–252, (Mar. 1999).

Qing, K., et al., "Adeno–Associated Virus Type 2–Mediated Gene Transfer: Correlation of Tyrosine Phosphorylation of the Cellular Single–Stranded D Sequence–Binding Protein with Transgene Expression in Human Cells In Vitro and Murine Tissues In Vivo", *Journal of Virology*, 72 (2), pp. 1593–1599, (Feb. 1998).

Qing, K., et al., "Human fibroblast growth factor receptor 1 is a co–receptor for infection by adeno–associated virus 2", *Nature Medicine*, 5 (1), pp. 71–77, (Jan. 1999).

Qing, K., et al., "Role of tyrosine phosphorylation of a cellular protein in adeno–associated virus 2–mediated transgene expression", *PNAS*, 94, pp. 10879–10884, (Sep. 1997).

Ramage, A.D., et al., "Improved EBV–based shuttle vector system: dicistronic mRNA couples the synthesis of the epstein–Barr nuclear antigen–1 protein toneomycin resistance", *Gene*, 197 (102), pp. 83–89, (1997).

Samulski, R.J., "Adeno–assicated virus: integration at a specific chromosomal locus", *Current Opinion in Genetics & Development*, 3 (1), pp. 74–80, (1993).

Samulski, R.J., et al., "A Recombinant Plasmid from Which an Infectious Adeno–Associated Virus Genome Can Be Excised In Vitro and Its Use To Study Viral Replication", *Journal of Virology*, 61 (10), pp. 3096–3101, (Oct. 1987).

Samulski, R.J., et al., "Helper–Free Stocks of Recombinant Adeno–Associated Viruses: Normal Integration Does Not Require Viral Gene Expression", *Journal of Virology*, 63 (9), pp. 3822–3828, (Sep. 1989).

Snyder, R.O., et al., "Persistent and therapeutic concentrations of human factor IX in mice after hepatic gene transfer of recombinant AAV vectors", *Nature Genetics*, 16, pp. 270–276, (Jul. 1997).

Summerford, C. et al., "alphaVbeta5 integrin: a co–receptor for adeno–associated virus type 2 infection", *Nature Medicine*, 5 (1), pp. 78–82, (Jan. 1999).

Summerford, C., et al., "Membrane–Associated Heparan Sulfate Proteoglycan Is a Receptor for Adeno–associated Virus Type 2 Virions", *Journal of Virology*, 72 (2), pp. 1438–1445, (Feb. 1998).

Walsh, C.E., et al., "Phenotypic Correction of Fanconi Anemia in Human Hematopoietic Cells with a Recombinant Adeno–associated Virus Vector", *The Journal of Clinical Investigation*, 94 (4), pp. 1440–1448, (Oct. 1994).

Westfall, T.D., et al., "The ecto–ATPase inhibitor ARL 67156 enhances parasympathetic neurotransmission in the guinea–pig urinary bladder", *European Journal of Pharmacology*, 329, pp. 169–173, (1997).

Wu, P., et al., "Adeno–Associated Virus Vector–Mediated Transgene Integration into Neurons and Other Nondividing Cell Targets", *Journal of Virology*, 72 (7), pp. 5919–5926, (Jul. 1998).

Xiao, X., et al., "Efficient long–term gene transfer into muscle tissue of immunocomponent mice by adeno–associated virus vector", *J. of Virology*, 70 (11), pp. 8098–8108, (Nov. 1996).

* cited by examiner

```
5 <-->3
        10         20         30         40         50         60         70
ITR  CGGGGGTCGT TGGGCGGTCA GCCAGGCGGG CCATTTACCG TAAGTTATGT AACGACTGCA GGCATGCAAG
p79  ---------- ---------- ----GGCGGG CCATTTACCG TAAGTTATGT ggCGACTGCA GGCATGCAAG
p80  ---------- ---------- ---------- -----TACCG TAAGTTATGT AACGACTGCA GGCATGCAAG
p81  ---------- ---------- ---------- -------CCG TAAGTTATGT ggCGACTGCA GGCATGCAAG
p86  ---------- ---------- ---------- -----TACCG TAAGTTATGT AACGACTGCA GGCATGCAAG
p87  ---------- ---------- ---------- -----TACCG TAAGTTATGT AACGACTGCA GGCATGCAAG
p88  ---------- ---------- ---------- -------CCG TAAGTTATGT AACGACTGCA GGCATGCAAG

5 <-->3
        80         90        100        110        120        130        140
ITR  CTCGAATTCA TCGGTAGATA AGTAGCATGG CGGGTTAATC ATTAACTACA AGGAACCCCT AGTGATGGAG
p79  CTCGAATTCA TCGGTAGATA AGTAGCATGG CGGGTTAATC ATTgCCTACA AgAgAACCCT AGTGATGGAG
p80  CTCGAATTCA TCGGTAGATA AGTAGCATGG CGGGTTAATC ATTAACTACA AGGAACCCCT AGTGATGGAG
p81  CTCGAATTCA TCGGTAGATA AGTAGCATGG CGGGTTAATC ATTgCCTACA AgAgAACCCT AGTGATGGA-
p86  CTCGAATTCA TCGGTAGATA AGTAGCATGG CGGGTTAATC ATTAACTACA AGGAACCCCT AGTGATGGAG
p87  CTCGAATTCA TCGGTAGATA AGTAGCATGG CGGGTTACTC ATTgCCTACA AgAgAACCCT AGTGATGAAG
p88  CTCGAATTCA TCGGTAGATA AGTAGCATGG CGGGTTAATC ATTgCCTACA AgAgAACCCT AGTGATGGAG

5 <-->3
       150        160        170        180        190        200        210
ITR  TTGGCCACTC CCTCTCTGCG CGCTCGCTCG CTCGCTGAGG CCGGGGCGACC AAAAGGTCGCC CGACGCCCGG
p79  TgGGCCACTC CCTCTCTTCG C--------- ---------- ---------- ---------- ----------
p80  TTGGCCACTC CCTCTCTGCG CGCTCGCTCG CTCGCTCAGG CCGGGCAACC AAAGGTCGCC CGACGCCC--
p81  ---------- ---------- ---------- ---------- ---------- ---------- ----------
p86  TTGGCCACTC CCTCTCTGCG CGCTCGCTCG CTCGCTGAGG CCGCCC---- ---------- ----------
p87  TTGG------ ---------- ---------- ---------- ---------- ---------- ----------
p88  TTGGCCACTC CCTCTCTGCG CGCTCGCTCG CTgG------ ---------- ---------- ----------
```

FIG. 2C

```
          220         230         240         250         260         270         280
ITR  GCTTTGCCCG GGCGGCCTCA GTGAGCGAGC GAGCGCGCAG CTGCGCGCTC GCTCGCTCAC TGAGGCCGCC
p79  ---------- ---------- ---------- ---------- ---------- ---------- ----------
P80  ---------- ---------- ---------- ---------- ---------- ---------- ----------
P81  ---------- ---------- ---------- ---------- ---------- ---------- ----------
P86  ---------- ---------- ---------- ---------- ---------- ---------- ----------
P87  ---------- ---------- ---------- ---------- ---------- ---------- ----------
P88  ---------- ---------- ---------- ---------- ---------- ---------- ----------

290         300         310         320         330         340         350
ITR  CGGGCAAAGC CCGGGCGTCG GGCGACCTTT GGTCGCGCCGG CCTCAGCGAG CGAGCGAGCG CGCAGAGAGG
p79  ---------- ---------- ---------- ---------- ---------- ---CGAGCG CGCAGAGAGG
P80  ---------- ---------- ---------- ---GCCCGG CCTCAGCGAG CGAGCGAGCG CGCAGAGAGG
P81  ---------- ---------- ---------- ---GCCCGG CCTCACCGAG CGAGCGAGCG CGCAGAGAGG
P86  ---------- ---------- ---------- ------CGG CCTCAGCGAG CGAGCGAGCG CGCAGAGAGG
P87  ---------- ---------- ---------- ---------- ---------- ---------- ----------
P88  ---------- ---------- ---------- ---GCCCGG CCTCAGCGAG CGAGCGAGCG CGCAGAGAGG 360         370         380         390         400         410         420
ITR  GAGTGGCCAA CTCCATCACT AGGGGTTCCT TGTAGTTAAT GATTAACCCG CCATGCTACT TATCTACAGC
p79  GAGTGGCCAA CTCCcTCACT AGGGGTTCCT gGcAGTTAAT GATTAACCCG CCATGCTACT TATCTACAGC
P80  GAGTGGCCAA CTCCATCACT AGGGGTTCCT TGTAGTTAAT GATTAACCCG CCATGCTACT TATCTACAGC
P81  GAGTGGCCAA CTCCATCACT AGGGGTTCCT TGTAGTTAAT GATTAACCCG CCATGCTACT TATCTACAGC
P86  GAGTGGCCAA CTCCATCACT AGGGGTTCCT TGTAGTTAAT GATTAACCCG CCATGCTACT TATCTACAGC
P87  GAcTGGCCAA CTCCATCACT AGGGGTTCCT TGTAGTTAAT GATTcACCCt CCATGCTACT TATCTACAGC
p87  ---------- ---------- ---------- -----AAT GATTAACCCG CCATGCTACT TATCTACAGC
P88  GAGTGGCCAA CTCCATCACT AGGGGTTCCT gGcAGTTAAT GATTAACCCG CCATGCTACT TATCTACAGC
```

FIG. 2D

```
           430        440        450        460        470        480        490
    ITR    TTGCATGCAT GTGAGCAAAA GGCCAGCAAA AGGCCAGGAA CCGTAAAAAG GCCGCGTTGC TGGCGTTTTT
    p79    TTGCATGCAT GTGAGCAAAA GGCCAGCAAA AGGCCAGGAA CCGTAAAAAG GCCGCGTTG- ----------
    P80    TTGCATGCAT GTGAGCAAAA GGCCAGCAAA AGGCCAGGAA CCGTAAAAAG GCCGCGTTG- ----------
    P81    TTGCATGCAT GTGAGCAAAA GGCCAGCAAA AGGCCAGGAA CCGTAAAAAG GCCGCGTTG- ----------
    P86    TTGCATGCAT GTGAGCAAAA GGCCAGCAAA AGGCCAGGAA CCGTAAAAAG GCCGCGTTG- ----------
    P87    TTGCATGCAT GTGAGCAAAA GGCCAGCAAA AGGCCAGGAA CCGTAAAAAG GCCGC----- ----------
    P88    TTGCATGCAT GTGAGCAAAA GGCCAGCAAA AGGCCAGGAA CCGTAAAAAG GCCGCGTTG- ----------

5 <-->3

500        505
    ITR    CCATAGGCTC CGCCC
    p79    ---------- -----
    P80    ---------- -----
    P81    ---------- -----
    P86    ---------- -----
    P87    ---------- -----
    P88    ---------- -----

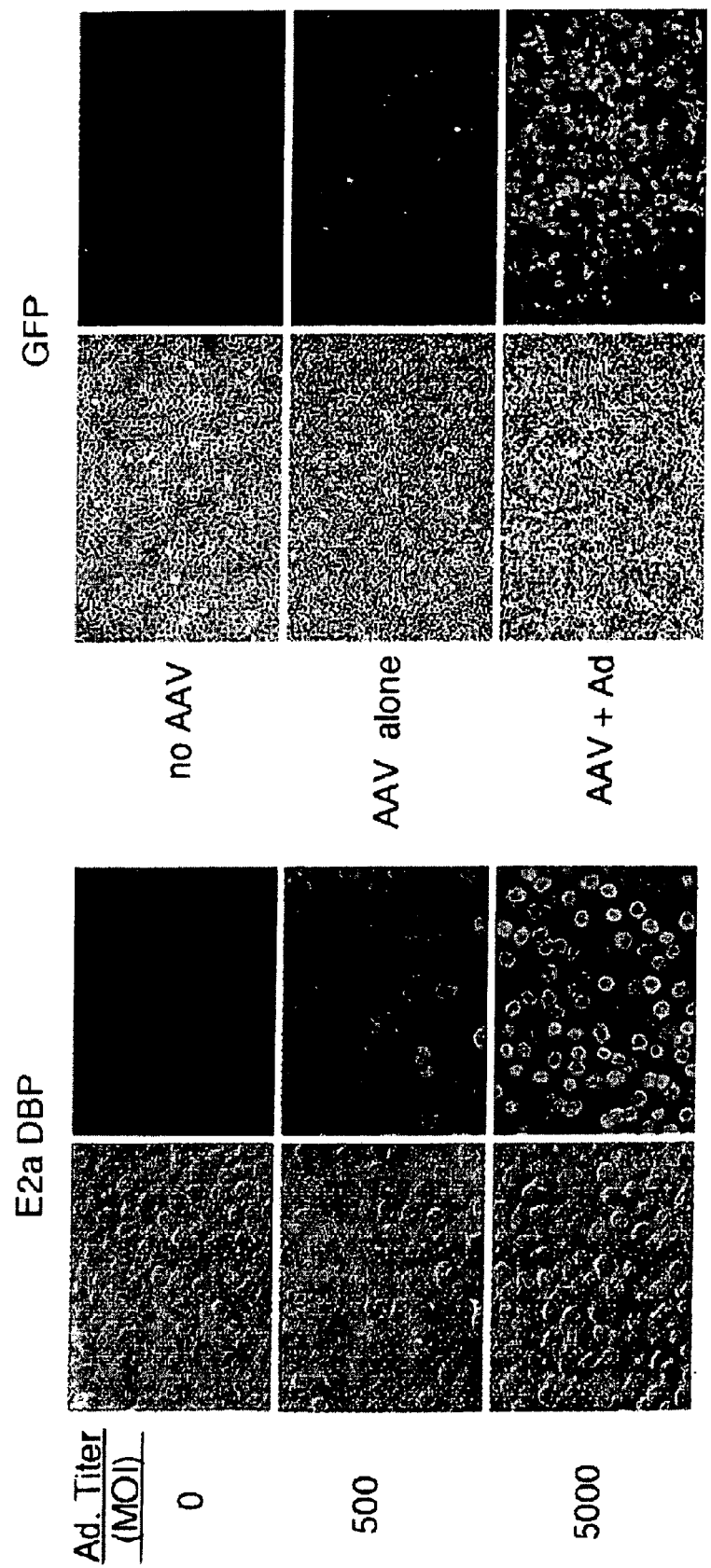

```
        10         20         30         40         50         60
GCATGCAAGC TGTAGATAAG TAGCATGGCG GGTTAATCAT TAACTACAAG GAACCCCTAG
CGTACGTTCG ACATCTATTC ATCGTACCGC CCAATTAGTA ATTGATGTTC CTTGGGGATC 70         80         90        100        110        120
TGATGGAGTT GGCCACTCCC TCTCTGCGCG CTCGCTCGCT CACTGAGGCC GGGCGGCCAA
ACTACCTCAA CCGGTGAGGG AGAGACGCGC GAGCGAGCGA GTGACTCCGG CCCGCCGGTT 130        140        150        160        170        180
AGGTCGCCCG ACGCCCGGGC TTTGCCCGGG CGGCCTCAGT GAGCGAGCGA GCGCGCAGAG
TCCAGCGGGC TGCGGGCCCG AAACGGGCCC GCCGGAGTCA CTCGCTCGCT CGCGCGTCTC 190        200        210        220        230        240
AGGGAGTGGC CAACTCCATC ACTAGGGGTT CCTTGTAGTT AATGATTAAC CCGCCATGCT
TCCCTCACCG GTTGAGGTAG TGATCCCCAA GGAACATCAA TTACTAATTG GCGGTACGA 250        260        270        280
ACTTATCTAC CGATGAATTC GAGCTTGCAT GC........
TGAATAGATG GCTACTTAAG CTCGAACGTA CG........
```

FIG. 10A

```
        10         20         30         40         50         60
GCATGCAAGC TGTAGATAAG TAGCATGGCG GGTTAATCAT TAACTACAAG GAACCCCTAG
CGTACGTTCG ACATCTATTC ATCGTACCGC CCAATTAGTA ATTGATGTTC CTTGGGGATC 70         80         90        100        110        120
TGATGGAGTT GGCCACTCCC TCTCTGCGCG CTCGCTCGCT CACTGAGGCC GGGCGCGCGC
ACTACCTCAA CCGGTGAGGG AGAGACGCGC GAGCGAGCGA GTGACTCCGG CCCGCGCGCG 130        140        150        160        170        180
TCGCTCGCTC ACTGAGGCCG GGCGACCAAA GGTCGCCCGA GCCCGGGCTT TGCCCGGGCG
AGCGAGCGAG TGACTCCGGC CCGCTGGTTT CCAGCGGGCT CGGGCCCGAA ACGGGCCCGC 190        200        210        220        230        240
GCCTCAGTGA GCGAGCGCGC GCGCAGAGAG GGAGTGGCCA ACTCCATCAC TAGGGGTTCC
CGGAGTCACT CGCTCGCGCG CGCGTCTCTC CCTCACCGGT TGAGGTAGTG ATCCCCAAGG 250        260        270        280        290        300
TTGTAGTTAA TGATTAACCC GCCATGCTAC TTATCTACCG ATGAATTCGA GCTTGCATGC
AACATCAATT ACTAATTGGG CGGTACGATG AATAGATGGC TACTTAAGCT CGAACGTACG
```

FIG. 10B

```
           10         20         30         40         50         60
    GCATGCAAGC TGTAGATAAG TAGCATGGCG GGTTAATCAT TAACTACAAG GAACCCCTAG
    CGTACGTTCG ACATCTATTC ATCGTACCGC CCAATTAGTA ATTGATGTTC CTTGGGGATC 70         80         90        100        110        120
    TGATGGAGTT GGCCACTCCC TCTCTGCGCG CTCGCTCGCT CACTGAGGCC GGGCGACCAA
    ACTACCTCAA CCGGTGAGGG AGAGACGCGC GAGCGAGCGA GTGACTCCGG CCCGCTGGTT 130        140        150        160        170        180
    AGGTCGCCCG ACGCCCGGGC TTTGGTCGCC CGGCCTCAGT GAGCGAGCGA GCGCGCAGAG
    TCCAGCGGGC TGCGGGCCCG AAACCAGCGG GCCGGAGTCA CTCGCTCGCT CGCGCGTCTC 190        200        210        220        230        240
    AGGGAGTGGC CAACTCCATC ACTAGGGGTT CCTTGTAGTT AATGATTAAC CCGCCATGCT
    TCCCTCACCG GTTGAGGTAG TGATCCCCAA GGAACATCAA TTACTAATTG GGCGGTACGA 250        260        270        280
    ACTTATCTAC CGATGAATTC GAGCTTGCAT GC........
    TGAATAGATG GCTACTTAAG CTCGAACGTA CG........
```

FIG. 10C

|       |     | 10         | 20         | 30         | 40         | 50         |     |
|-------|-----|------------|------------|------------|------------|------------|-----|
| P81   | 1   | GCATGCAAGC | TGTAGATAAG | TAGCATGGCG | GGTTAATCAT | TAACTACAAG | 50  |
| p79   | 1   | GCATGCAAGC | TGTAGATAAG | TAGCATGGCG | GGTTAATCAT | TAACTACAAG | 50  |
| p1202 | 1   | GCATGCAAGC | TGTAGATAAG | TAGCATGGCG | GGTTAATCAT | TAACTACAAG | 50  |

|       |     | 60         | 70         | 80         | 90         | 100        |     |
|-------|-----|------------|------------|------------|------------|------------|-----|
| P81   | 51  | GAACCCCTAG | TGATGGAGTT | GGCCACTCCC | TCTCTGCGCG | CTCGCTCGCT | 100 |
| p79   | 51  | GAACCCCTAG | TGATGGAGTT | GGCCACTCCC | TCTCTGCGCG | CTCGCTCGCT | 100 |
| p1202 | 51  | GAACCCCTAG | TGATGGAGTT | GGCCACTCCC | TCTCTGCGCG | CTCGCTCGCT | 100 |

|       |     | 110        | 120        | 130        | 140        | 150        |     |
|-------|-----|------------|------------|------------|------------|------------|-----|
| P81   | 101 | CACTGAGGCC | GGGCG----- | ---------- | ---------- | ---GCCAAAG | 150 |
| p79   | 101 | CACTGAGGCC | GGGCGCGCGC | TCGCTCGCTC | ACTGAGGCCG | GGCGaCcAAa | 150 |
| p1202 | 101 | CACTGAGGCC | GGGCG----- | ---------- | ---------- | ---ACCAAAG | 150 |

|       |     | 160        | 170        | 180        | 190        | 200        |     |
|-------|-----|------------|------------|------------|------------|------------|-----|
| P81   | 151 | GTCGCCCGAC | GCCCGGGCTT | TGCCCGGGCG | GCCTCAGTGA | GCGAGCGAGC | 200 |
| p79   | 151 | GgtcgCCcga | GCCCGGGCTT | TGCCCGGGCG | GCCTCAGTGA | GCGAGCGcGC | 200 |
| p1202 | 151 | GTCGCCCGAC | GCCCGGGCTT | TGgtCGccCG | GCCTCAGTGA | GCGAGCGAGC | 200 |

|       |     | 210        | 220        | 230        | 240        | 250        |     |
|-------|-----|------------|------------|------------|------------|------------|-----|
| P81   | 201 | GCGCAGAGAG | GGAGTGGCCA | ACTCCATCAC | TAGGGGTTCC | TTGTAGTTAA | 250 |
| p79   | 201 | GCGCAGAGAG | GGAGTGGCCA | ACTCCATCAC | TAGGGGTTCC | TTGTAGTTAA | 250 |
| p1202 | 201 | GCGCAGAGAG | GGAGTGGCCA | ACTCCATCAC | TAGGGGTTCC | TTGTAGTTAA | 250 |

|       |     | 260        | 270        | 280        | 290        | 300        |     |
|-------|-----|------------|------------|------------|------------|------------|-----|
| P81   | 251 | TGATTAACCC | GCCATGCTAC | TTATCTACCG | ATGAATTCGA | GCTTGCATGC | 300 |
| p79   | 251 | TGATTAACCC | GCCATGCTAC | TTATCTACCG | ATGAATTCGA | GCTTGCATGC | 300 |
| p1202 | 251 | TGATTAACCC | GCCATGCTAC | TTATCTACCG | ATGAATTCGA | GCTTGCATGC | 300 |

FIG. 11

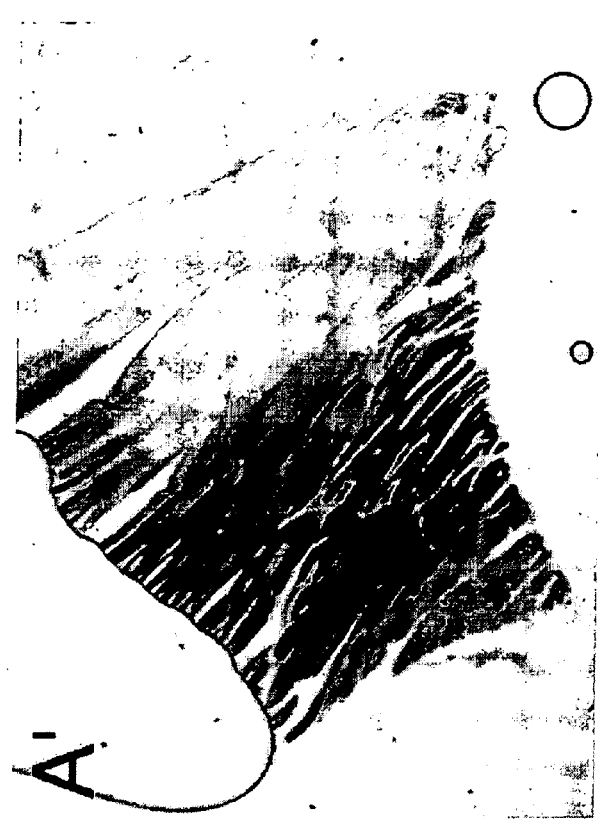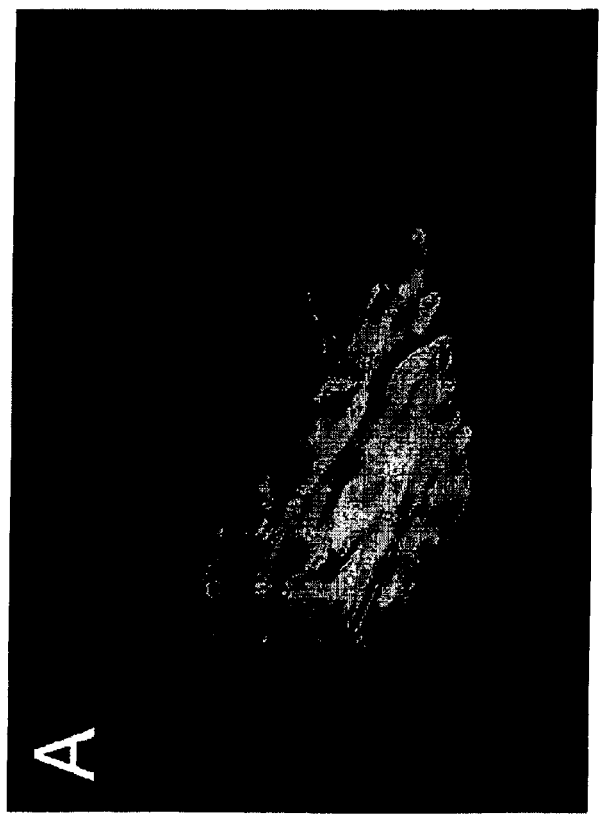
FIG. 15A

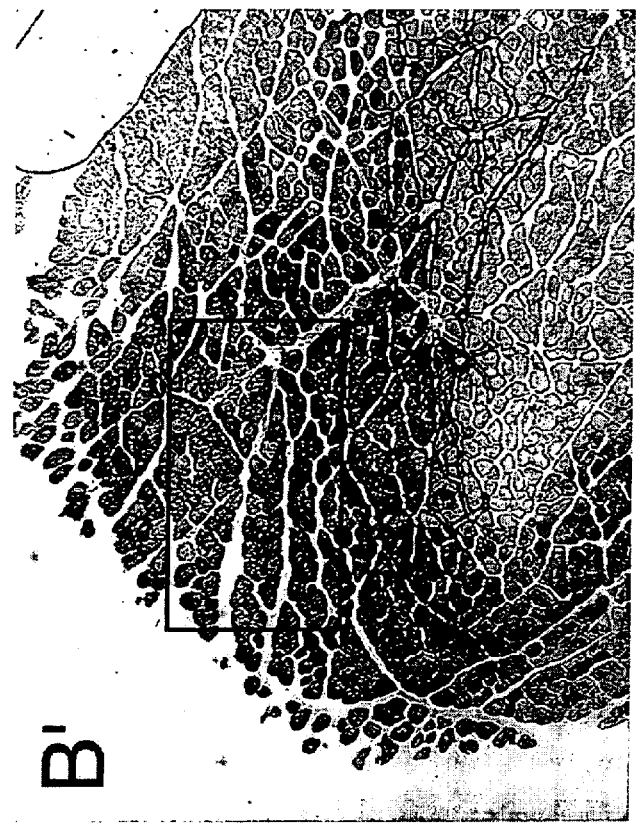
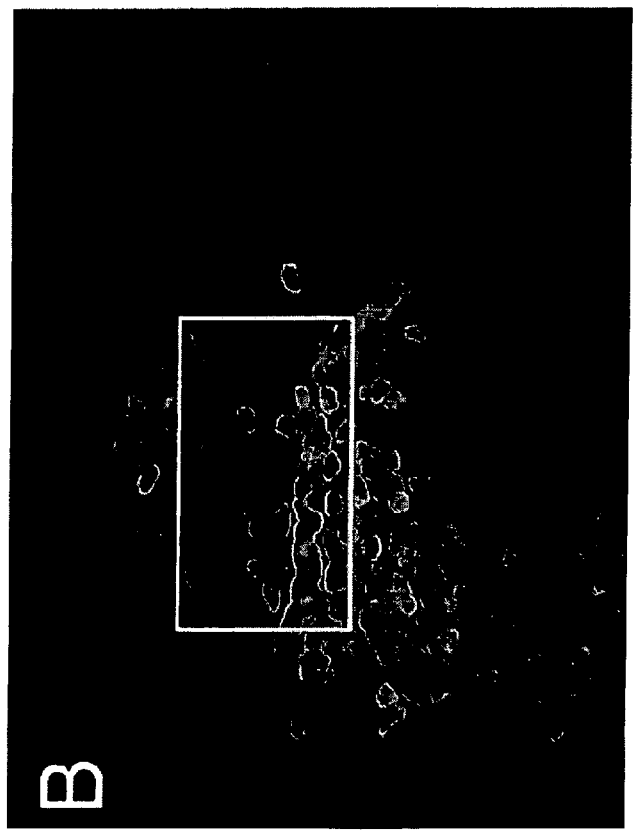
FIG. 15B

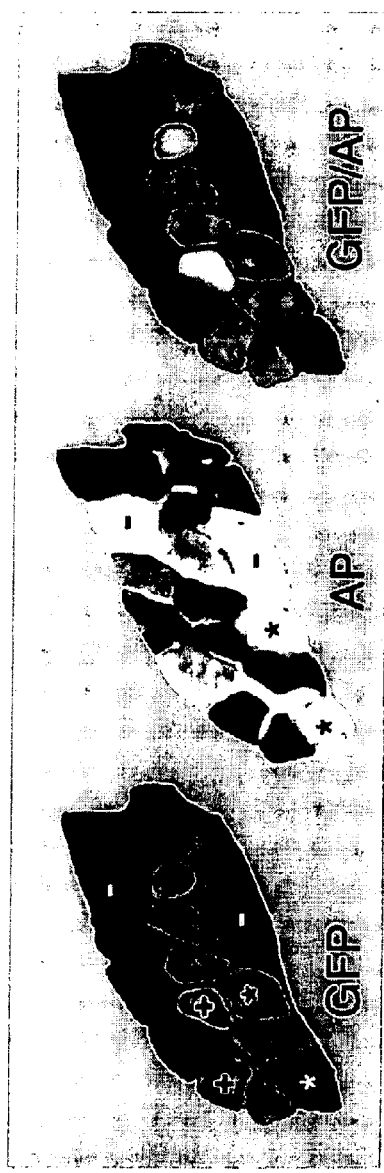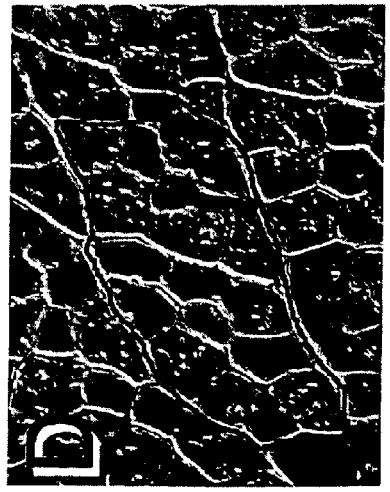
FIG. 15D

ADENO-ASSOCIATED VIRUS VECTORS

CROSS-REFERENCE TO RELATED APPLICATIONS

This application is a continuation application of U.S. application Ser. No. 09/276,625 filed Mar. 25, 1999, now U.S. Pat. No. 6,436,392, which is a continuation-in-part of, and claims priority of invention under 35 U.S.C. §119(e) from, U.S. application Ser. No. 60/086,166, filed May 20, 1998, the disclosure of which is incorporated by reference herein.

STATEMENT OF GOVERNMENT RIGHTS

This invention was made with a grant from the Government of the United States of America (Grant No. DK/HL58340 from the National Institutes of Health). The Government may have certain rights in the invention.

BACKGROUND OF THE INVENTION

Adeno-associated virus (AAV) is a non-pathogenic parvovirus with a single-stranded DNA genome of 4680 nucleotides. The genome may be of either plus or minus polarity, and codes for two groups of genes, Rep and Cap (Berns et al., 1990). Inverted terminal repeats (ITRs), characterized by palindromic sequences producing a high degree of secondary structure, are present at both ends of the viral genome. While other members of the parvovirus group replicate autonomously, AAV requires co-infection with a helper virus (i.e., adenovirus or herpes virus) for lytic phase productive replication. In the absence of a helper virus, wild-type AAV (wtAAV) establishes a latent, non-productive infection with long-term persistence by integrating into a specific locus on chromosome 19, AAVS1, of the host genome through a Rep-facilitated mechanism (Samulski, 1993; Linden et al., 1996; Kotin et al., 1992).

In contrast to wtAAV, the mechanism(s) of latent phase persistence of recombinant AAV (rAAV) is less clear. rAAV integration into the host genome is not site-specific due to deletion of the AAV Rep gene (Ponnazhagan et al., 1997). Analysis of integrated proviral structures of both wild type and recombinant AAV have demonstrated head-to-tail genomes as the predominant structural forms.

rAAV has recently been recognized as an extremely attractive vehicle for gene delivery (Muzyczka, 1992). rAAV vectors have been developed by substituting all viral open reading frames with a therapeutic minigene, while retaining the cis elements contained in two inverted terminal repeats (ITRs) (Samulski et al., 1987; Samulski et al., 1989). Following transduction, rAAV genomes can persist as episomes (Flotte et al., 1994; Afione et al., 1996; Duan et al., 1998), or alternatively can integrate randomly into the cellular genome (Berns et al., 1996; McLaughlin et al., 1988; Duan et al., 1997; Fisher-Adams et al., 1996; Kearns et al., 1996; Ponnazhagan et al., 1997). However, little is known about the mechanisms enabling rAAV vectors to persist in vivo or the identity of cellular factors which may modulate the efficiency of transduction and persistence. Although transduction of rAAV has been demonstrated in vitro in cell culture (Muzyczka, 1992) and in vivo in various organs (Kaplitt et al., 1994; Walsh et al., 1994; Conrad et al., 1996; Herzog et al., 1997; Snyder et al., 1997), the mechanisms of rAAV-mediated transduction remain unclear.

Moreover, while rAAV has been shown to be capable of stable, long-term transgene expression both in vitro and in vivo in a variety of tissues, the transduction efficiency of rAAV is markedly variable in different cell types. For example, rAAV has been reported to transduce lung epithelial cells at low levels (Halbert et al., 1997; Duan et al., 1998a), while high level, persistent transgene expression has been demonstrated in muscle, neurons and in other non-dividing cells (Kessler et al., 1996; Fisher et al., 1997; Herzog et al., 1997; Xiao et al., 1996; Kaplitt et al., 1994; Wu et al., 1998; Ali et al., 1996; Bennett et al., 1997 Westfall et al., 1997). These tissue-specific differences in rAAV mediated gene transfer may, in part, be due to variable levels of cellular factors affecting AAV infectivity (i.e., receptors and co-receptors such as heparin sulfate proteoglycan, FGFR-1, and αVβ5 integrin) (Summerford et al., 1998; Qing et al., 1999; Summerford et al., 1999) as well as the latent life cycle (i.e., nuclear trafficking of virus and/or the conversion of single stranded genomes to expressible forms) (Qing et al., 1997; Qing et al., 1998).

Muscle-mediated gene transfer represents a very promising approach for the treatment of hereditary myopathies and several other metabolic disorders. Previous studies have demonstrated remarkably efficient and persistent transgene expression to skeletal muscle in vivo with rAAV vectors. Applications in this model system include the treatment of several inherited disorders such as Factor IX deficiency in hemophilia B and epo deficiencies (Kessler et al., 1996; Herzog et al., 1997). Although the conversion of low-molecular-weight rAAV genomes to high-molecular-weight concatamers has been inferred as evidence for integration of proviral DNA in the host genome, no direct evidence exists in this regard (Xiao et al., 1996; Clark et al., 1997; Fisher et al. 1997). Also, the molecular processes and/or structures associated with episomal long-term persistence of rAAV genomes, e.g., in nondividing mature myofibers, remains unclear.

Thus, there is a need for rAAV vectors that have increased stability and/or persistence in host cells. Moreover, there is a need for vectors useful to express large open reading frames.

SUMMARY OF THE INVENTION

The present invention provides a recombinant adeno-associated virus (rAAV) vector comprising a nucleic acid segment formed by the juxtaposition of sequences in the AAV inverted terminal repeats (ITRs) which are present in a circular intermediate of AAV. The circular intermediate was isolated from rAAV-infected cells by employing a recombinant AAV "shuttle" vector. The shuttle vector comprises: a) a bacterial origin of replication; b) a marker gene or a selectable gene; c) a 5' ITR; and d) a 3' ITR. Preferably, the recombinant AAV shuttle vector contains a reporter gene, e.g., a GFP, alkaline phosphatase or β-galactosidase gene, a selectable marker gene, e.g., an ampicillin-resistance gene, a bacterial origin of replication, a 5' ITR and a 3' ITR. The vector is contacted with eukaryotic cells so as to yield transformed eukaryotic cells. Low molecular weight DNA ("Hirt DNA") from the transformed eukaryotic cells is isolated. Bacterial cells are contacted with the Hirt DNA so as to yield transformed bacterial cells. Then bacterial cells are identified which express the marker or selectable gene present in the shuttle vector and which comprise at least a portion of a circular intermediate of adeno-associated virus. Also, as described below, it was found that circularized intermediates of rAAV impart episomal persistence to linked sequences in Hela cells, fibroblasts and muscle cells. In HeLa cells, the incorporation of certain AAV sequences, e.g., ITRs, from circular intermediates into a heterologous plasmid conferred a 10-fold increase in the stability of plasmid-based vectors in HeLa cells. Unique features of these transduction intermediates included the in vivo circularization of a head-to-tail monomer as well as multimer (concatamers) episomal viral genomes with associated specific base pair alterations in the 5' viral D-sequence. The majority of circular intermediates had a consistent head-to-tail configuration consisting of monomer genomes (<3 kb) which slowly converted to large multimers of >12 kb by 80 days post-infection in muscle. Importantly, long-term transgene expression was associated with prolonged (80 day) episomal persistence of these circular intermediates. Thus, in vivo persistence of rAAV can occur through episomal circularized genomes which may represent prointegration intermediates with increased episomal stability. Moreover, as described below, co-infection with adenovirus, at high multiplicities of infection (MOI) capable of producing early adenoviral gene products, led to increases in the abundance and stability of AAV circular intermediates which correlated with an elevation in transgene expression from rAAV vectors. Thus, these results demonstrate the existence of a molecular structure involved in AAV transduction which may play a role in episomal persistence and/or integration.

Further, these results may aid in the development of non-viral or viral-based gene delivery systems having increased efficiency. For example, therapeutic or prophylactic therapies in which the present vectors are useful include blood disorders (e.g., sickle cell anemia, thalassemias, hemophilias, and Fanconi anemias), neurological disorders, such as Alzheimer's disease and Parkinson's disease, and muscle disorders involving skeletal, cardiac or smooth muscle. In particular, therapeutic genes useful in the vectors of the invention include the β-globin gene, the γ-globin gene, the cystic fibrosis transmembrane conductance receptor gene (CFTR), the Fanconi anemia complementation group, a gene encoding a ribozyme, an antisense gene, a low density lipoprotein (LDL) gene, a tyrosine hydroxylase gene (Parkinson's disease), a glucocerebrosidase gene (Gaucher's disease), an arylsulfatase A gene (metachromatic leukodystrophies) or genes encoding other polypeptides or proteins. Also within the scope of the invention is the inclusion of more than one gene in a vector of the invention, i.e., a plurality of genes may be present in an individual vector. Further, as a circular intermediate may be a concatamer, each monomer of that concatamer may comprise a different gene.

For viral-based delivery systems, helper-free virus can be prepared (see WO 95/13365) from circular intermediates or vectors of the invention. Alternatively, liposomes, plasmid or virosomes may be employed to deliver a vector of the invention to a host or host cell.

The increased persistence of circular intermediates or vectors having one or a plurality of ITRs may be due to the primary and/or secondary structure of the ITRs. The primary structure of a consensus sequence (SEQ ID NO:3) of ITRs formed by the juxtaposition and physical (phosphodiester bond) linkage of ITRs from AAV is shown in FIG. 2C. However, as described hereinbelow, each ITR sequence may be incomplete, i.e., the ITR may be a subunit or portion of the full length ITRs present in the consensus sequence. Moreover, preferably, an isolated DNA segment of the invention is not the 165 bp double DD sequence (SEQ ID NO:7) disclosed in U.S. Pat. No. 5,478,745, referred to as a "double sequence".

Moreover, the formation, persistence and/or abundance of molecules having the ITR sequences of the invention may be modulated by helper virus, e.g., adenoviral proteins and/or host cell proteins. Thus, the circular intermediates or vectors of the invention may be useful to identify and/or isolate proteins that bind to the ITR sequences present in those molecules.

Therefore, the present invention provides an isolated and purified DNA molecule comprising at least one DNA segment, a biologically active subunit or variant thereof, of a circular intermediate of adeno-associated virus, which DNA segment confers increased episomal stability, persistence or abundance of the isolated DNA molecule in a host cell. Preferably, the DNA molecule comprises at least a portion of a left (5') inverted terminal repeat (ITR) of adeno-associated virus. Also preferably, the DNA molecule comprises at least a portion of a right (3')-inverted terminal repeat of adeno-associated virus. The invention also provides a gene transfer vector, comprising: at least one first DNA segment, a biologically active subunit or variant thereof, of a circular intermediate of adeno-associated virus, which DNA segment confers increased episomal stability or persistence of the vector in a host cell; and a second DNA segment comprising a gene. Preferably, the second DNA segment encodes a therapeutically effective polypeptide. The first DNA segment comprises ITR sequences, preferably at least about 100, more preferably at least about 300, and even more preferably at least about 400, bp of adeno-associated virus sequence. A preferred vector of the invention is a plasmid.

Thus, the vector of the invention is useful in a method of delivering and/or expressing a gene in a host cell, to prepare host cells having the vector(s), and in the preparation of compositions comprising such vectors. To deliver the gene to the host cell, a recombinant adenovirus helper virus may be employed.

As described hereinbelow, the tibialis muscle of mice was co-infected with rAAV Alkaline phosphatase (Alkphos) and GFP encoding vectors. The GFP shuttle vector also encoded ampicillin resistance and a bacterial origin of replication to allow for bacterial rescue of circular intermediates in Hirt DNA from infected muscle samples. There was a time dependent increase in the abundance of rescued plasmids encoding both GFP and Alkphos that reached 33% of the total circular intermediates by 120 days post-infection. Furthermore, these large circular concatamers were capable of expressing both GFP and Alkphos encoded transgenes following transient transfection in cell lines. Thus, concatamerization of AAV genomes in vivo occurs through intermolecular recombination of independent monomer circular viral genomes. Therefore, a plurality of DNA segments, each in an individual rAAV vector, may be delivered so as to result in a single DNA molecule having a plurality of the DNA segments. For example, one rAAV vector comprises a first DNA segment comprising a 5' ITR linked to a second DNA segment comprising a promoter operably linked to a third DNA segment comprising a first open reading frame linked to a fourth DNA segment comprising a 3' ITR. A second rAAV vector comprises a first DNA segment comprising a 5' ITR linked to a second DNA segment comprising a promoter operably linked to a third DNA segment comprising a second open reading frame linked to a fourth DNA segment comprising a 3' ITR.

In another embodiment, one rAAV vector comprises a first DNA segment comprising a 5' ITR linked to a second DNA segment comprising a promoter operably linked to a third DNA segment comprising the 5' end of an open reading frame linked to fourth DNA segment comprising a 5' splice site linked to a fifth DNA segment comprising a 3' ITR. The second rAAV vector comprises a first DNA segment comprising a 5' ITR linked to a second DNA segment comprising a 3' splice site linked to a third DNA segment comprising the 3' end of the open reading frame linked to a fourth DNA segment comprising a 3' ITR. Preferably, the second and third DNA segments together comprise DNA encoding, for example, CTFR, factor VIII, dystrophin, or erythropoietin. Also preferably, the second DNA segment comprises the endogenous promoter of the respective gene, e.g., the epo promoter.

Thus, the invention provides a composition comprising: a first adeno-associated virus vector comprising linked DNA segments and at least a second adeno-associated virus comprising linked DNA segments. The linked DNA segments of the first vector comprise: a first DNA segment comprising a 5' ITR; a second DNA segment comprising at least a portion of an open reading frame operably linked to a promoter, wherein the DNA segment does not comprise the entire open reading frame; a third DNA segment comprising a splice donor site; and iv) a fourth DNA segment comprising a 3' ITR. The linked DNA segments of the second vector comprise a first DNA segment comprising a 5' ITR; a second DNA segment comprising a splice acceptor site; a third DNA segment comprising at least a portion of an open reading frame which together with the second DNA segment of the first vector encodes a full-length polypeptide; and a fourth DNA segment comprising a 3' ITR. Preferably, the second DNA segment of the first vector comprises a first exon of a gene comprising more than one exon and the third DNA segment of the second vector comprises at least one exon of a gene that is not the first exon.

The invention also provides a method to transfer and express a polypeptide in a host cell. The method comprises contacting the host cell with at least two rAAV vectors. One rAAV vector comprises a first DNA segment comprising a 5' ITR linked to a second DNA segment comprising a promoter operably linked to a third DNA segment comprising a first open reading frame linked to a fourth DNA segment comprising a 3' ITR. A second rAAV vector comprises a first DNA segment comprising a 5' ITR linked to a second DNA segment comprising a promoter operably linked to a third DNA segment comprising a second open reading frame linked to a fourth DNA segment comprising a 3'ITR. Alternatively, one rAAV vector comprises a first DNA segment comprising a 5' ITR linked to a second DNA segment comprising a promoter operably linked to a third DNA segment comprising the 5' end of an open reading frame linked to fourth DNA segment comprising a 5' splice site linked to a fifth DNA segment comprising a 3' ITR. The second rAAV vector comprises a first DNA segment comprising a 5' ITR linked to a second DNA segment comprising a 3' splice site linked to a third DNA segment comprising the 3' end of the open reading frame linked to a fourth DNA segment comprising a 3' ITR. The host cell is preferably contacted with both of the vectors, concurrently, although it is envisioned that the host cell may be contacted with each vector at a different time relative to the contact with the other vector(s).

Also provided is a method in which the composition of the invention is administered to the cells or tissues of an animal. For example, rAAV vectors have shown promise in transferring the CFTR gene into airway epithelial cells of animal models and nasal sinus of CF patients. However, high level expression of CFTR has not been achieved due to the fact that AAV cannot accommodate the full-length CFTR gene together with a potent promoter. A number of studies have tried to optimize rAAV-mediated CFTR expression by utilizing truncated or partially deleted CFTR genes together with stronger promoters. However, it is currently unknown what effect deletions within the CFTR gene may have on complementation of bacterial colonization defects in the CF airway. Therefore, the present invention includes the administration to an animal of a composition of the invention comprising at least two rAAV vectors which together encode CTFR. The present invention is useful to overcome the current size limitation for transgenes within rAAV vectors, and allows for the incorporation of a larger transciptional regulatory region, e.g., a stronger heterologous promoter or the endogenous CFTR promoter.

BRIEF DESCRIPTION OF THE FIGURES

FIG. 10(Parts A–C). Individual chemical sequence of SphI fragments from p81 (A; SEQ ID NO:4), p79 (B; SEQ ID NO:5), and p1202 (C; SEQ ID NO:6) AAV circular intermediates. The ends of the sequence (underlined) represent SphI restriction enzyme sites within head-to-tail circular AAV genomes cloned with the AV-GFP3ori shuttle virus.

FIG. 11. Chemical sequence homology of three AAV circular intermediates (SEQ ID NO:4, SEQ ID NO:5, SEQ ID NO:6) with various conformations of ITR arrays. Diversity in ITR arrays are evident from the non-conserved bases marked in lower case. The ends of the sequence (underlined) represent SphI restriction enzyme sites within head-to-tail circular AAV genomes cloned with the AV.GFP3ori shuttle virus.

DETAILED DESCRIPTION OF THE INVENTION

Definitions

Figure 1A:
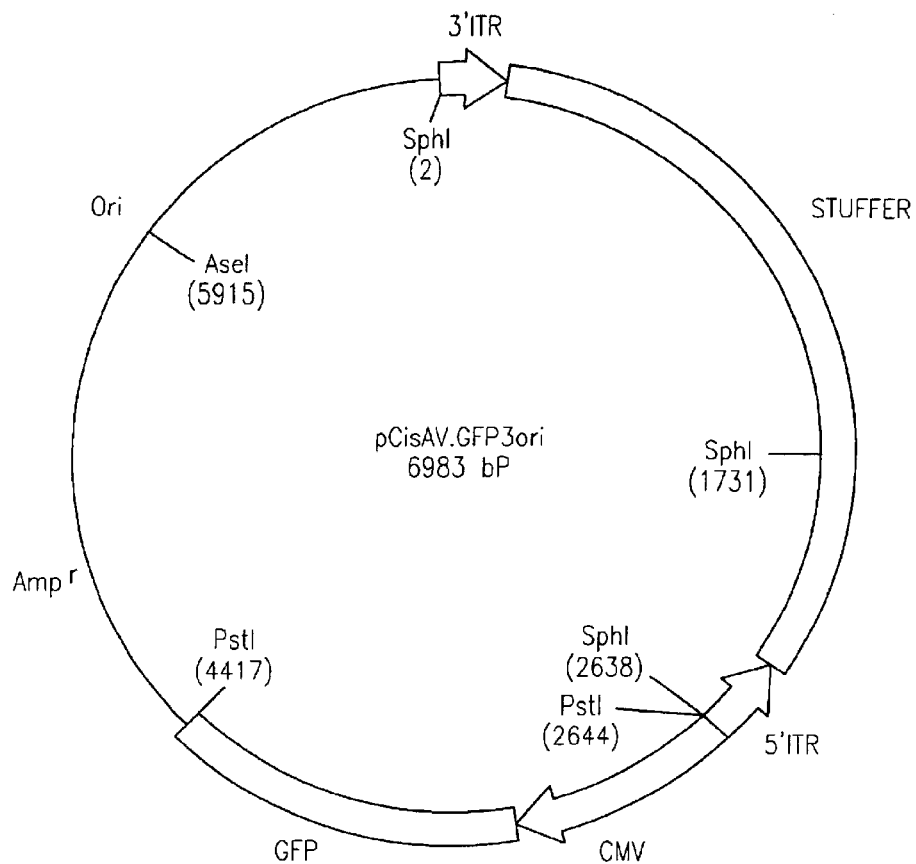
FIG. 1(Parts A–D). Structure of proviral shuttle vector and the predicted structure of rAAV circular intermediate monomers. With the aid of a rAAV cis-acting plasmid, pCisAV.GFP3ori (Panel A), AV.GFP3ori recombinant virus was produced (Panel B). This vector encoded a GFP transgene cassette, an ampicillin resistance gene (amp), and a bacterial replication origin (ori). The predominant form of circular intermediates isolated following transduction of Hela cells with AV.GFP3ori consisted of head-to-tail monomers (Panels C and D).

As used herein, the terms "isolated and/or purified" refer to in vitro preparation, isolation and/or purification of a nucleic acid molecule of the invention, so that it is not associated with in vivo substances.

As used herein, a DNA molecule, sequence or segment of the invention preferably is biologically active. A biologically active DNA molecule of the invention has at least about 1%, more preferably at least about 10%, and more preferably at least about 50%, of the activity of a DNA molecule comprising ITR sequences from a circular intermediate of AAV, e.g., a DNA molecule comprising SEQ ID NO:3, SEQ ID NO:4, SEQ ID NO:5, SEQ ID NO:6, or a subunit or variant thereof. The activity of a nucleic acid molecule of the invention can be measured by methods well known to the art, some of which are described hereinbelow. For example, the presence of the DNA molecule in a recombinant nucleic acid molecule in a host cell results in episomal persistence and/or increased abundance of the recombinant molecule in those cells relative to corresponding cells having a recombinant nucleic acid molecule lacking a DNA molecule of the invention.

A variant DNA molecule, sequence or segment of the invention has at least about 70%, preferably at least about 80%, and more preferably at least about 90%, but less than 100%, contiguous nucleotide sequence homology or identity to a DNA molecule comprising ITR sequences from a circular intermediate of AAV, e.g., SEQ ID NO:3, SEQ ID NO:4, SEQ ID NO:5, SEQ ID NO:6, a subunit thereof. A variant DNA molecule of the invention may include nucleotide bases not present in SEQ ID NO:3, SEQ ID NO:4, SEQ ID NO:5, SEQ ID NO:6, e.g., 5', 3' or internal deletions or insertions, such as the insertion of a restriction endonuclease recognition site, so long as these bases do not substantially reduce the biological activity of the molecule. A substantial reduction in activity means a reduction in activity of greater than about 50%, preferably greater than about 90%.

I. Identification of Nucleic Acid Molecules Falling Within the Scope of the Invention A. Nucleic Acid Molecules of the Invention 1. Sources of the Nucleic Acid Molecules of the Invention Sources of nucleotide sequences from which the present nucleic acid molecules can be obtained include AAV infected cells, e.g., any vertebrate, preferably mammalian, cellular source.

As used herein, the terms "isolated and/or purified" refer to in vitro isolation of a nucleic acid, e.g., DNA molecule from its natural cellular environment, and from association with other components of the cell, such as nucleic acid or polypeptide, so that it can be sequenced, replicated, and/or expressed. For example, "isolated nucleic acid" is RNA or DNA containing greater than about 50, preferably about 300, and more preferably about 500 or more, sequential nucleotide bases that comprise a DNA segment from a circular intermediate of AAV which contains at least a portion of the 5' and 3' ITRs and the D sequence, or a variant thereof, that is complementary or hybridizes, respectively, to AAV ITR DNA and remains stably bound under stringent conditions, as defined by methods well known in the art, e.g., in Sambrook et al., 1989. Thus, the RNA or DNA is "isolated" in that it is free from at least one contaminating nucleic acid with which it is normally associated in the natural source of the RNA or DNA and is preferably substantially free of any other mammalian RNA or DNA. The phrase "free from at least one contaminating source nucleic acid with which it is normally associated" includes the case where the nucleic acid is reintroduced into the source or natural cell but is in a different chromosomal location or is otherwise flanked by nucleic acid sequences not normally found in the source cell, e.g., in a vector or plasmid. An example of isolated nucleic acid within the scope of the invention is nucleic acid that shares at least about 80%, preferably at least about 90%, and more preferably at least about 95%, sequence identity with SEQ ID NO:3, SEQ ID NO:4, SEQ ID NO:5 or SEQ ID NO:6, or a subunit thereof.

As used herein, the term "recombinant nucleic acid" or "preselected nucleic acid," e.g., "recombinant DNA sequence or segment" or "preselected DNA sequence or segment" refers to a nucleic acid, e.g., to DNA, that has been derived or isolated from any appropriate cellular source, that may be subsequently chemically altered in vitro, so that its sequence is not naturally occurring, or corresponds to naturally occurring sequences that are not positioned as they would be positioned in a genome which has not been transformed with exogenous DNA. An example of preselected DNA "derived" from a source, would be a DNA sequence that is identified as a useful fragment within a given organism, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

Thus, recovery or isolation of a given fragment of DNA from a restriction digest can employ separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. See Lawn et al., *Nucleic Acids Res.,* 9, 6103 (1981), and Goeddel et al., *Nucleic Acids Res.,* 8, 4057 (1980). Therefore, "preselected DNA" includes completely synthetic DNA sequences, semi-synthetic DNA sequences, DNA sequences isolated from biological sources, and DNA sequences derived from RNA, as well as mixtures thereof.

Nucleic acid molecules having base pair substitutions (i.e., variants) are prepared by a variety of methods known in the art. These methods include, but are not limited to, isolation from a natural source (in the case of naturally occurring sequence variants) or preparation by oligonucleotide-mediated (or site-directed) mutagenesis, PCR mutagenesis, and cassette mutagenesis of an earlier prepared variant or a non-variant version of the nucleic acid molecule.

Oligonucleotide-mediated mutagenesis is a preferred method for preparing substitution variants. This technique is well known in the art as described by Adelman et al., *DNA,* 2, 183 (1983). Briefly, AAV DNA is altered by hybridizing an oligonucleotide encoding the desired mutation to a DNA template, where the template is the single-stranded form of a plasmid or bacteriophage containing the unaltered or native DNA sequence of AAV. After hybridization, a DNA polymerase is used to synthesize an entire second complementary strand of the template that will thus incorporate the oligonucleotide primer, and will code for the selected alteration in the AAV DNA.

Generally, oligonucleotides of at least 25 nucleotides in length are used. An optimal oligonucleotide will have 12 to 15 nucleotides that are completely complementary to the template on either side of the nucleotide(s) coding for the mutation. This ensures that the oligonucleotide will hybridize properly to the single-stranded DNA template molecule. The oligonucleotides are readily synthesized using techniques known in the art such as that described by Crea et al., *Proc. Natl. Acad. Sci. U.S.A.,* 75, 5765 (1978).

The DNA template can be generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.,* 153, 3 (1987). Thus, the DNA that is to be mutated may be inserted into one of these vectors to generate single-stranded template. Production of the single-stranded template is described in Sections 4.21–4.41 of Sambrook et al., *Molecular Cloning: A Laboratory Manual* (Cold Spring Harbor Laboratory Press, N.Y. 1989).

Alternatively, single-stranded DNA template may be generated by denaturing double-stranded plasmid (or other) DNA using standard techniques.

For alteration of the native DNA sequence (to generate amino acid sequence variants, for example), the oligonucleotide is hybridized to the single-stranded template under suitable hybridization conditions. A DNA polymerizing enzyme, usually the Klenow fragment of DNA polymerase I, is then added to synthesize the complementary strand of the template using the oligonucleotide as a primer for synthesis. A heteroduplex molecule is thus formed such that one strand of DNA encodes the mutated form of AAV, and the other strand (the original template) encodes the native, unaltered sequence of AAV. This heteroduplex molecule is then transformed into a suitable host cell, usually a prokaryote such as *E. coli* JM101. After the cells are grown, they are plated onto agarose plates and screened using the oligonucleotide primer radiolabeled with 32-phosphate to identify the bacterial colonies that contain the mutated DNA. The mutated region is then removed and placed in an appropriate vector, generally an expression vector of the type typically employed for transformation of an appropriate host.

The method described immediately above may be modified such that a homoduplex molecule is created wherein both strands of the plasmid contain the mutations(s). The modifications are as follows: The single-stranded oligonucleotide is annealed to the single-stranded template as described above. A mixture of three deoxyribonucleotides, deoxyriboadenosine (dATP), deoxyriboguanosine (dGTP), and deoxyribothymidine (dTTP), is combined with a modified thiodeoxyribocytosine called dCTP-(αS) (which can be obtained from the Amersham Corporation). This mixture is added to the template-oligonucleotide complex. Upon addition of DNA polymerase to this mixture, a strand of DNA identical to the template except for the mutated bases is generated. In addition, this new strand of DNA will contain dCTP-(αS) instead of dCTP, which serves to protect it from restriction endonuclease digestion.

After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell such as *E. coli* JM101.

For example, a preferred embodiment of the invention is an isolated and purified DNA molecule comprising a DNA segment comprising SEQ ID NO:3, SEQ ID NO:4, SEQ ID NO:5, SEQ ID NO:6, a subunit thereof or a variant thereof having nucleotide substitutions, or deletions or insertions.

II. Preparation of Molecules Useful to Practice the Methods of the Invention

A. Nucleic Acid Molecules

1. Chimeric Expression Cassettes

To prepare expression cassettes for transformation herein, the recombinant or preselected DNA sequence or segment may be circular or linear, double-stranded or single-stranded. Generally, the preselected DNA sequence or segment is in the form of chimeric DNA, such as plasmid DNA, that can also contain coding regions flanked by control sequences which promote the expression of the preselected DNA present in the resultant cell line.

As used herein, "chimeric" means that a vector comprises DNA from at least two different species, or comprises DNA from the same species, which is linked or associated in a manner which does not occur in the "native" or wild type of the species.

Aside from the preselected DNA sequences described above, a portion of the preselected DNA may serve a regulatory or a structural function. For example, the preselected DNA may itself comprise a promoter that is active in mammalian cells, or may utilize a promoter already present in the genome that is the transformation target. Such promoters include the CMV promoter, as well as the SV40 late promoter and retroviral LTRs (long terminal repeat elements), although many other promoter elements well known to the art may be employed in the practice of the invention.

Other elements functional in the host cells, such as introns, enhancers, polyadenylation sequences and the like, may also be a part of the preselected DNA. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

The preselected DNA to be introduced into the cells further will generally contain either a selectable marker gene or a reporter gene or both to facilitate identification and selection of transformed cells from the population of cells sought to be transformed. Alternatively, the selectable marker may be carried on a separate piece of DNA and used in a co-transformation procedure. Both selectable markers and reporter genes may be flanked with appropriate regulatory sequences to enable expression in the host cells. Useful selectable markers are well known in the art and include, for example, antibiotic and herbicide-resistance genes, such as neo, hpt, dhfr, bar, aroA, dapA and the like. See also, the genes listed on Table 1 of Lundquist et al. (U.S. Pat. No. 5,848,956).

Reporter genes are used for identifying potentially transformed cells and for evaluating the functionality of regulatory sequences. Reporter genes which encode for easily assayable proteins are well known in the art. In general, a reporter gene is a gene which is not present in or expressed by the recipient organism or tissue and which encodes a protein whose expression is manifested by some easily detectable property, e.g., enzymatic activity. Preferred genes include the chloramphenicol acetyl transferase gene (cat) from Tn9 of *E. coli*, the beta-glucuronidase gene (gus) of the uidA locus of *E. coli*, and the luciferase gene from firefly *Photinus pyralis*. Expression of the reporter gene is assayed at a suitable time after the DNA has been introduced into the recipient cells.

The general methods for constructing recombinant DNA which can transform target cells are well known to those skilled in the art, and the same compositions and methods of construction may be utilized to produce the DNA useful herein. For example, J. Sambrook et al., *Molecular Cloning: A Laboratory Manual*, Cold Spring Harbor Laboratory Press (2d ed., 1989), provides suitable methods of construction.

2. Transformation into Host Cells

The recombinant DNA can be readily introduced into the host cells, e.g., mammalian, bacterial, yeast or insect cells by transfection with an expression vector of the invention, by any procedure useful for the introduction into a particular cell, e.g., physical or biological methods, to yield a transformed cell having the recombinant DNA stably integrated into its genome or present as an episome which can persist in the transformed cells, so that the DNA molecules, sequences, or segments, of the present invention are maintained and/or expressed by the host cell.

Physical methods to introduce a preselected DNA into a host cell include calcium phosphate precipitation, lipofection, particle bombardment, microinjection, electroporation, and the like. Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression.

As used herein, the term "cell line" or "host cell" is intended to refer to well-characterized homogenous, biologically pure populations of cells. These cells may be eukaryotic cells that are neoplastic or which have been "immortalized" in vitro by methods known in the art, as well as primary cells, or prokaryotic cells. The cell line or host cell is preferably of mammalian origin, but cell lines or host cells of non-mammalian origin may be employed, including plant, insect, yeast, fungal or bacterial sources. Generally, the preselected DNA sequence is related to a DNA sequence which is resident in the genome of the host cell but is not expressed, or not highly expressed, or, alternatively, overexpressed.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering. The host cells of the present invention are typically produced by transfection with a DNA sequence in a plasmid expression vector, a viral expression vector, or as an isolated linear DNA sequence.

To confirm the presence of the preselected DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence of a polypeptide expressed from a gene present in the vector, e.g., by immunological means (immunoprecipitations, immunoaffinity columns, ELISAs and Western blots) or by any other assay useful to identify molecules falling within the scope of the invention.

To detect and quantitate RNA produced from introduced DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the DNA segment in question, they do not provide information as to whether the DNA segment is being expressed. Expression may be evaluated by specifically identifying the polypeptide products of the introduced DNA sequences or evaluating the phenotypic changes brought about by the expression of the introduced DNA segment in the host cell.

III. Dosages, Formulations and Routes of Administration

Administration of a nucleic acid molecule may be accomplished through the introduction of cells transformed with the nucleic acid molecule (see, for example, WO 93/02556), the administration of the nucleic acid molecule itself (see, for example, Felgner et al., U.S. Pat. No. 5,580,859, Pardoll et al., *Immunity*, 3, 165 (1995); Stevenson et al., *Immunol. Rev.* 145, 211 (1995); Molling, *J. Mol. Med.*, 75, 242 (1997); Donnelly et al., *Ann. N.Y. Acad. Sci.*, 772, 40 (1995); Yang et al., *Mol. Med. Today*, 2, 476 (1996); Abdallah et al., *Biol. Cell*, 85, 1 (1995)), through infection with a recombinant virus or via liposomes. Pharmaceutical formulations, dosages and routes of administration for nucleic acids are generally disclosed, for example, in Felgner et al., supra.

Administration of the therapeutic agents in accordance with the present invention may be continuous or intermittent, depending, for example, upon the recipient's physiological condition, whether the purpose of the administration is therapeutic or prophylactic, and other factors known to skilled practitioners. The administration of the agents of the invention may be essentially continuous over a preselected period of time or may be in a series of spaced doses. Both local and systemic administration is contemplated. When the molecules of the invention are employed for prophylactic purposes, agents of the invention are amenable to chronic use, preferably by systemic administration.

One or more suitable unit dosage forms comprising the therapeutic agents of the invention, which, as discussed below, may optionally be formulated for sustained release, can be administered by a variety of routes including oral, or parenteral, including by rectal, transdermal, subcutaneous, intravenous, intramuscular, intraperitoneal, intrathoracic, intrapulmonary and intranasal routes. The formulations may, where appropriate, be conveniently presented in discrete unit dosage forms and may be prepared by any of the methods well known to pharmacy. Such methods may include the step of bringing into association the therapeutic agent with liquid carriers, solid matrices, semi-solid carriers, finely divided solid carriers or combinations thereof, and then, if necessary, introducing or shaping the product into the desired delivery system.

When the therapeutic agents of the invention are prepared for oral administration, they are preferably combined with a pharmaceutically acceptable carrier, diluent or excipient to form a pharmaceutical formulation, or unit dosage form. The total active ingredients in such formulations comprise from 0.1 to 99.9% by weight of the formulation. By "pharmaceutically acceptable" it is meant the carrier, diluent, excipient, and/or salt must be compatible with the other ingredients of the formulation, and not deleterious to the recipient thereof. The active ingredient for oral administration may be present as a powder or as granules; as a solution, a suspension or an emulsion; or in achievable base such as a synthetic resin for ingestion of the active ingredients from a chewing gum. The active ingredient may also be presented as a bolus, electuary or paste.

Pharmaceutical formulations containing the therapeutic agents of the invention can be prepared by procedures known in the art using well known and readily available ingredients. For example, the agent can be formulated with common excipients, diluents, or carriers, and formed into tablets, capsules, suspensions, powders, and the like. Examples of excipients, diluents, and carriers that are suitable for such formulations include the following fillers and extenders such as starch, sugars, mannitol, and silicic derivatives; binding agents such as carboxymethyl cellulose, HPMC and other cellulose derivatives, alginates, gelatin, and polyvinyl-pyrrolidone; moisturizing agents such as glycerol; disintegrating agents such as calcium carbonate and sodium bicarbonate; agents for retarding dissolution such as paraffin; resorption accelerators such as quaternary ammonium compounds; surface active agents such as cetyl alcohol, glycerol monostearate; adsorptive carriers such as kaolin and bentonite; and lubricants such as talc, calcium and magnesium stearate, and solid polyethyl glycols.

For example, tablets or caplets containing the agents of the invention can include buffering agents such as calcium carbonate, magnesium oxide and magnesium carbonate. Caplets and tablets can also include inactive ingredients such as cellulose, pregelatinized starch, silicon dioxide, hydroxy propyl methyl cellulose, magnesium stearate, microcrystalline cellulose, starch, talc, titanium dioxide, benzoic acid, citric acid, corn starch, mineral oil, polypropylene glycol, sodium phosphate, and zinc stearate, and the like. Hard or soft gelatin capsules containing an agent of the invention can contain inactive ingredients such as gelatin, microcrystalline cellulose, sodium lauryl sulfate, starch, talc, and titanium dioxide, and the like, as well as liquid vehicles such as polyethylene glycols (PEGs) and vegetable oil. Moreover, enteric coated caplets or tablets of an agent of the invention are designed to resist disintegration in the stomach and dissolve in the more neutral to alkaline environment of the duodenum.

The therapeutic agents of the invention can also be formulated as elixirs or solutions for convenient oral administration or as solutions appropriate for parenteral administration, for instance by intramuscular, subcutaneous or intravenous routes.

The pharmaceutical formulations of the therapeutic agents of the invention can also take the form of an aqueous or anhydrous solution or dispersion, or alternatively the form of an emulsion or suspension.

Thus, the therapeutic agent may be formulated for parenteral administration (e.g., by injection, for example, bolus injection or continuous infusion) and may be presented in unit dose form in ampules, pre-filled syringes, small volume infusion containers or in multi-dose containers with an added preservative. The active ingredients may take such forms as suspensions, solutions, or emulsions in oily or aqueous vehicles, and may contain formulatory agents such as suspending, stabilizing and/or dispersing agents. Alternatively, the active ingredients may be in powder form, obtained by aseptic isolation of sterile solid or by lyophilization from solution, for constitution with a suitable vehicle, e.g., sterile, pyrogen-free water, before use.

These formulations can contain pharmaceutically acceptable vehicles and adjuvants which are well known in the prior art. It is possible, for example, to prepare solutions using one or more organic solvent(s) that is/are acceptable from the physiological standpoint, chosen, in addition to water, from solvents such as acetone, ethanol, isopropyl alcohol, glycol ethers such as the products sold under the name "Dowanol", polyglycols and polyethylene glycols, $C_1$–$C_4$ alkyl esters of short-chain acids, preferably ethyl or isopropyl lactate, fatty acid triglycerides such as the products marketed under the name "Miglyol", isopropyl myristate, animal, mineral and vegetable oils and polysiloxanes.

The compositions according to the invention can also contain thickening agents such as cellulose and/or cellulose derivatives. They can also contain gums such as xanthan, guar or carbo gum or gum arabic, or alternatively polyethylene glycols, bentones and montmorillonites, and the like.

It is possible to add, if necessary, an adjuvant chosen from antioxidants, surfactants, other preservatives, film-forming, keratolytic or comedolytic agents, perfumes and colorings. Also, other active ingredients may be added, whether for the conditions described or some other condition.

For example, among antioxidants, t-butylhydroquinone, butylated hydroxyanisole, butylated hydroxytoluene and α-tocopherol and its derivatives may be mentioned. The galenical forms chiefly conditioned for topical application take the form of creams, milks, gels, dispersion or microemulsions, lotions thickened to a greater or lesser extent, impregnated pads, ointments or sticks, or alternatively the form of aerosol formulations in spray or foam form or alternatively in the form of a cake of soap.

Additionally, the agents are well suited to formulation as sustained release dosage forms and the like. The formulations can be so constituted that they release the active ingredient only or preferably in a particular part of the intestinal or respiratory tract, possibly over a period of time. The coatings, envelopes, and protective matrices may be made, for example, from polymeric substances, such as polylactide-glycolates, liposomes, microemulsions, microparticles, nanoparticles, or waxes. These coatings, envelopes, and protective matrices are useful to coat indwelling devices, e.g., stents, catheters, peritoneal dialysis tubing, and the like.

The therapeutic agents of the invention can be delivered via patches for transdermal administration. See U.S. Pat. No. 5,560,922 for examples of patches suitable for transdermal delivery of a therapeutic agent. Patches for transdermal delivery can comprise a backing layer and a polymer matrix which has dispersed or dissolved therein a therapeutic agent, along with one or more skin permeation enhancers. The backing layer can be made of any suitable material which is impermeable to the therapeutic agent. The backing layer serves as a protective cover for the matrix layer and provides also a support function. The backing can be formed so that it is essentially the same size layer as the polymer matrix or it can be of larger dimension so that it can extend beyond the side of the polymer matrix or overlay the side or sides of the polymer matrix and then can extend outwardly in a manner that the surface of the extension of the backing layer can be the base for an adhesive means. Alternatively, the polymer matrix can contain, or be formulated of, an adhesive polymer, such as polyacrylate or acrylate/vinyl acetate copolymer. For long-term applications it might be desirable to use microporous and/or breathable backing laminates, so hydration or maceration of the skin can be minimized.

Examples of materials suitable for making the backing layer are films of high and low density polyethylene, polypropylene, polyurethane, polyvinylchloride, polyesters such as poly(ethylene phthalate), metal foils, metal foil laminates of such suitable polymer films, and the like. Preferably, the materials used for the backing layer are laminates of such polymer films with a metal foil such as aluminum foil. In such laminates, a polymer film of the laminate will usually be in contact with the adhesive polymer matrix.

The backing layer can be any appropriate thickness which will provide the desired protective and support functions. A suitable thickness will be from about 10 to about 200 microns.

Generally, those polymers used to form the biologically acceptable adhesive polymer layer are those capable of forming shaped bodies, thin walls or coatings through which therapeutic agents can pass at a controlled rate. Suitable polymers are biologically and pharmaceutically compatible, nonallergenic and insoluble in and compatible with body fluids or tissues with which the device is contacted. The use of soluble polymers is to be avoided since dissolution or erosion of the matrix by skin moisture would affect the release rate of the therapeutic agents as well as the capability of the dosage unit to remain in place for convenience of removal.

Exemplary materials for fabricating the adhesive polymer layer include polyethylene, polypropylene, polyurethane, ethylene/propylene copolymers, ethylene/ethylacrylate copolymers, ethylene/vinyl acetate copolymers, silicone elastomers, especially the medical-grade polydimethylsiloxanes, neoprene rubber, polyisobutylene, polyacrylates, chlorinated polyethylene, polyvinyl chloride, vinyl chloride-vinyl acetate copolymer, crosslinked polymethacrylate polymers (hydrogel), polyvinylidene chloride, poly(ethylene terephthalate), butyl rubber, epichlorohydrin rubbers, ethylenvinyl alcohol copolymers, ethylene-vinyloxyethanol copolymers; silicone copolymers, for example, polysiloxane-polycarbonate copolymers, polysiloxanepolyethylene oxide copolymers, polysiloxane-polymethacrylate copolymers, polysiloxane-alkylene copolymers (e.g., polysiloxane-ethylene copolymers), polysiloxane-alkylenesilane copolymers (e.g., polysiloxane-ethylenesilane copolymers), and the like; cellulose polymers, for example methyl or ethyl cellulose, hydroxy propyl methyl cellulose, and cellulose esters; polycarbonates; polytetrafluoroethylene; and the like.

Preferably, a biologically acceptable adhesive polymer matrix should be selected from polymers with glass transition temperatures below room temperature. The polymer may, but need not necessarily, have a degree of crystallinity at room temperature. Cross-linking monomeric units or sites can be incorporated into such polymers. For example, cross-linking monomers can be incorporated into polyacrylate polymers, which provide sites for cross-linking the matrix after dispersing the therapeutic agent into the polymer. Known cross-linking monomers for polyacrylate polymers include polymethacrylic esters of polyols such as butylene diacrylate and dimethacrylate, trimethylol propane trimethacrylate and the like. Other monomers which provide such sites include allyl acrylate, allyl methacrylate, diallyl maleate and the like.

Preferably, a plasticizer and/or humectant is dispersed within the adhesive polymer matrix. Water-soluble polyols are generally suitable for this purpose. Incorporation of a humectant in the formulation allows the dosage unit to absorb moisture on the surface of skin which in turn helps to reduce skin irritation and to prevent the adhesive polymer layer of the delivery system from failing.

Therapeutic agents released from a transdermal delivery system must be capable of penetrating each layer of skin. In order to increase the rate of permeation of a therapeutic agent, a transdermal drug delivery system must be able in particular to increase the permeability of the outermost layer of skin, the stratum corneum, which provides the most resistance to the penetration of molecules. The fabrication of patches for transdermal delivery of therapeutic agents is well known to the art.

For administration to the upper (nasal) or lower respiratory tract by inhalation, the therapeutic agents of the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount.

Alternatively, for administration by inhalation or insufflation, the composition may take the form of a dry powder, for example, a powder mix of the therapeutic agent and a suitable powder base such as lactose or starch. The powder composition may be presented in unit dosage form in, for example, capsules or cartridges, or, e.g., gelatine or blister packs from which the powder may be administered with the aid of an inhalator, insufflator or a metered-dose inhaler.

For intra-nasal administration, the therapeutic agent may be administered via nose drops, a liquid spray, such as via a plastic bottle atomizer or metered-dose inhaler. Typical of atomizers are the Mistometer (Wintrop) and the Medihaler (Riker).

The local delivery of the therapeutic agents of the invention can also be by a variety of techniques which administer the agent at or near the site of disease. Examples of site-specific or targeted local delivery techniques are not intended to be limiting but to be illustrative of the techniques available. Examples include local delivery catheters, such as an infusion or indwelling catheter, e.g., a needle infusion catheter, shunts and stents or other implantable devices, site specific carriers, direct injection, or direct applications.

For topical administration, the therapeutic agents may be formulated as is known in the art for direct application to a target area. Conventional forms for this purpose include wound dressings, coated bandages or other polymer coverings, ointments, creams, lotions, pastes, jellies, sprays, and aerosols. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. The active ingredients can also be delivered via iontophoresis, e.g., as disclosed in U.S. Pat. Nos. 4,140,122; 4,383,529; or 4,051,842. The percent by weight of a therapeutic agent of the invention present in a topical formulation will depend on various factors, but generally will be from 0.01% to 95% of the total weight of the formulation, and typically 0.1–25% by weight.

Drops, such as eye drops or nose drops, may be formulated with an aqueous or non-aqueous base also comprising one or more dispersing agents, solubilizing agents or suspending agents. Liquid sprays are conveniently delivered from pressurized packs. Drops can be delivered via a simple eye dropper-capped bottle, or via a plastic bottle adapted to deliver liquid contents dropwise, via a specially shaped closure.

The therapeutic agent may further be formulated for topical administration in the mouth or throat. For example, the active ingredients may be formulated as a lozenge further comprising a flavored base, usually sucrose and acacia or tragacanth; pastilles comprising the composition in an inert base such as gelatin and glycerin or sucrose and acacia; and mouthwashes comprising the composition of the present invention in a suitable liquid carrier.

The formulations and compositions described herein may also contain other ingredients such as antimicrobial agents, or preservatives. Furthermore, the active ingredients may also be used in combination with other therapeutic agents, for example, bronchodilators.

In particular, for delivery of a vector of the invention to a tissue such as muscle, any physical or biological method that will introduce the vector into the muscle tissue of a host animal can be employed. Vector means both a bare recombinant vector and vector DNA packaged into viral coat proteins, as is well known for AAV administration. Simply dissolving an AAV vector in phosphate buffered saline has been demonstrated to be sufficient to provide a vehicle useful for muscle tissue expression, and there are no known restrictions on the carriers or other components that can be coadministered with the vector (although compositions that degrade DNA should be avoided in the normal manner with vectors). Pharmaceutical compositions can be prepared as injectable formulations or as topical formulations to be delivered to the muscles by transdermal transport. Numerous formulations for both intramuscular injection and transdermal transport have been previously developed and can be used in the practice of the invention. The vectors can be used with any pharmaceutically acceptable carrier for ease of administration and handling.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of the AAV vector as a free acid (DNA contains acidic phosphate groups) or a pharmacologically acceptable salt can be prepared in water suitably mixed with a surfactant such as hydroxypropylcellulose. A dispersion of AAV viral particles can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

Sterile injectable solutions are prepared by incorporating the AAV vector in the required amount in the appropriate solvent with various of the other ingredients enumerated above, as required, followed by filtered sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from the previously sterile-filtered solution thereof.

For purposes of topical administration, dilute sterile, aqueous solutions (usually in about 0.1% to 5% concentration), otherwise similar to the above parenteral solutions, are prepared in containers suitable for incorporation into a transdermal patch, and can include known carriers, such as pharmaceutical grade dimethylsulfoxide (DMSO).

The therapeutic compounds of this invention may be administered to a mammal alone or in combination with pharmaceutically acceptable carriers. As noted above, the relative proportions of active ingredient and carrier are determined by the solubility and chemical nature of the compound, chosen route of administration and standard pharmaceutical practice.

The dosage of the present therapeutic agents which will be most suitable for prophylaxis or treatment will vary with the form of administration, the particular compound chosen and the physiological characteristics of the particular patient under treatment. Generally, small dosages will be used initially and, if necessary, will be increased by small increments until the optimum effect under the circumstances is reached. Exemplary dosages are set out in the example below.

Since AAV has been shown to have a broad host range (for pulmonary expression) and persists in muscle, the vectors of the invention may be employed to express a gene in any animal, and particularly in mammals, birds, fish, and reptiles, especially domesticated mammals and birds such as cattle, sheep, pigs, horses, dogs, cats, chickens, and turkeys. Both human and veterinary uses are particularly preferred.

The gene being expressed can be either a DNA segment encoding a protein, with whatever control elements (e.g., promoters, operators) are desired by the user, or a non-coding DNA segment, the transcription of which produces all or part of some RNA-containing molecule (such as a transcription control element, +RNA, or anti-sense molecule).

Muscle tissue is a very attractive target for in vivo gene delivery and gene therapy, because it is not a vital organ and is very easy to access. If a disease is caused by a defective gene product which is required to be produced and/or secreted, such as hemophilia, diabetes and Gaucher's disease, and the like, is muscle is a good candidate to supply the gene product if the appropriate gene can be effectively delivered into the cells.

Different vectors, such as naked DNA, adenovirus and retrovirus, have been utilized to directly deliver various transgenes into muscle tissues. However, neither system can offer both high efficiency and long-term expression. For naked plasmid DNA directly delivered into muscle tissue, the efficiency is not high. There are only a few cells near the injection site that can maintain transgene expression. Furthermore, the plasmid DNA in the cells remains as non-replicating episomes, i.e., in the unintegrated form. Therefore, it will be eventually lost. For adenovirus vector, it can infect the non-dividing cells, and therefore, can be directly delivered into the mature tissues such as muscle. However, the transgene delivered by adenovirus vectors are not useful to maintain long-term expression for the following reasons. First, since adenovirus vectors still retain most of the viral genes, they are not very safe. Moreover, the expression of those genes can cause the immune system to destroy the cells containing the vectors (see, for example, Yang et al. 1994, Proc. Natl. Acad. Sci. 91:4407–4411). Second, since adenovirus is not an integration virus, its DNA will eventually be diluted or degraded in the cells. Third, due to the immune response, adenovirus vector could not be repeatedly delivered. In the case of lifetime diseases, this will be a major limitation. For retrovirus vectors, although they can achieve stable integration into the host chromosomes, their use is very restricted because they can only infect dividing cells while a large majority of the muscle cells are non-dividing.

Adeno-associated virus vectors have certain advantages over the above-mentioned vector systems. First, like adenovirus, AAV can efficiently infect non-dividing cells. Second, all the AAV viral genes are eliminated in the vector. Since the viral-gene-expression-induced immune reaction is no longer a concern, AAV vectors are safer than Ad vectors. Thirds, AAV is an integration virus by nature, and integration into the host chromosome will stably maintain its transgene in the cells. Fourth, AAV is an extremely stable virus, which is resistant to many detergents, pH changes and heat (stable at 56° C. for more than an hour). It can be lyophilized and redissolved without losing its activity. Therefore, it is a very promising delivery vehicle for gene therapy.

The invention will be further described by, but is not limited to, the following examples.

EXAMPLE 1

Materials and Methods

Construction of rAAV Shuttle Vector.

A recombinant AAV shuttle vector (AV.GFP3ori) which contained a GFP transgene cassette, bacterial ampicillin resistance gene, and bacterial origin of replication, was generated from a cis-acting plasmid (pCisAV.GFP3ori). Expression of the GFP gene was directed by the CMV promoter/enhancer and SV40 poly-adenylation sequences. pCisAV.GFP3ori was constructed with pSub201 derived ITR elements (Samulski et al., 1987) and the intactness of ITR sequences was confirmed by restriction analysis with SmaI and PvuII, and by sequencing. Recombinant AAV stocks were generated by co-transfection of pCisAV.GFP3ori and pRep/Cap together with co-infection of recombinant Ad.CMVlacZ in 293 cells (Duan et al., 1997). Following transfection of forty 150 mm plates, cells were collected at 72 hours by centrifugation and resuspended in 12 ml of buffer (10 mM Tris pH 8.0). Virus was released from cells by three cycles of freeze/thawing and passaged through a 25 gauge needle six times. Cell lysates were then treated with 1.3 mg/ml DNase I at 37° C. for 30 minutes and 1% deoxycholate (g/ml final) and 0.05% trypsin (g/ml final) at 37° C. for 30 minutes. Samples were then placed on ice for 10 minutes and centrifuged to remove large particulate material at 3,000 rpm for 30 minutes.

rAAV was purified by isopycnic density gradient centrifugation in CsCl (r=1.4) in a SW55 rotor for 72 hours at 35K. Peak fractions of AAV were combined and re-purified through two more rounds of CsCl centrifugation, followed by heating at 58° C. for 60 minutes to inactivate all contaminant helper adenovirus. Typically, this preparation gave approximate AAV titers of $10^{12}$ DNA molecules/ml and $2.5 \times 10^8$ GFP-expressing units/ml. Recombinant viral titers were assessed by slot blot and quantified against pCisAV.GFP3ori controls for DNA particles. Functional transducing units were quantified by GFP transgene expression in 293 cells. The absence of helper adenovirus was confirmed by histochemical staining of rAAV infected 293 cells for beta-galactosidase, and no recombinant adenovirus was found in $10^{10}$ particles of purified rAAV stocks. The absence of significant wtAAV contamination was confirmed by immunocytochemical staining of rAAV/Ad co-infected 293 cells with anti-Rep antibodies. These studies, which had a sensitivity of 1 wtAAV in $10^{10}$ rAAV particles, demonstrated an absence of Rep staining as compared to pRep/Cap plasmid transfected controls.

Isolation and Structural Evaluation of AAV Circular Intermediates from Hela Cells.

Hela cells were grown in 35 mm dishes in DMEM media supplemented with 10% fetal calf serum (FCS). Cells were infected in the presence of 2% FCS at 80% confluency with recombinant AV.GFP3ori (MOI=1000 particles/cell, $1 \times 10^9$ total particles/plate) and Hirt DNAs isolated as described by Duan et al. (1997) at 6, 12, 24, 48, and 72 hours post-infection. In experiments analyzing the effects of adenovirus, plates were co-infected with Ad.CMVLacZ (MOI=5000 particles/cell) in the presence of 2%FCS/DMEM. Zero hour controls were generated by mixing $10^9$ particles of AV.GFP3ori with cell lysates prior to Hirt DNA preparation. Hirt DNA isolated at each time point was used to transform E. coli SURE cells (Stratagene, La Jolla, Calif.). Typically, 1/10 of the Hirt DNA preparation was used to transform 40 ml of competent bacteria by electroporation. The resultant total number of bacterial colonies was quantified for each time point and the structure of circular intermediates was evaluated for greater than 20 plasmid clones for each time point from two independent experiments. Structural determinations were based on restriction enzyme analysis using PstI, SphI, AseI single and double digests together with Southern blotting against GFP, stuffer, and ITR probes.

Evaluation of E2a and GFP Gene Expression in Hela Cells.

E2a gene expression was evaluated by immunofluorescent staining of Hela cells superinfected with E1-deleted Ad.CMVlacZ (MOI=0, 500, 5000 particles/cell). Briefly, cells were fixed in methanol at −20° C. for 10 minutes followed by air drying. Cells were then incubated at room temperature with hybridoma supernatant against Ad5 72 kd DBP (Reich et al., 1983), followed by goat anti-mouse-FITC antibody (5 mg/ml) for 30 minutes at room temperature. In studies evaluating augmentation of AAV GFP transgene expression by adenovirus, Hela cells were harvested at 24 or 72 hours post-infection by trypsinization, resuspended in 2%FCS/PBS and evaluated by FACS analyses. Thresholds were set using uninfected controls and the percentage and/or the average relative fluorescent intensity was determined by sorting greater than $10^5$ cells per experiment condition.

Sequence Analysis of AAV Circular Intermediates.

Sequence analysis of the ITR array within circular intermediates was performed using primers EL118 (5'-CGGGGGTCGTTGGGCGGTCA-3'; SEQ ID NO:1) and EL230 (5'-GGGCGGAGCCTATGGAAAA-3'; SEQ ID NO:2) which are nested to 5' and 3' ITR sequences, respectively. Both circular and linearized (with SmaI which cuts within ITR sequences) plasmids were sequenced.

Results

Construction of rAAV Shuttle Vector and Isolation of Circular Intermediates.

To circumvent the inability to retrieve pre-integration intermediates or as stable episomal forms resistant to nuclease digestion, an alternative strategy was developed to "trap" circular intermediates using a recombinant AAV shuttle vector. Recombinant AV.GFP3ori virus (FIG. 1B) was generated from a cis-acting plasmid (pCisAV.GFP3ori, FIG. 1A) by co-transfection in 293 cells with trans-acting plasmids encoding Rep and Cap viral genes. This viral vector (AV.GFP3ori) encoded the green fluorescent protein (GFP) reporter gene, a bacterial origin of replication (ori), and the bacterial ampicillin-resistance gene. Ori and ampicillin-resistance sequences encoded in this virus allow for the rescue of circular AAV genomes formed during the transduction process.

To test this strategy, Hela cells were infected with AV.GFP3ori (MOI=1000 particles/cell) and the abundance of circular intermediates was evaluated following transformation of low molecular weight cellular Hirt DNA into *E. coli* SURE cells. The presence of circular intermediates was inferred by retrievable ampicillin-resistant bacterial colonies. Structural features of circular intermediates were determined by restriction enzyme analysis and Southern blotting with various regions of the provirus, including GFP, Stuffer, and ITR sequences.

Figure 1B:
Figure 1C:
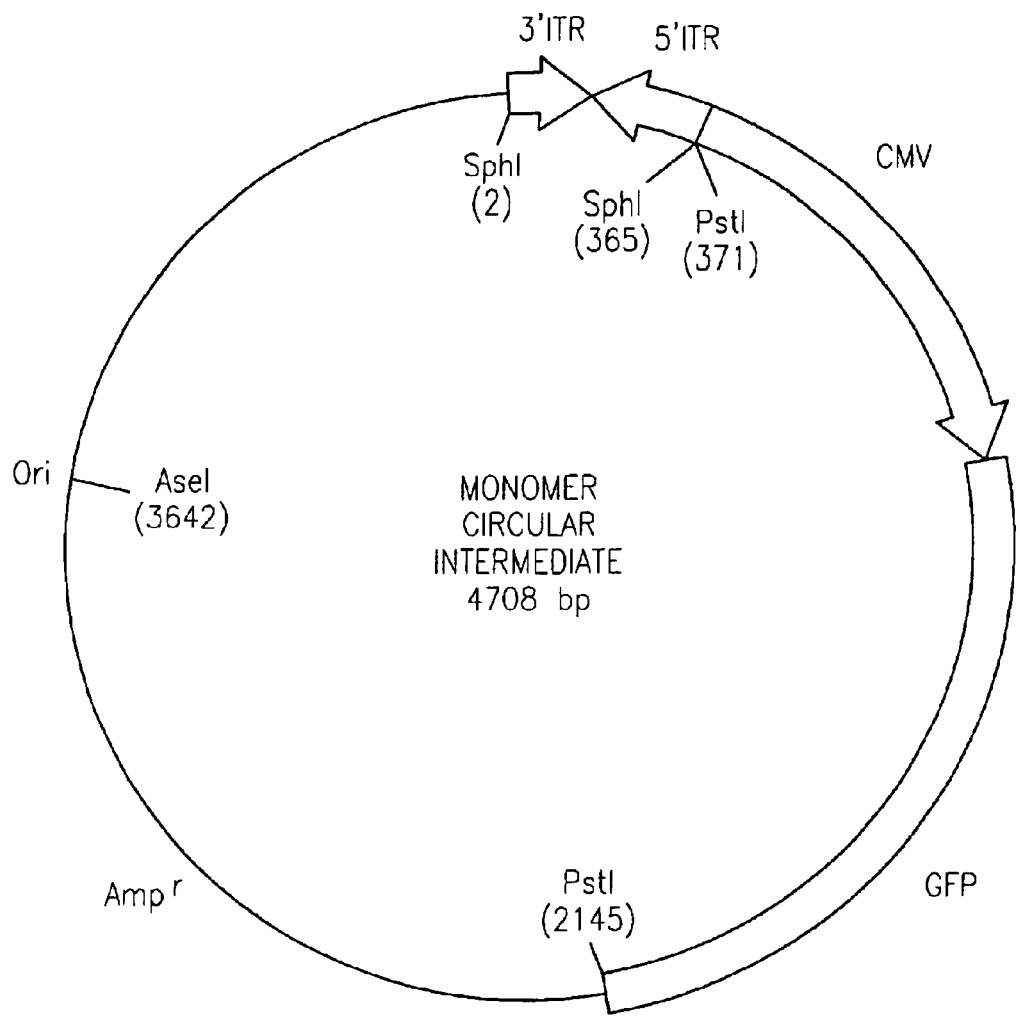
Figure 1D:
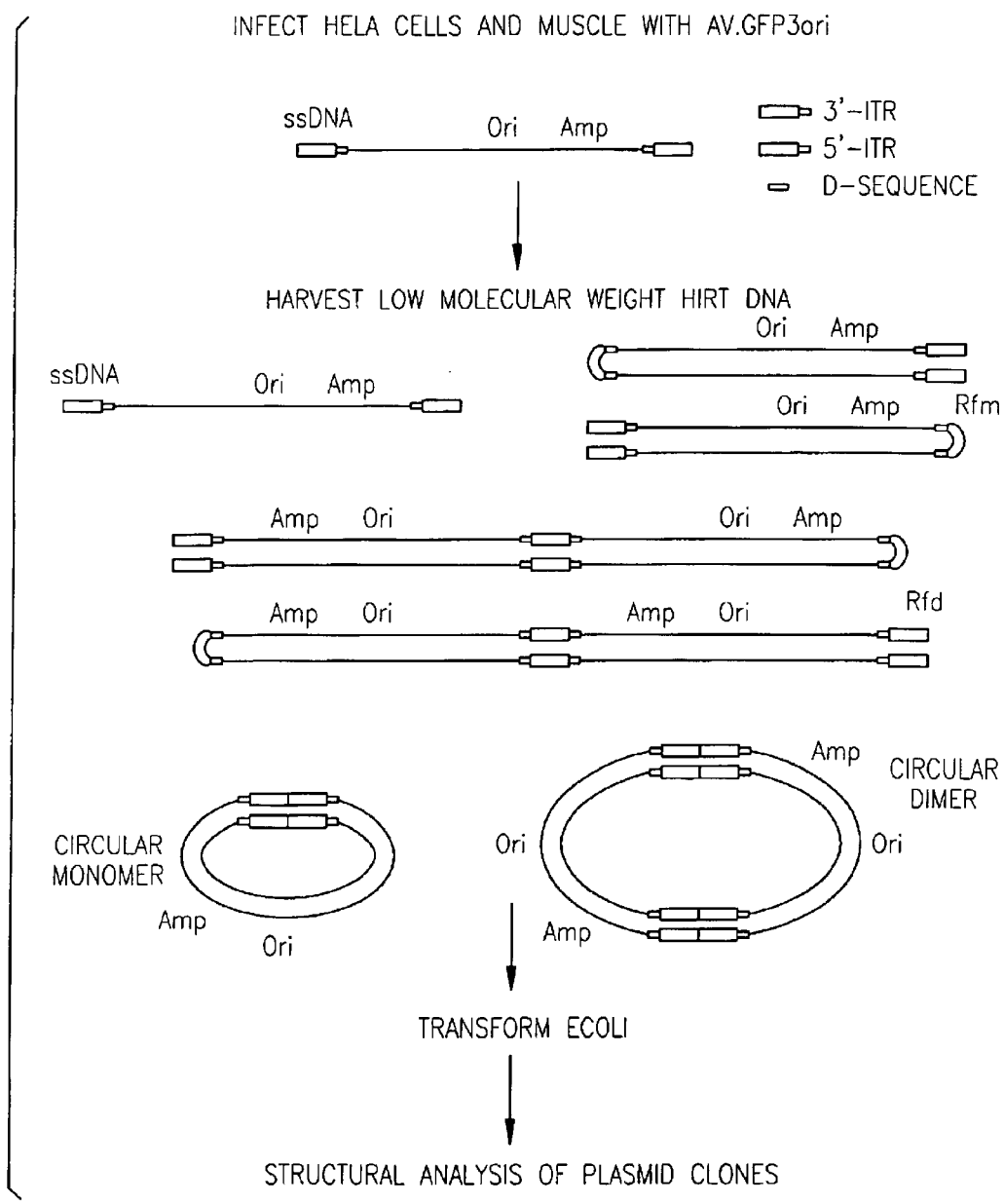
Figure 2A:
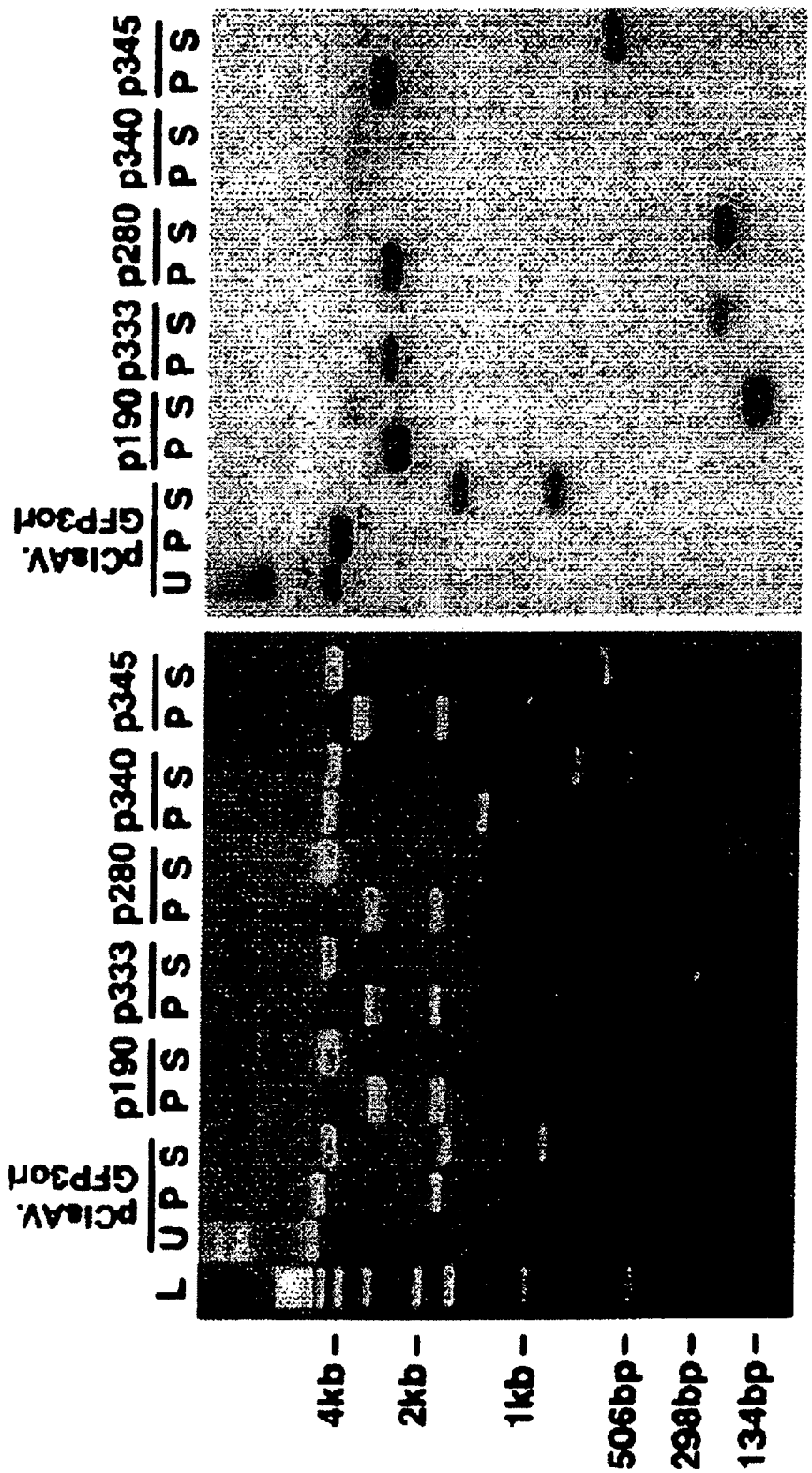
FIG. 2(Parts A–E). Structural analysis of rAAV circular intermediates in Hela cells (agarose gel, left; Southern blot, right). Circular rAAV intermediate clones isolated from AV.GFP3ori infected Hela cells were analyzed by diagnostic restriction digestion with AseI, SphI, and PstI together with Southern blotting against ITR, GFP, and Stuffer $^{32}$P-labeled probes. In panel A, four clones representing the diversity of intermediates found (p190, p333, p280, and p345) gave a diagnostic PstI (P) restriction pattern (3 kb and 1.7 kb bands) consistent with a circular monomer or multimer intact genome [agarose gel (Left) and Southern blot (Right)]. SphI (S) digestion demonstrated existence of a single ITR (p190), two ITRs in a head-to-tail orientation (p333 and p280), and three ITRs (p345) in isolated circular intermediates. The restriction pattern of pCisAV.GFP3ori (U; uncut, P; PstI cut, S; SphI cut) and 1 kb DNA ladder (L) are also given for comparison. One additional circular form (p340) was repetitively seen and had an unidentifiable structure which lacked intact ITR sequences. Circular concatainers were identified by partial digestion with AseI for clones p280 (dimer) and p333 (monomer) as is shown in Panel B. Sequence analysis (Panels C–E) of six clones (SEQ ID NOs:8–13, respectively) with identical restriction patterns to p333 (Panel A) was performed using primers (indicated by arrows; SEQ ID NOs:1–2) juxtaposed to the partial p5 promoter (dotted line) and ITRs (solid line) (SEQ ID NO:14). The top sequence (SEQ ID NO:3) represents the proposed head-to-tail structure of intact ITR arrays with alignment of sequence derived from individual clones. The junction of the inverted ITRs is marked by inverted arrowheads (at 251 bp). Several consistent bp changes (shaded) were noted in the 5' ITR D-sequence (boxed) within four clones (p79, p81, p87, and p88). All bp changes are indicated in lower case letters.

The predominant circular form isolated after transduction of Hela cells with AV.GFP3ori consisted of 4.7 kb monomer-sized molecules (FIG. 1C). SphI digestions of these circular intermediates yielded characteristic 300 bp bands which hybridized to an ITR probe on Southern blots (FIG. 2A). PstI, SphI, AseI single and double digests together with Southern blot analysis using GFP, Stuffer (data not shown), and ITR (FIG. 2A) probes confirmed the structure of the circular intermediates as head-to-tail monomer genomes (FIG. 1C). In particular, PstI digests together with ITR Southern blots distinguish these head-to-tail circular intermediates from head-to-head or tail-to-tail circular dimers. Similar results obtained with studies on AV.GFP3ori infected 293 cells and primary fibroblasts have confirmed that monomer head-to-tail circular intermediates were also the most abundant form in these cell types.

Because the predicted molecular weight of an intact head-to-tail ITR SphI fragment would be approximately 360 bp, an anomalous migration in agarose gels might be due to the high secondary structure of inverted repeats within ITRs. To this end, the head-to-tail orientation of the ITRs, as predicted by Southern blot analysis, was confirmed using several sequencing strategies. First, the SphI ITR hybridizing fragment of a circular intermediates was subcloned into a secondary plasmid vector and sequenced with primers outside the ITR cloned sequences. These findings confirmed the head-to-tail orientation of ITRs. Additionally, sequence was obtained directly from six monomer circular intermediate clones using primers internal to both the 5' and 3' ITRs (FIG. 2C). In these studies, circular intermediates were digested with SmaI and the linear 4.6 kb plasmid was gel isolated prior to sequencing. SmaI digestion (which relaxed the secondary structure of ITRs) was necessary to obtain sequence information within the ITRs. The sequencing results presented in FIG. 2C confirmed the orientation of head-to-tail ITR arrays in these intermediates.

Interestingly, sequencing also revealed several consistent base pair (bp) changes in four of the six clones analyzed (FIG. 2C). These four clones (p79, p81, p87, and p88) had consistent two bp changes within the D-sequence [G->A (122 bp) and A->G (125 bp)], which always occurred together with the bp alterations in the p5 promoter [A->G (114 bp) and A->C (115 bp)]. No other consistent bp changes were noted except for two clones (p79 and p88) which demonstrated mutations just outside the 3'ITR D-sequence [T->G (381 bp) and T->C (383 bp)].

Figure 2B:
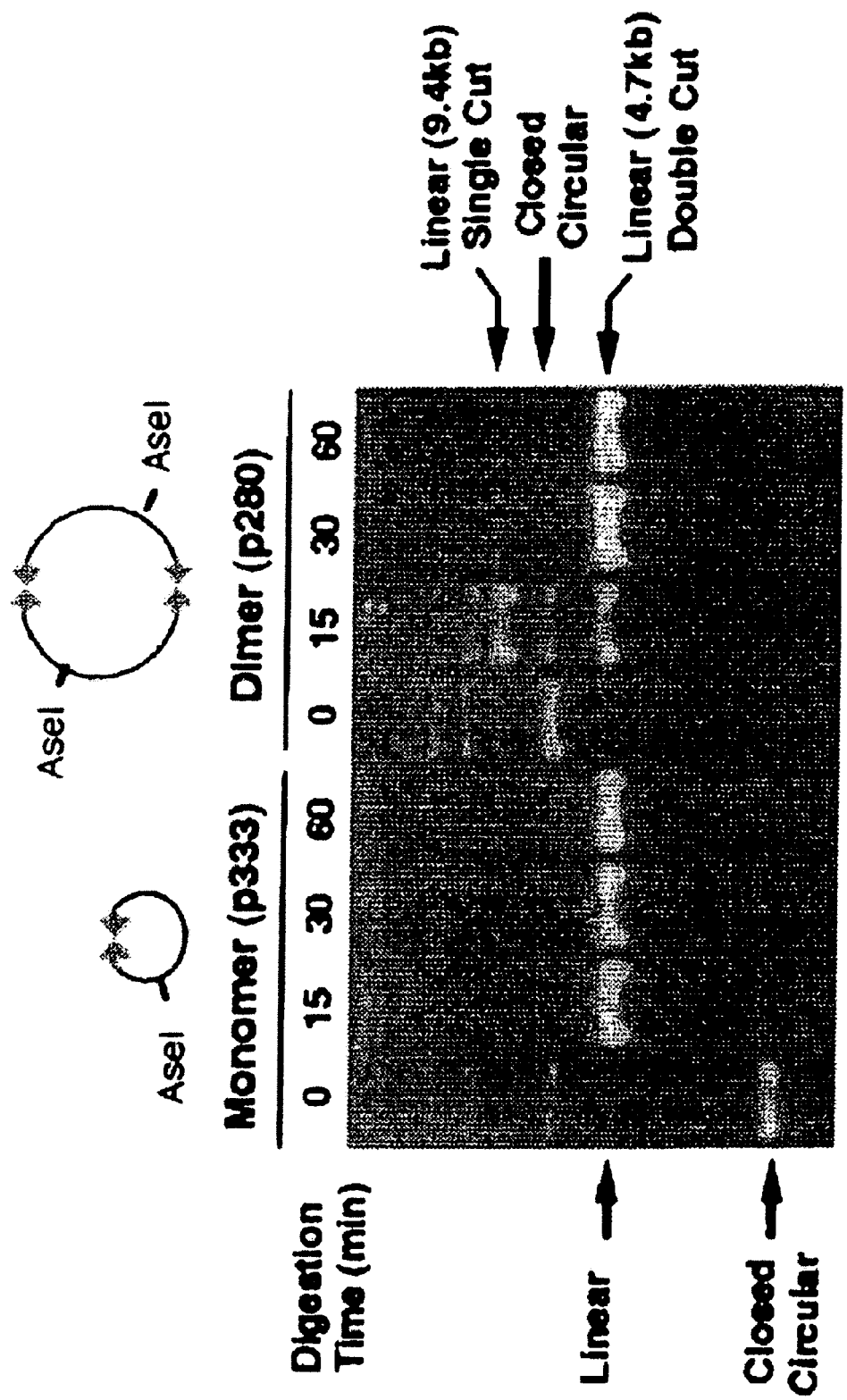

Although head-to-tail circular intermediates were the most abundant forms present in Hirt DNA from rAAV infected Hela cells, several less frequent structures were also detected. These included monomer circularized AAV genomes with one (p 190) and three ITRs (p345) arranged in a head-to-tail fashion as well as several clones with an unknown structure lacking complete ITRs (p340) (FIG. 2A). Such diversity within the ITR array may represent homologous recombination in vivo or in bacteria during amplification. However, previous studies demonstrating similar variations in ITR sequences of head-to-tail integrated genomes, suggest that such changes in the length of the ITR array may occur in vivo (Duan et al., 1997) Additionally, less frequent head-to-tail circularized multimer forms were predicted based on the variation in migration patterns of uncut plasmids which gave identical restriction patterns. Results shown in FIG. 2B confirmed the existence of monomer and dimer head-to-tail circular intermediates using partial digestion with an enzyme which cuts once in the AAV genome (AseI). Cumulative analysis of greater than 200 independently isolated circular intermediates from Hela cells demonstrated that head-to-tail circular AAV genomes occurred in greatest abundance as monomers (92%) and less frequently as multimers of greater than one genome (8%).

To establish that head-to-tail circular intermediates were formed in vivo and not by non-specific bacterial recombination of linear AAV genomes present in the Hirt DNA, a set of reconstitution experiments was performed by which the same number of rAAV particles used for infection experiments were spiked into Hela cell lysates prior to Hirt preparations. In these studies, background bacterial amplification of Hirt DNA spiked with linear rAAV genomes was negligible (FIG. 3D) and of the few isolated colonies obtained from these controls, none had a predicted head-to-tail structure as assessed by Southern blot restriction enzyme analysis (FIG. 3E). Additionally, reconstitution experiments transforming bacterial with linearized dsDNA AAV genomes did not give rise to significant levels of replication competent plasmids or the characteristic head-to-tail structure associated with AAV circular intermediates. These findings confirm that circular intermediates do not likely arise from non-specific recombination or ligation events with either ssDNA or dsDNA linear AAV genomes in bacteria. Additional control experiments, demonstrating the lack of stuffer hybridizing sequences in AAV circular intermediates by Southern blotting, also confirm that these structures do not arise from contamination of viral stocks with pCisAV.GFP3ori plasmid.

The Formation of Head-to-tail Circular AAV Intermediates is Augmented by Superinfection with E1-deleted Adenovirus.

Many aspects of the wtAAV growth cycle are affected by helper adenovirus, including AAV DNA replication, transcription, splicing, translation, and virion assembly. Such studies have provided concrete evidence that a subset of Ad early gene products provide helper functions for the wtAAV lytic cycle, including: E1a, E1b, E2a, E4 ORF6 and VA1 RNA (Muzyczka, 1992). In this regard, one of the most critical factors which is required for AAV replication is the 34 kD E4 protein (ORF6). Recent observations on the helper function of Ad in rAAV transduction have also demonstrated that Ad E4 ORF6 is essential for the augmentation of rAAV transgene expression seen with adenovirus co-infection (Ferrari et al., 1996; Fisher et al., 1996). According to these reports, the rate-limiting step enhanced by these adenoviral proteins is the conversion of single stranded AAV genomes to double stranded forms.

Studies evaluating the kinetics of rAAV circular intermediate formation demonstrated a time-dependent increase in abundance which peaked at 24 hours post-infection in Hela cells and coincided with the onset of GFP transgene expression (FIG. 3). To better understand the cellular mechanisms associated with AAV circular intermediate formation, the effects of adenoviral co-infection on this process were evaluated. The extent of transgene expression and circular intermediate formation in AV.GFP3ori infected Hela cells with or without co-infection with E1-deleted recombinant adenovirus was compared.

Figure 3C:
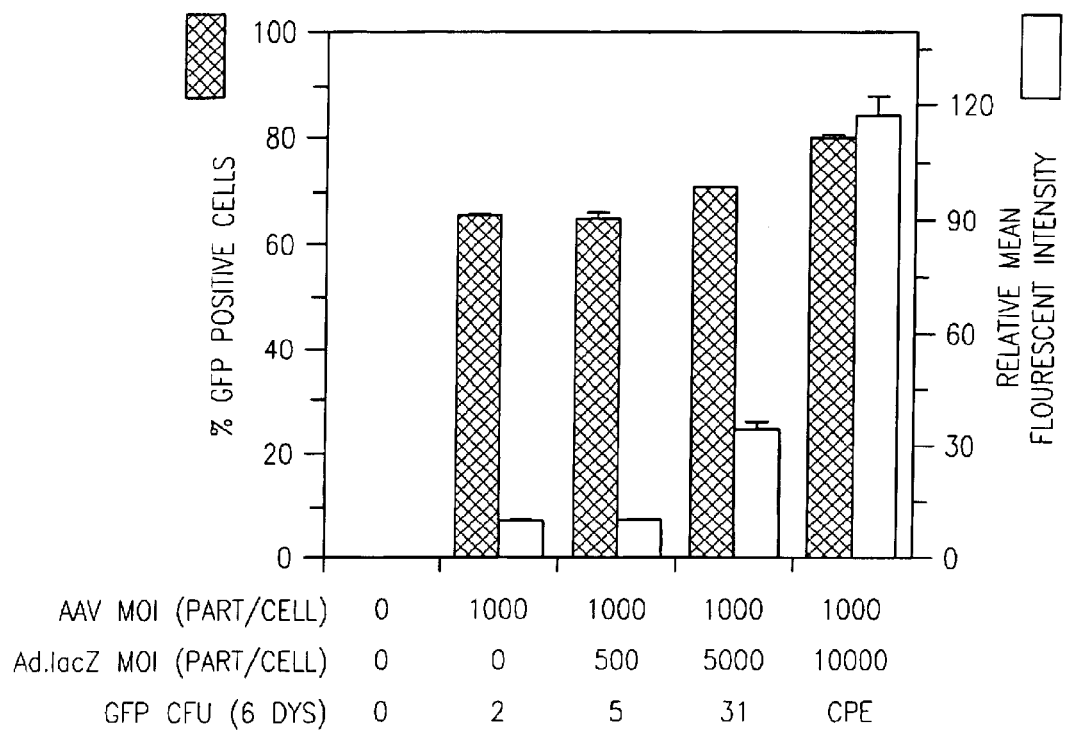
FIG. 3(Parts A–F). Adenovirus augments AAV circular intermediate formation in Hela cells. Infection of Hela cells with increasing doses (0, 500, and 5000 particles/cell) of recombinant E1-deleted adenovirus (Ad.CMVlacZ) leads to substantial expression of E2a 72 kd DNA Binding Protein, as demonstrated by indirect immunofluorescent staining for DBP at 72 hours post-infection (Panel A). Co-infection of Hela cells with Ad.CMVlacZ (5000 particles/cell) and AV.GFP3ori (1000 DNA particles/cell) led to substantial augmentation of rAAV GFP transgene expression (Panel B). Augmentation in rAAV GFP transgene expression in the presence of increasing amounts (0, 500, 5000 and 10000 particles/cell) of recombinant Ad.CMVlacZ was quantified by FACS analysis at 72 hour post-infection (Panel C). Results demonstrate the mean (+/−SEM) for two experiments performed in duplicate. In addition, an aliquot of cells was split (1:10) at the time of FACS analysis and GFP colony forming units (CFU) per 10× field were quantified at 6 days (CPE denotes significant cytopathic effects at an adenoviral MOI of 10,000 particles/cell and was not quantified for GFP colonies). Hirt DNAs from AV.GFP3ori (1000 DNA particles/cell) infected Hela cells with or without co-infection with Ad.CMVlacZ (5,000 particles/cell) were used to transform E. coli. The total number of ampicillin-resistant bacterial CFU (Panel D) and total number of head-to-tail circular intermediates CFU (Panel E) are given for a representative experiment. Greater than 20 clones for each time point were evaluated by Southern blot (see FIG. 2 for detail). Zero hour controls were performed by mixing an equivalent amount of AV.GFP3ori virus as used in experiments with mock infected cellular lysates prior to Hirt purification. Panel F depicts the abundance of head-to-tail circular intermediates as a percentage of total ampicillin-resistant bacterial CFU isolated from Hirt DNA.

Although E1-deleted adenoviruses are severely handicapped in their ability to synthesize viral gene products, at high MOIs of >5000 significant E2a protein expression was noted (FIG. 3A). As an indicator of transgene expression, the abundance and average relative intensity of GFP positive cells was determined against mock infected controls by fluorescent microscopy (FIG. 3B) and FACS analysis (FIG. 3C) at 72 hours post-infection. In accord with previous reports demonstrating augmentation in rAAV transgene expression by adenovirus (Ferrari et al., 1996; Fisher et al., 1996), the extent of GFP transgene expression was dramatically increased at doses of adenovirus which led to viral gene expression (MOI>5000; FIGS. 3A–C). Additionally, persistence of rAAV transgene expression was also augmented by co-infection with E1-deleted adenovirus, as determined by GFP-expressing colony formation following serial passages (FIG. 3C).

Figure 3D:
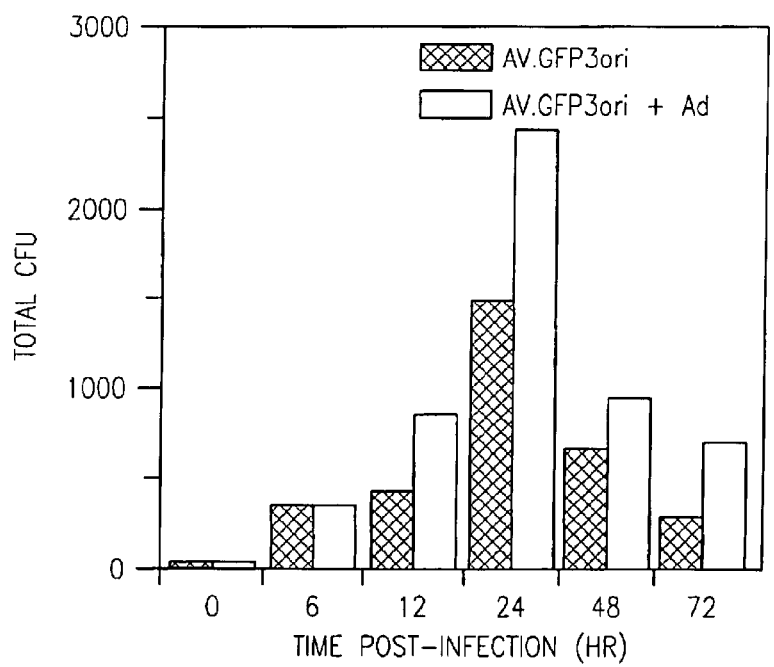
Figure 3E:
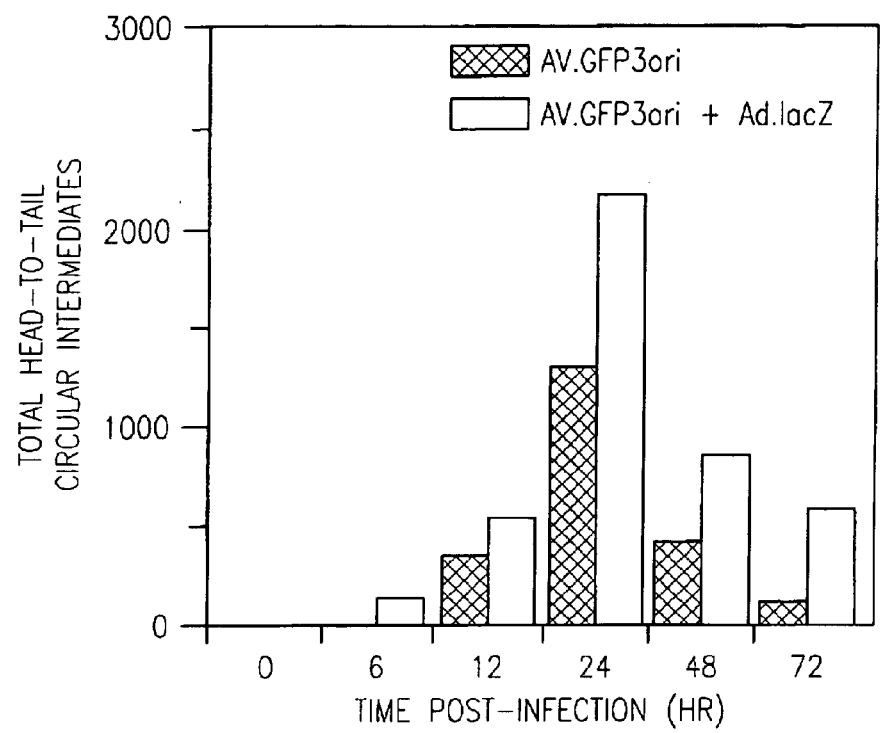

If circular intermediates represent a molecular form of rAAV important for efficient and/or persistent transgene expression, augmentation of rAAV transgene expression by adenovirus might also modulate circular intermediate formation. In these studies, the abundance and time course of AAV circular intermediate formation was evaluated following superinfection with Ad.CMVLacZ. Results from these experiments are shown in FIG. 3D, which represents the total number of bacterial colonies (per 35 mm plate) obtained following transformation of $E.\ coli$ with Hirt DNA isolated from Hela cells infected with AV.GFP3ori (1000 DNA particles/cell) with or without co-infection with Ad.CMVlacZ (5,000 particles/cell). An MOI of 5000 Ad particles/cell was chosen for these experiments since this level of adenovirus led to minimal cytopathic effect (CPE) with high levels of E2a expression.

Figure 3F:
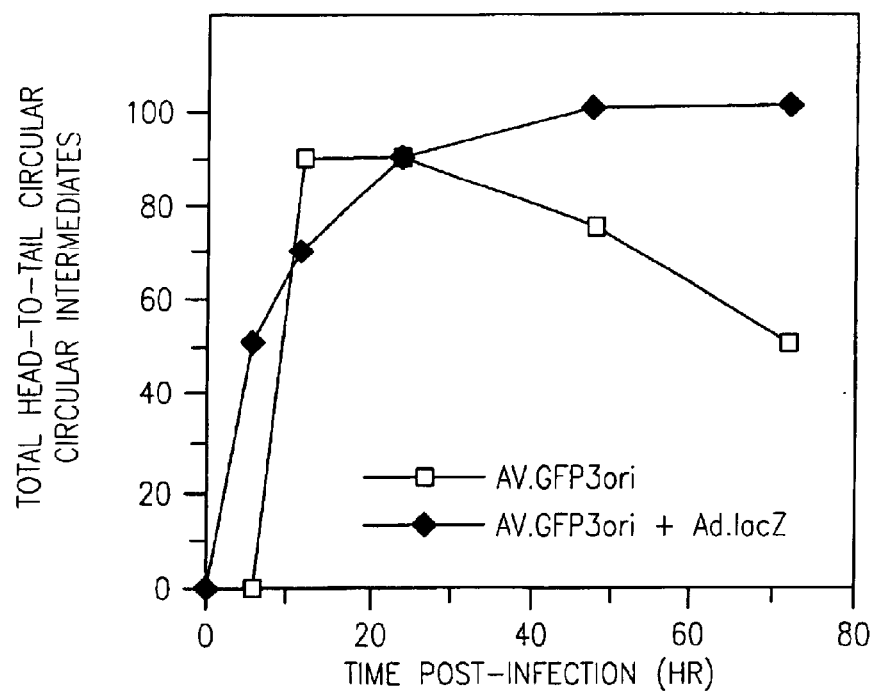

These studies demonstrated a nearly 2-fold augmentation by Ad.CMVLacZ in the total abundance of AAV rescued plasmid intermediates in $E.\ coli$ (FIG. 3D). Southern blot restriction enzyme analysis demonstrated that the predominant forms in both the presence and absence of adenovirus were head-to-tail monomer circular intermediates containing the diagnostic 300 bp ITR fragment following SphI digestion (FIG. 3E). Additionally, results demonstrated that adenovirus co-infection led to an earlier time of onset and increased stability of AAV head-to-tail monomer circular intermediates (FIGS. 3E and F). For example, at 6 hours post-infection, head-to-tail circular intermediates were only present in Hela cells co-infected with adenovirus. Furthermore, a decline in the percentage of head-to-tail circular intermediate clones was seen at 48–72 hours post-AAV infection in the absence of adenovirus. In contrast, this decline was significantly blunted by the presence of helper adenovirus (FIG. 3F). Based on these findings, it was concluded that certain adenoviral proteins produced by superinfection with E1-deleted adenovirus were capable of modulating circular intermediates formation and stability during rAAV transduction.

Discussion

In the present study, it was shown that circularization of linear AAV genomes occurs during rAAV transduction. Circularization appears to predominately occur as head-to-tail monomer genomes. However, the existence of less abundant circular multimer forms suggests that recombinational events subsequent to the initial infection may drive concatamerization of circular genomes. The diversity in the length of ITR arrays found within circular intermediates (i.e., 1–3 ITRs) also supports the notion that these forms may be highly recombinagenic. Of mechanistic interest in the formation of circular intermediates is the uniformity of mutations observed in the D-sequences and nearby p5 promoter region and the confinement of these mutations to the 5'-ITRs. Although the etiology of these base pair changes is unknown, their uniformity suggests that they may have a direct role in the formation of circular intermediates and in increased stability. Recent findings, which suggest that an endogenous host single strand D-sequence binding protein is important in rAAV transduction, lend support to the potential involvement of this sequence in circular intermediate formation (Wang et al., 1997; Qing et al., 1998). Furthermore, it remains to be determined whether the in vivo formation of AAV circular intermediates occurs through the circularization of single or double stranded AAV genomes.

By analogy, retroviral transduction intermediates have striking similarities to the current findings with AAV. Three DNA forms have been isolated following retroviral infection, including linear DNA with long terminal repeats (LTRs) at both ends, circular DNA with one LTR, and circular DNA with multiple LTRs (Panganiban, 1985). Although it is disputed which of these forms are the direct precursor to integration, the existence of circular retroviral genomes which also have similar repeat regions at the ends of their genomes suggests the potential for common mechanisms with the formation of AAV circular intermediates. These AAV circular intermediates could act as integration precursors and/or stable episomal genomes.

The head-to-tail ITR structures found in AAV circular intermediates are most characteristic of latent integrated AAV genomes. In contrast, lytic phases of AAV growth are typically associated with head-to-head and tail-to-tail replication form genomes. Hence, it is likely that circular intermediates represent a latent aspect of the AAV life cycle. The finding that co-infection with adenovirus leads to increased abundance and stability of AAV circular intermediates suggests a novel link between adenoviral helper functions and latent infection of AAV.

Aspects of inverted head-to-tail ITRs, which include palindromic hairpins similar in structure to "Holliday-like" junctions, might impart recombinagenic activity which aids in viral integration. Such Holliday junctions have been shown to play critical roles in directing homologous recombination in bacteria through the processing of recombination intermediates by RuvABC proteins (West, 1997; Lee et al., 1998). Interestingly, a mammalian endonuclease, analogous to bacterial RuvC resolvase, has also been isolated from cell lines (Hyde et al., 1994). Despite the theoretical considerations which might suggest that circular AAV genomes have characteristics of preintegration intermediates, a study with recombinant retrovirus has demonstrated that palindromic LTR-LTR junctions of MMLV are not efficient substrates for proviral integration (Lobel et al., 1989). Nonetheless, circular AAV genomes have been previously proposed as integration intermediates based on proviral structure (Linden et al., 1996).

EXAMPLE 2

Methods

Production of rAAV Shuttle Vector.

The cis-acting plasmid (pCisAV.GFP3ori) used for rAAV production was generated by subcloning the Bsp1201/Not I fragment (743 bp) of the GFP transgene from pEGFP-1 (Clontech) between the CMV enhancer/promoter and SV40polyA by blunt-end ligation. A 2.5 kb cassette containing beta-lactamase and bacterial replication origin from pUC19 was blunt ligated down-stream of GFP reporter cassette. The ITR elements were derived from pSub201.2 The entire plasmid contains a 4.7 kb AAV component flanked by a 2 kb stuffer sequence. The integrity of ITR sequences was confirmed by restriction analysis with SmaI and PvuII, and by direct sequencing using a modified di-deoxy procedure which allowed for complete sequence through both 5' and 3' ITRs. Recombinant AAV stocks were generated by co-transfection of pCisAV.GFP3ori and pRep/Cap together with co-infection of recombinant Ad.CMVlacZ in 293 cells. The rAV.GFP3ori virus was subsequently purified through 3 rounds of CsCl banding as described in Duan et al., 1997. The typical yields from this viral preparation were 1012 DNA molecules/ml.

DNA titers were determined by viral DNA slot blot hybridization against GFP $^{32}$P-labeled probe with copy number plasmid standards. The absence of helper adenovirus was confirmed by histochemical staining of rAAV infected 293 cells for beta-galactosidase, and no recombinant adenovirus was found in $10^{10}$ particles of purified rAAV stocks. The absence of significant wtAAV contamination was confirmed by immunocytochemical staining of rAAV/Ad co-infected 293 cells with anti-Rep antibodies. Transfection with pRep/Cap was used to confirm the specificity of immunocytochemical staining. No immunoreactive Rep staining was observed in 293 cells infected with $10^{10}$ rAAV particles.

Isolation of AAV Circular Intermediates from Muscle.

The tibialis anterior muscle of 4–5 week old C57BL/6 mice were infected with AV.GFP3ori ($3\times10^{10}$ particles) in Hepes buffered saline (30 μl). GFP expression was analyzed by direct immunofluorescence of freshly excised tissues and/or in formalin-fixed cryopreserved tissue sections in four independently injected muscles harvested at 0, 5, 10, 16, 22 and 80 days post-infection. Tissue sections were counter-stained with propidium iodide to identify nuclear DNA. Hirt DNA (Hirt, 1967) (20 ml per muscle sample) was isolated from at least three independent muscle specimen for each time point and used to transform E. coli SURE cells using 3 ml of Hirt with 40 ml of electrocompetent bacterial (approximately $1\times10^9$ cfu/ug DNA, Strategene Inc.). The resultant total number of bacterial colonies was quantified for each time point and the abundance of head-to-tail circular intermediates was evaluated for each time point (>20 bacterial clones analyzed) by PstI, AseI, SphI, and PstI/AseI digestion, and confirmed by Southern blot analysis using ITR, GFP and stuffer probes. The head-to-tail confiruration in typical clones were also confirmed by dideoxy sequencing using primers EL118 (5'-CGGGGGTCGTTGGGCGGTCA-3'; SEQ ID NO:1) and EL230 (5'-GGGCGGAGCCTATGGAAAA-3'; SEQ ID NO:2) which are nested to 5' and 3' ITR sequences, respectively. Zero hour controls were generated by mixing $3\times10^{10}$ particles of AV.GFP3ori with control uninfected muscle lysates prior to Hirt DNA preparation. As described in Table 1, a number of additional controls for were performed to rule out non-specific recombination of linear AAV genomes in bacteria as a source for isolated circular intermediates.

TABLE 1

Control Experiments for Rescue of Circular Intermediates in Bacteria

| Type of Input DNA | Source of DNA | Number of Molecules | Number of Amp Resistant Bacterial Colonies | Presence of Head-to-Tail Circular Intermediates[e] |
|---|---|---|---|---|
| Purified rAVV | Hirt from Infected Muscle (22 day) | $3 \times 10^{10}$ | approximately $5 \times 10^3$ | Yes |
| Purified rAAV | Virus re-constituted into Un-infected Muscle Hirt[a] | $3 \times 10^{10}$ | 0 | No |
| Linear ssDNA Encompassing rAAV Genome[b] | Isolated from Purified Virus | $3 \times 10^{10}$ | 2 | No |
| Linear dsDNA Encompassing Entire rAAV Genome | Isolated from proviral plasmid (HindIII/PvuII)[c] | $3 \times 10^{10}$ | 3 | No |
| Linear dsDNA Encompassing Entire rAAV Genome + ligased[d] | Isolated from proviral plasmid (HindIII/PvuII) | $3 \times 10^{10}$ | $>6 \times 10^3$ | Yes |

[a]Purified virus was reconstituted into muscle homogenates prior to preparation of Hirt DNA.
[b]Viral DNA predominantly contained single stranded genomes as evident by Southern blot analysis against with ITR probe. However, small amount of dsDNA AAV genomes also existed and are likely due to reannealing of single stranded genomes during preparation. Purified viral DNA concentrations were determined by $OD_{260}$ and 75 ng representing approximately 3 × $10^{10}$ viral genomes were used for transformation of bacteria.
[c]HindIII/PvuII digestion was used to remove the entire rAAV genome from pcisAV.GFP3ori. HindIII and PvuII leave 10 and 0 bps of flanking sequence outside the 5' and 3' ITRs, respectively. The linear dsDNA fragment (4.7 kb) was gel isolated following blunting with T4 DNA polymerase and the DNA concentration determined by $OD_{260}$. One hundred and fifty ng of linear fragment representing approximately 3 × $10^{10}$ viral genomes were used for transformation of bacteria.
[d]Linear dsDNA viral genomes (HindIII/PvuII blunted fragment) were treated with T4 DNA ligase prior to transformation of bacteria.
[e]The presence of head-to-tail circular AAV intermediates were confirmed by restriction enzyme digestion (AseI, PstI, and SphI) and Southern blotting against ITR probe.

Fractionation of Muscle Hirt DNA Preparations.

Preparative-scale fractionation of the muscle Hirt DNA was performed by 1% agarose gel electrophoresis using the Bio-Rad Mini Prep Cell (Catalog #170-2908). A 4.5 ml (10.5 cm) tubular gel containing 1× TBE buffer was poured according to manufacturer's specification. A total of 20 ml Hirt preparation from one entire muscle sample was loaded on top of the gel. Electrophoresis was carried out at a constant current of 10 mA over a period of 5 hours. Sample eluent was drawn from the preparative gel apparatus by a peristaltic pump at a rate of 100 ml/min and eluted into a fraction collector at 250 ml/fraction. The collected DNA was subsequently concentrated by standard ethanol precipitation and used to transform SURE bacterial cells by electroporation as described above.

In vitro Persistence of AAV Circular Intermediates.

Transgene expression and persistence of AAV circular intermediate plasmid clones were evaluated following transient transfection in Hela and 293 cells. Subconfluent monolayers of Hela cells in 24-well dishes were transfected with 0.5 mg of either AAV circular intermediates (p81 or p87) or pCMVGFP using Lipofectamine (Gibco BRL Inc.). The cultures were then incubated for 5 hours in serum free DMEM followed by incubation in DMEM supplemented with 10% fetal bovine serum. All plasmid DNA samples used for transfections were spiked with pRSVlacZ (0.5 mg) as an internal control for transfection efficiency. At 48 hours post-transfection, cells were passaged at a 1:10 dilution and allowed to grow to confluency (day 5), at which time GFP clones were quantified for size and abundance using direct fluorescent microscopy. The percent of beta-galactosidase-expressing cells was also quantified at this time point by X-gal staining. At 5 days, cells were passaged an additional time (1:15 dilution) GFP clones were quantified again at day 10. The persistence of plasmid DNA at passage-5, 7, and 10 days post-transfection was evaluated by Southern blot analysis of total cellular DNA using $^{32}$P-labeled GFP probes. To determine whether the head-to-tail ITR array within circular intermediates was responsible for increases in the persistence of GFP expression, the head-to-tail ITR DNA element was subcloned into the pGL3 luciferase plasmid to generate pGL3(ITR). The head-to-tail ITR DNA element was isolated from a monomer circular intermediate (p81) by AatII and HaeII double digestion and subsequently inserted into the SalI site of pGL3 (Promega) by blunt ligation. The resultant plasmid pGL3(ITR) contains the luciferase reporter and head-to-tail ITR element 3' to the polyA site. The integrity of the ITR DNA element within this plasmid was confirmed by sequencing. The persistence of transgene expression from pGL3(ITR) was compared to that of pGL3 by luciferase assays on transiently transfected Hela cells as described above and analyzed at 10 days (passage-2). Transfection efficiencies were normalized using a dual renilla luciferase reporter vector (pRLSV40, Promega).

Results

AAV Circular Intermediates Represent Stable Episomal Forms of Viral DNA Associated with Long-term Persistence of Transgene Expression in Muscle.

Figure 4A:
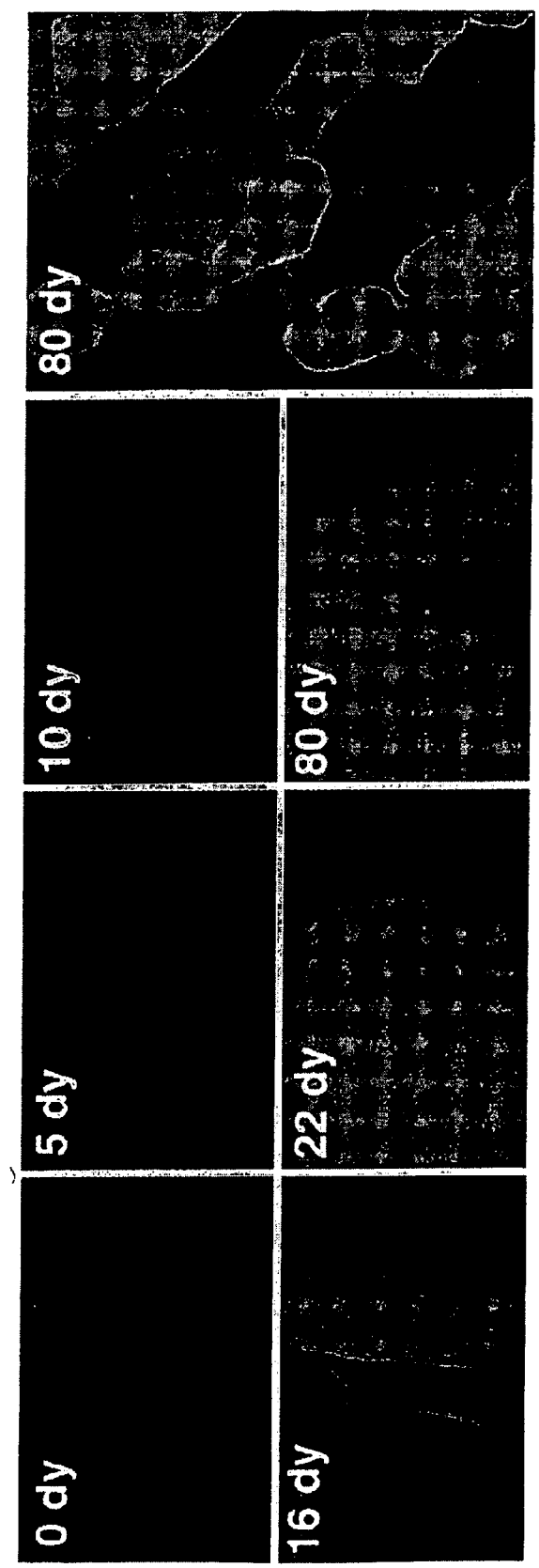
FIG. 4(Parts A–C). Formation of rAAV head-to-tail circular intermediates following in vivo transduction of muscle. The tibialis anterior muscle of 4–5 week old C57BL/6 mice were infected with AV.GFP3ori (3×10¹⁰ particles) in HEPES buffered saline (30 μl). GFP expression (Panel A) was analyzed by direct immunofluorescence of freshly excised tissues and/or in formalin-fixed cryopreserved tissue sections in four independently injected muscles harvested at 0, 5, 10, 16, 22 and 80 days post-infection. GFP expression was detected at low levels beginning at 10 days and was maximum at 22 days post-infection. Expression remained stable to 80 days at which time greater than 50% of the tissue was positive (see 80 day tissue cross section counter stained with propidium iodide, panel A). Hirt DNA was isolated from muscle samples at each of the various time points and after points was used to transform E. coli. Rescued plasmids (p439, p16, p17) were analyzed by Southern blotting in Panel B showing an agarose gel on left and ITR probed blot on right. U:uncut, P:PstI cut, and S:SphI cut. The schematic drawing of the most predominant type of head-to-tail circular AAV intermediate plasmids rescued from bacteria is given in the right of Panel B and shows the structure of p17 as an example. Other typical clones included those with less than two ITRs as shown for p16. SphI digestion of p16 and p17 plasmids released ITR hybridizing fragments of approximately 140 and 300 bp, respectively. The slightly lower mobility then predicted for these ITR fragments likely represents anomalous migration due to the high secondary structure of inverted repeats within ITRs. Sequence analysis of p17 and p16 using nested primers to 5' and 3'-ITRs also confirmed the ITR orientations shown to the right of the gel. Additional restriction enzyme analyses to determine this structure included double and single digests with SphI, PstI, AseI, and/or SmaI. An example of an atypical clone (p439) rescued from bacteria with unknown structure is also shown.

To evaluate the molecular characteristics of rAAV genomes in muscle, a rAAV shuttle viral vector (AV.GFP3ori) was utilized which harbors an ampicillin resistance gene, bacterial origin of replication, and GFP reporter gene (FIG. 1A). This recombinant virus was used to evaluate the presence of circular intermediates by bacterial rescue of replication competent plasmids. In these studies, delivery of AV.GFP3ori (3×10¹⁰ particles) to the tibialis muscle of mice led to GFP transgene expression which peaked at 22 days and remained stable for at least 80 days (FIG. 4A). These results confirmed previous successes in rAAV mediated gene transfer to muscle (Kessler et al., 1996; Herzog et al., 1997; Xiao et al., 1996; Clark et al., 1997; Fisher et al., 1997). The formation of circular intermediates was evaluated by E. coli transformation of Hirt DNA harvested from muscle at 0, 5, 10, 16, 22, and 80 days post-infection with AV.GFP3ori.

Figure 4B:
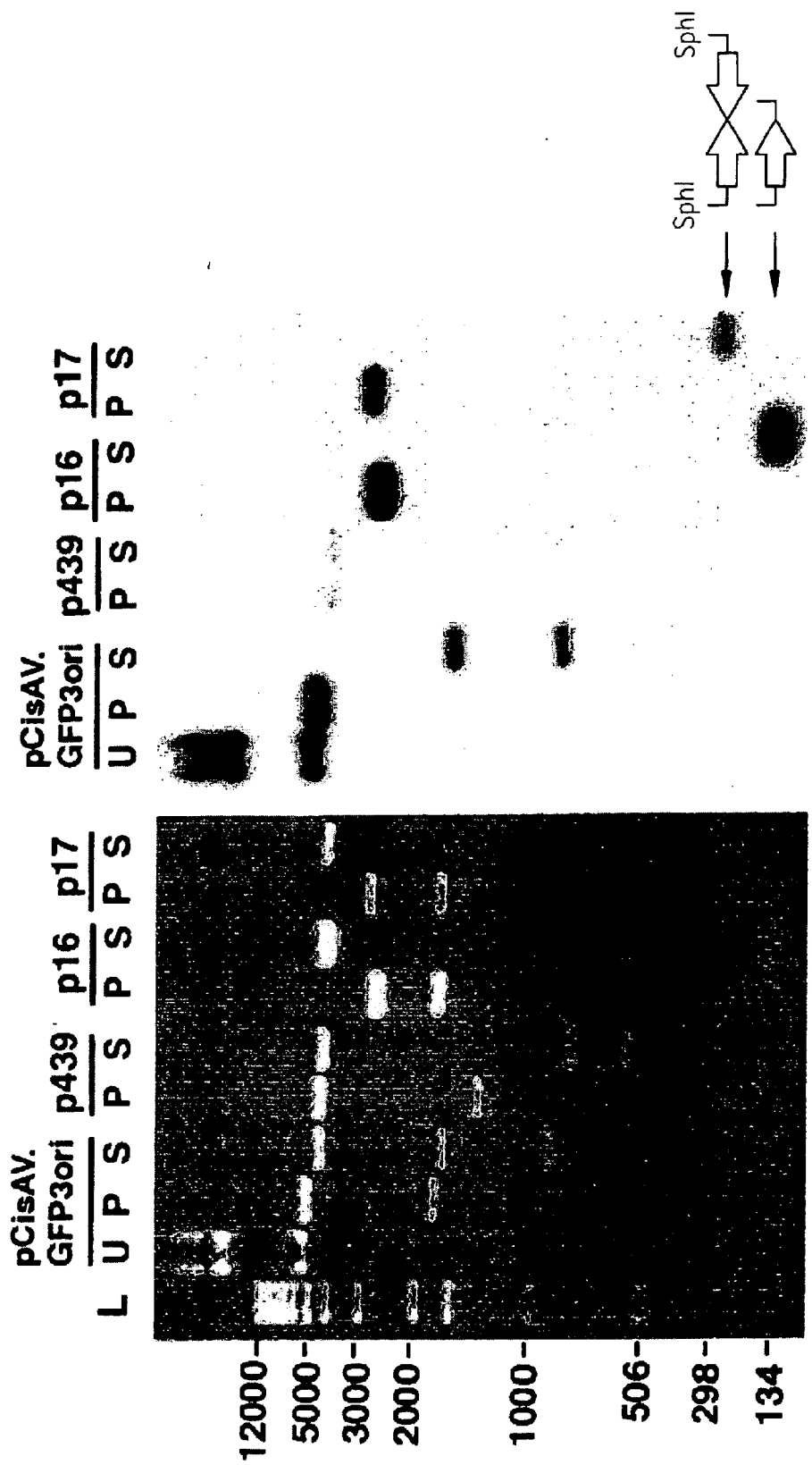
Figure 4C:
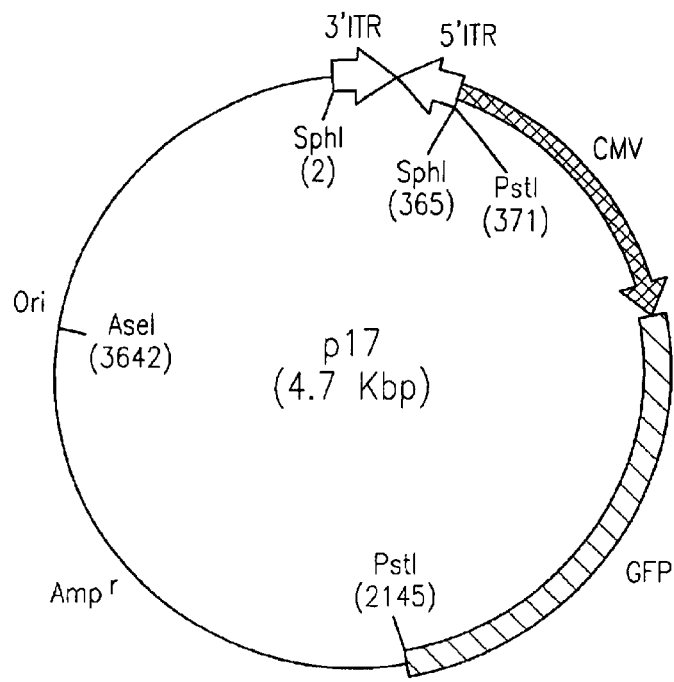
Figure 5A:
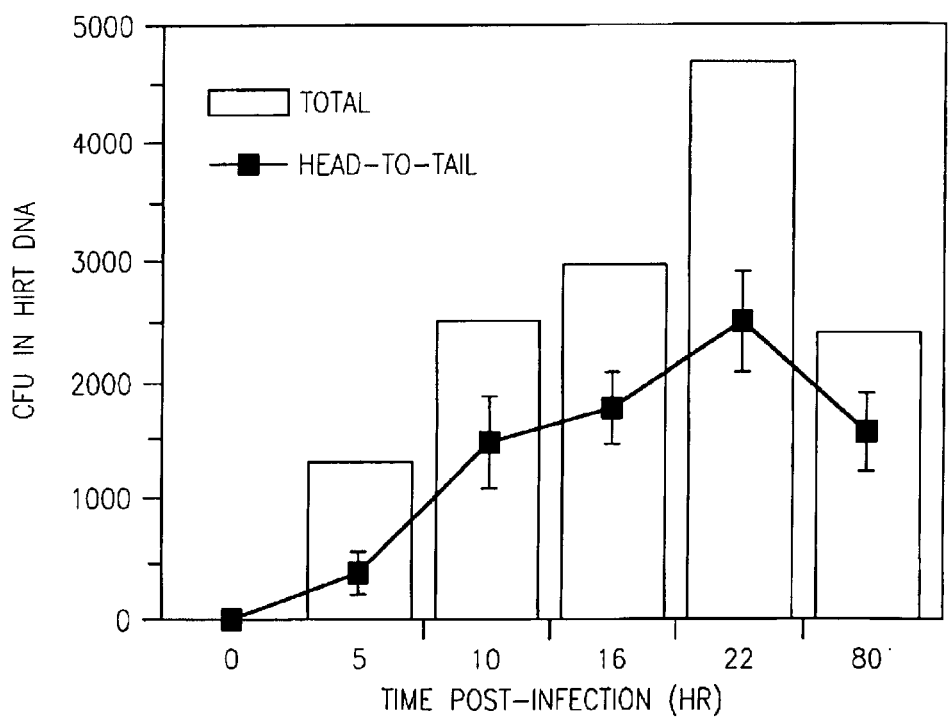
FIG. 5(Parts A–C). Frequency of circular intermediate formation in muscle following transduction with rAAV. Hirt DNAs isolated from rAAV infected tibialis muscle were used to transform E. coli and the rescued plasmids analyzed by Southern blotting (greater than 20 clones were analyzed from at least two independent muscle samples for each time point). The averages of total head-to-tail circular intermediate clones (line) and ampicillin resistant bacterial clones (bar) isolated from each tibialis anterior muscle at 0, 5, 10, 16, 22 and 80 days post-infection are summarized in Panel A. Only plasmids which contained 1–2 ITRs were included in the estimation of total head-to-tail circular intermediates. Plasmids which demonstrated an absence of ITR hybridizing SphI fragments (between 150 to 300 bp) were omitted from the calculations. Panel B demonstrates the diversity of ITR arrays found in head-to-tail circular intermediates at 80 days post-infection. This panel depicts a Southern blot probed with ITR sequences and represents circular intermediates with 1–3 ITRs. SphI fragments which hybridize to ITR probes indicate the size of inverted ITR arrays (marked by arrows to right of gel). Additional restriction enzyme analysis was used to determine the structure of monomer and multimer circular intermediates. Examples are shown for two multimer (p136 and p143) circular intermediates which contain approximately three AAV genomes. Undigested plasmids of p136 and p143 migrate greater than 12 kb and is contrasted to the most predominant form of head-to-tail undigested circular intermediates at 22 days which migrate at 2.5 kb. The digestion pattern of p136 is consistent with a uniform head-to-tail configuration of three genomes which is indistinguishable from digestion patterns of p139 which contains one circularized genome (undigested p139 migrates at 2.5 kb, data not shown, also see examples p17 in FIG. 4). In contrast, p136 depicts a more complex head-to-tail multimer circular intermediate which has various deletions and duplications within the ITR arrays. Predicted structure of five representative intermediates is schematically shown in Panel C.
Figure 5B:
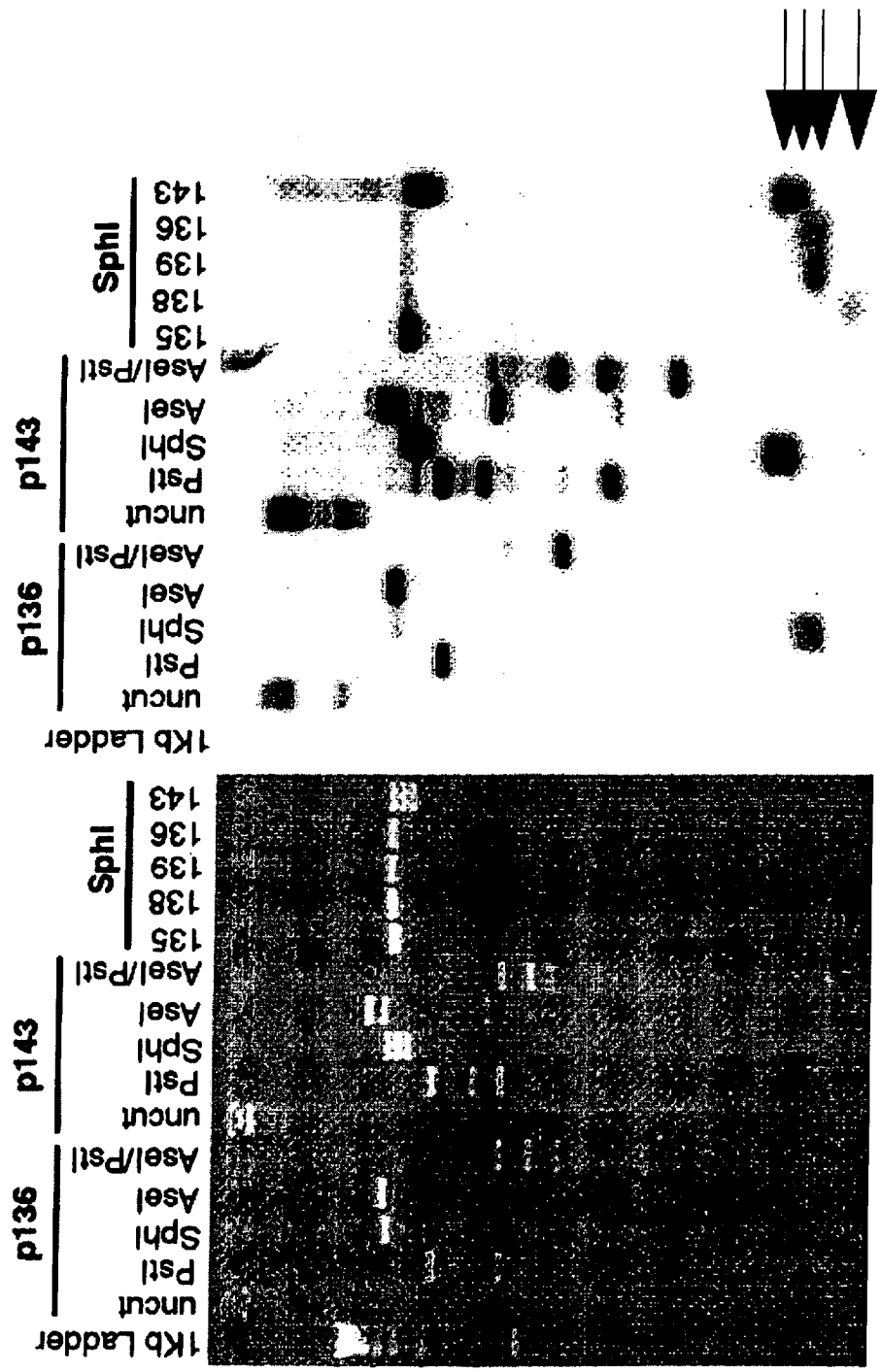
Figure 5C:
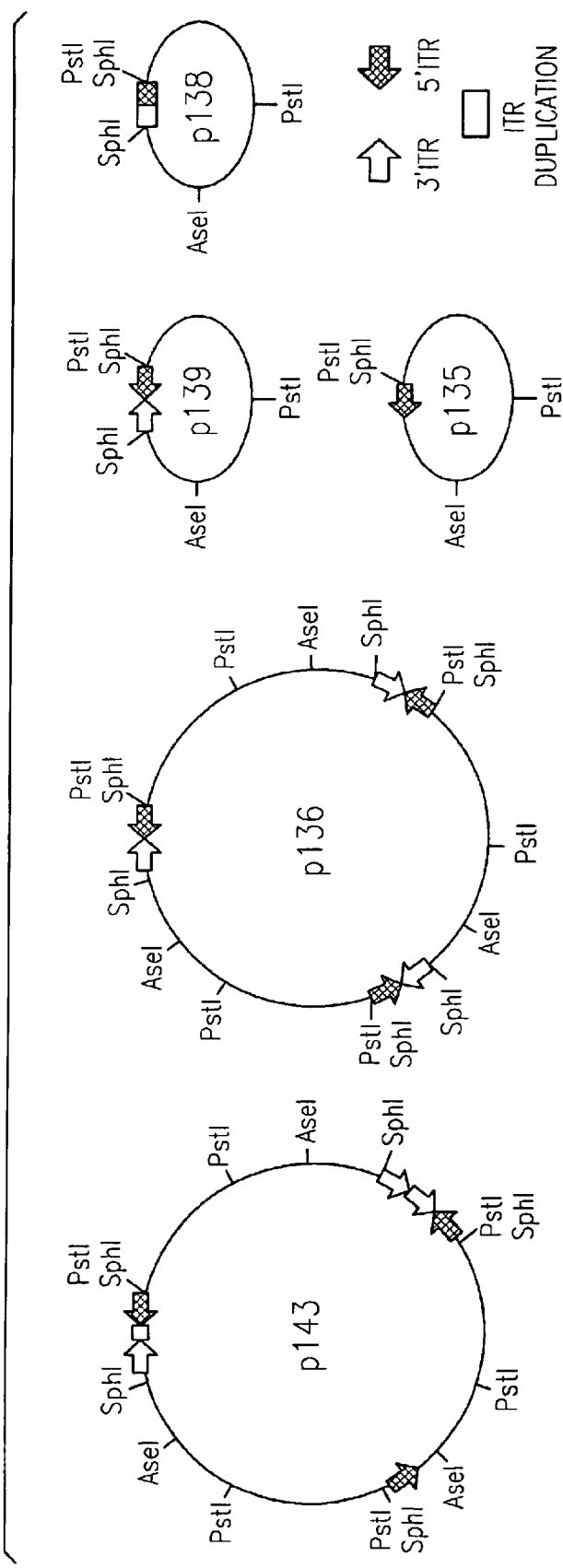

In these muscle samples, circular intermediates were found to have a characteristic head-to-tail structure with 1-2 ITR repeats. The most abundant form included two inverted ITRs within a circularized genome (FIG. 4B, clone p17). This figure also depicts a less frequent form (<5%) of circular intermediates observed, p439, with undetermined structure. When this type of replication competent plasmid was seen, it was not included in the quantification of head-to-tail circular intermediates since its structure could not be conclusively determined. The total abundance of muscle Hirt derived head-to-tail circular intermediates (with 1-2 ITRs) demonstrated a time-dependent increase that peaked with transgene expression at 22 days and slightly decreased by day 80 (FIG. 5A). Increased diversity in the length of ITR arrays within circular intermediates was seen at longer time points. For example, FIG. 5B demonstrates several isolated circular intermediates with 1-3 ITRs isolated from 80 days muscle Hirt samples. This is in contrast to the more uniform structure of circular intermediates with two ITRs in a head-to-tail conformation at 5-22 days post-infection.

To evaluate the potential for artifactual rescue of linear rAAV genomes by recombination in bacteria, several control experiments were performed. First, uninfected control muscle Hirt preparations, spiked with an equal amount of rAAV virus used for in vivo infection of muscles, failed to give rise to replicating plasmids following transformation of E.coli. Second, when a blunted linear double stranded HindIII/PvuII fragment isolated from pcisAV.GFP3ori (encompassing the entire rAAV genome) was used to transform bacteria, no ampicillin resistant bacterial colonies were obtained. The addition of T4 ligase to this fragment, however, led to significant numbers of bacterial colonies. Third, when purified single stranded rAAV DNA was used for transformation, no bacterial colonies were obtained. As summarized in Table 1, these results confirm that in the absence of productive infection, rAAV genomes themselves are incapable of recombining into replication competent plasmids in bacteria. Hence, in vivo circularization of rAAV genomes is a prerequisite for rescuing autonomously replicating plasmids in E. coli with this shuttle vector.

Molecular Weight of Circular Intermediates Suggest a Conversion from Monomer to Multimer Forms Over Time.

Figure 6:
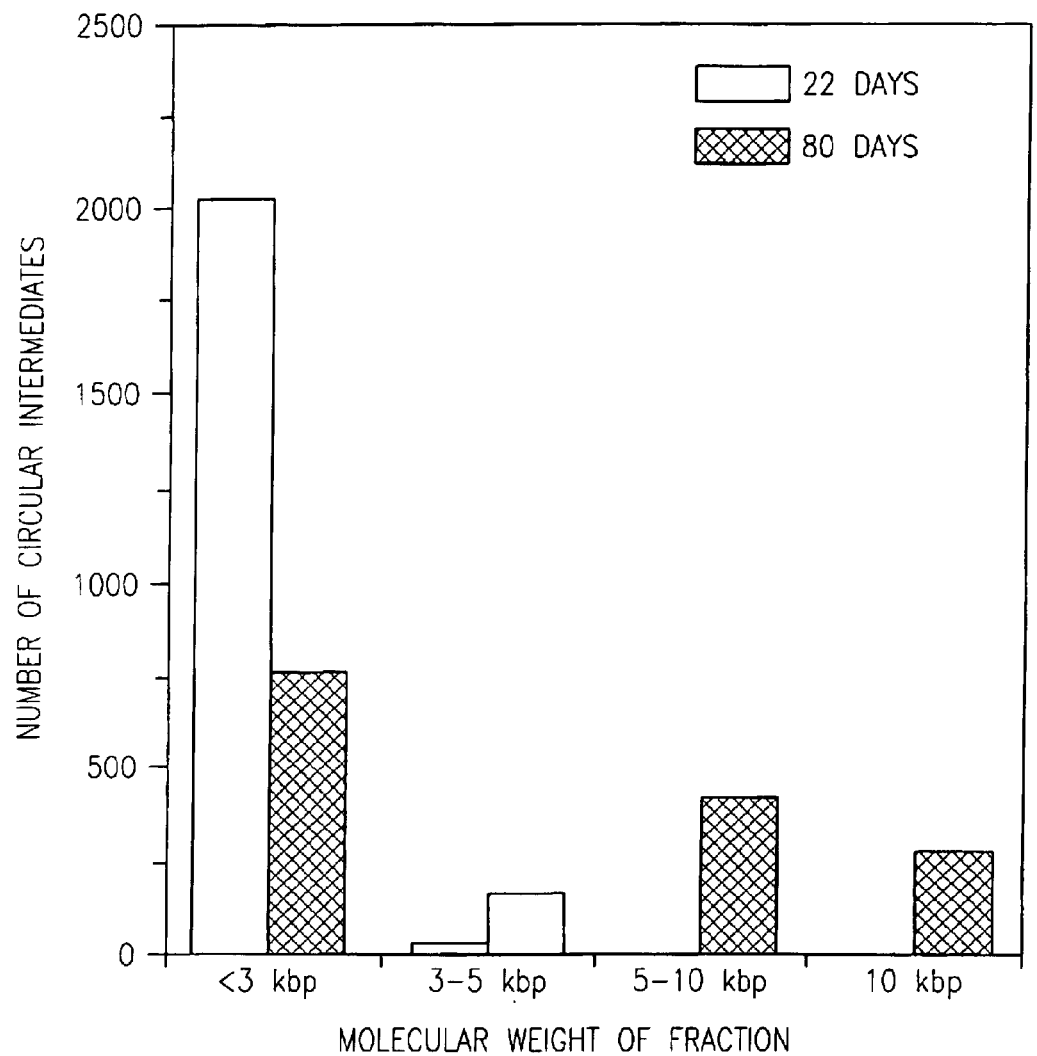
FIG. 6. Molecular size of circular intermediates in muscle. Hirt DNA from AV.GFP3ori infected muscle was size fractionated by electrophoresis and various molecular weight fractions transformed into E. coli. Results demonstrate the abundance of circular intermediates at each of the given molecular weights at 22 and 80 days post-infection with the rAAV shuttle vector. Structure of circular intermediates were confirmed by Southern blot restriction analysis.

To further characterize the circular intermediates isolated from muscles, Hirt samples from 22 days and 80 days post-infected muscles were size fractionated by continuous-flow gel electrophoresis (BioRad). As shown in FIG. 6, the majority of circular intermediates at 22 days post-infection size fractionated at a molecular weight of less than 3 Kbp. Very few clones were isolated from fractions between 3 to 5 kb and no clones were obtained from fractions larger than 5 kb at this time point. Furthermore, this size fractionated molecular weight of in vivo Hirt derived circular intermediates at 22 day time points correlated with that of head-to-tail monomer undigested circular intermediate plasmids rescued in bacteria from this same time point (approximately 2.5 kb). These data suggest that at early time points post-infection in muscle, the predominant form of circular intermediates likely occurs as monomer genomes. The lower mobility of this fraction as compared to replication form monomer (Rfm=4.7 kb) and dimer (Rfd=9.4 kb) genomes provides indirect evidence that these forms are not responsible for rescued plasmids in these Hirt samples. Interestingly, when 80 day muscle Hirt samples were size fractionated, more clones were retrieved from higher molecular weight fractions ranging from 3-12 kb (FIG. 6). This shift in the molecular weight of circular intermediates indicates the potential for recombination between monomer forms in the generation of large circular multimer genomes. Such concatamerization has been previously observed in muscle and has traditionally been hypothesized to involve linear integrated forms of the AAV genome (Herzog et al., 1997; Xiao et al., 1996; Clark et al., 1997; Fisher et al., 1997). This data sheds new light on the molecular characteristics of these persistent AAV genomes and suggests that they are in fact circular and episomal. Based on yields of retrievable circular plasmids reconstituted in Hirt DNA, the efficiency of bacterial transformation, and the initial innoculum of virus, we estimate that approximately 1 in 400 viral DNA particles circularize following infection in muscle (Table 2).

TABLE 2

Yield of Circular Intermediate Isolation from Hirt DNA

| Bacterial Transformation | Starting Number of Plasmid or AAV Genomes | Actual Number of Amp$^r$ cfu | Adjusted Yield |
| --- | --- | --- | --- |
| Hirt DNA from rAAV Infected Muscle[a] | 3 × 10$^{10}$ molecules | 5 × 10$^3$ cfu | 5 × 10$^5$ cfu[e] |
| Hirt DNA + 230 ng LacZ Plasmid[b,c] | 3 × 10$^{10}$ molecules | 2 × 10$^6$ cfu[d] | 2 × 10$^8$ cfu |
| 230 ng LacZ Plasmid[c] | 3 × 10$^{10}$ molecules | 2 × 10$^8$ cfu | — |

[a]The actual amount of Hirt used for transformation was 3/20 the entire Hirt DNA. The numbers have been adjusted to reflect viral innoculum and yields for the entire muscle.
[b]Plasmid DNA was spiked into mock infected muscle homogenates prior to isolation of Hirt DNA. This reconstituted Hirt DNA was then used for transformation of bacteria.
[c]The actual microgram amounts of plasmid used in reconstitution experiments was 10 ng. The numbers have been adjusted for comparison to normalize the number of plasmids genomes to that used in AAV experiments. Control LacZ plasmid was approximately 7000 bp with a molecular weight of 4.6 × 10$^6$ g/mole.
[d]The average of several experiments indicates an approximate 100-fold reduction in the number of cfu recovered from bacterial transformations with DNA isolated from Hirt extract spiked with plasmids as compared to transformation with an equivalent amount of plasmid DNA alone.
[e]Adjusted yield indicate approximately 1 in 400 AAV genomes circularize in vivo.

Given the fact that not all rAAV particles likely contain functional DNA molecules and intermediates may integrate, these calculations may represent an underestimation.

AAV Circular Intermediates Demonstrate Increased Persistence as Plasmid Based Vectors.

Based on the finding that circular AAV intermediates were associated with long term persistence of transgene expression in muscle, rAAV circular head-to-tail intermediates may be molecular structures of the AAV genome associated with the latent life cycle and increased episomal stability. Several aspects of the structure of AAV circular intermediates may account for their increased stability in vivo. First, circularization of AAV genomes may create a nuclease resistant conformation. Secondly, since the only viral sequences contained within circular intermediates are the head-to-tail ITR array, these sequences might bind cellular factors capable of stabilizing these structures in vivo. Several studies have demonstrated increased persistence of transgene expression with plasmid DNA encoding viral ITRs (Philip et al., 1994; Vieweg et al., 1995). The results described above provide a functional explanation for the increased persistence through the association with circular intermediate formation as part of the AAV life cycle.

Figure 7A:
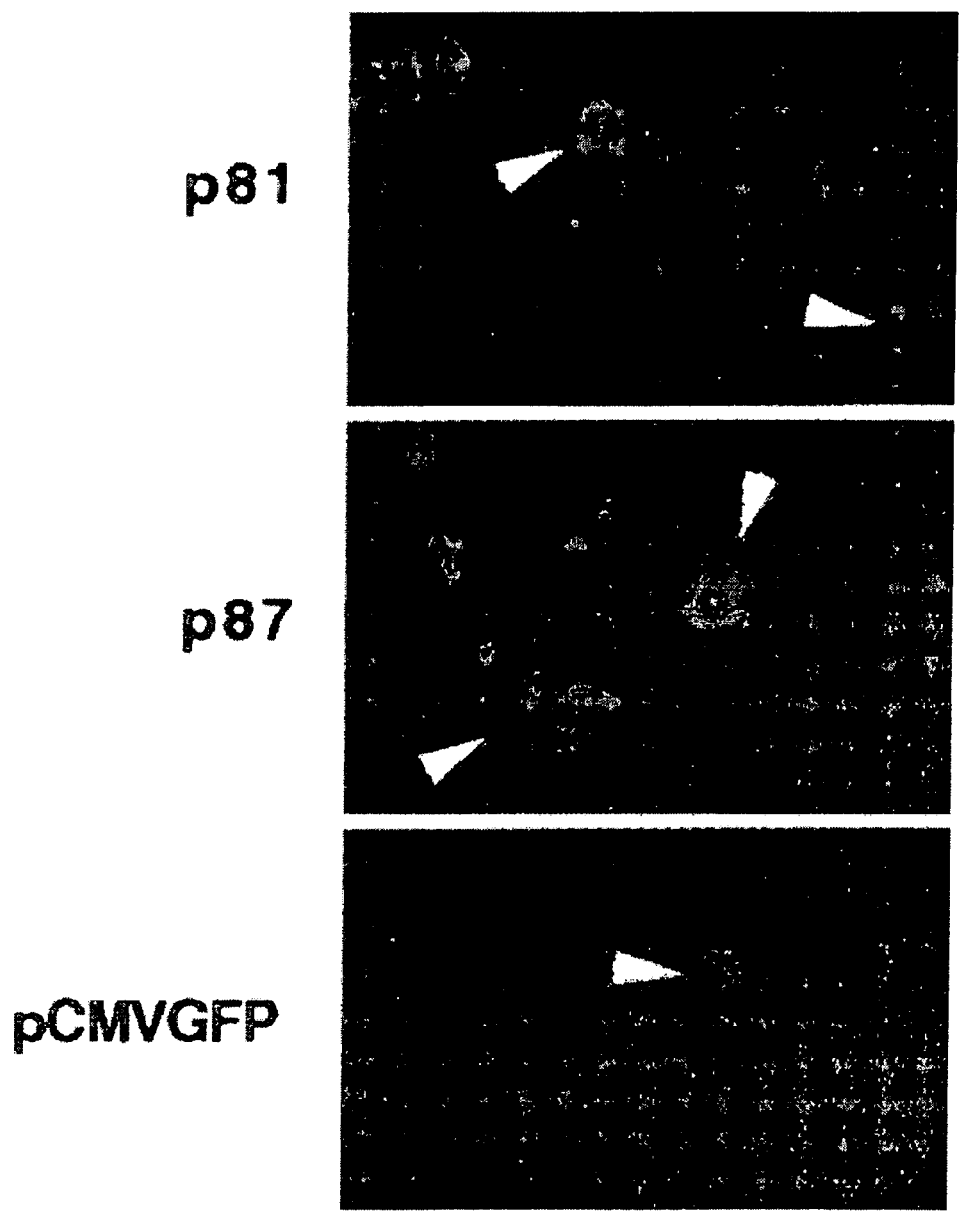
FIG. 7. Head-to-tail circular intermediates demonstrate increased stability of GFP expression following transient transfection in Hela cells. Subconfluent monolayers of Hela cells were co-transfected with p81, p87, or pCMVGFP and pRSVlacZ as an internal control for transfection efficiency as described in the methods. Panel A demonstrates the expansion of GFP clones after one passage (arrows). Quantification of clone size and numbers are shown in Panel B. Clone size represents the mean raw values while clone numbers are normalized for transfection efficiency as determined by X-gal staining for pRSVlacZ. The data at the top of bar graph values for each construct in Panel B represents quantification of GFP clones after second passage (also normalized for transfection efficiency). Results indicate the mean (+/−SEM) of duplicate experiments with greater than 20 fields quantified for each experimental point. The persistence of transfected p81 and pCMVGFP plasmid DNA at passage-7 post-transfection was evaluated by genomic Southern blot of total cellular DNA hybridized against $^{32}$P-labeled GFP probe (Panel C, results from two independent transfections are shown). U:uncut, C:PstI cut. The migration of uncut dimer and monomer plasmids forms are marked on the left. PstI digestion of the plasmids results in bands at 4.7 kb (pCMVGFP, single PstI site in plasmid) and 1.7 kb (p81, two PstI sites flanking the GFP gene). To determine whether the head-to-tail ITR array within circular intermediates was responsible for increases in the persistence of GFP expression, the head-to-tail ITR DNA element was subcloned into the pGL3 luciferase plasmid to generate pGL3(ITR). Results in Panel D compare the extent of luciferase transgene expression following transfection with pGL3 and pGL3(ITR) at 10 days (passage-2) post-transfection. Results are the mean (+/−SEM) for triplicate experiments and are normalized for transfection efficiency using a dual renilla luciferase reporter vector (pRLSV40, Promega).
Figure 7B:
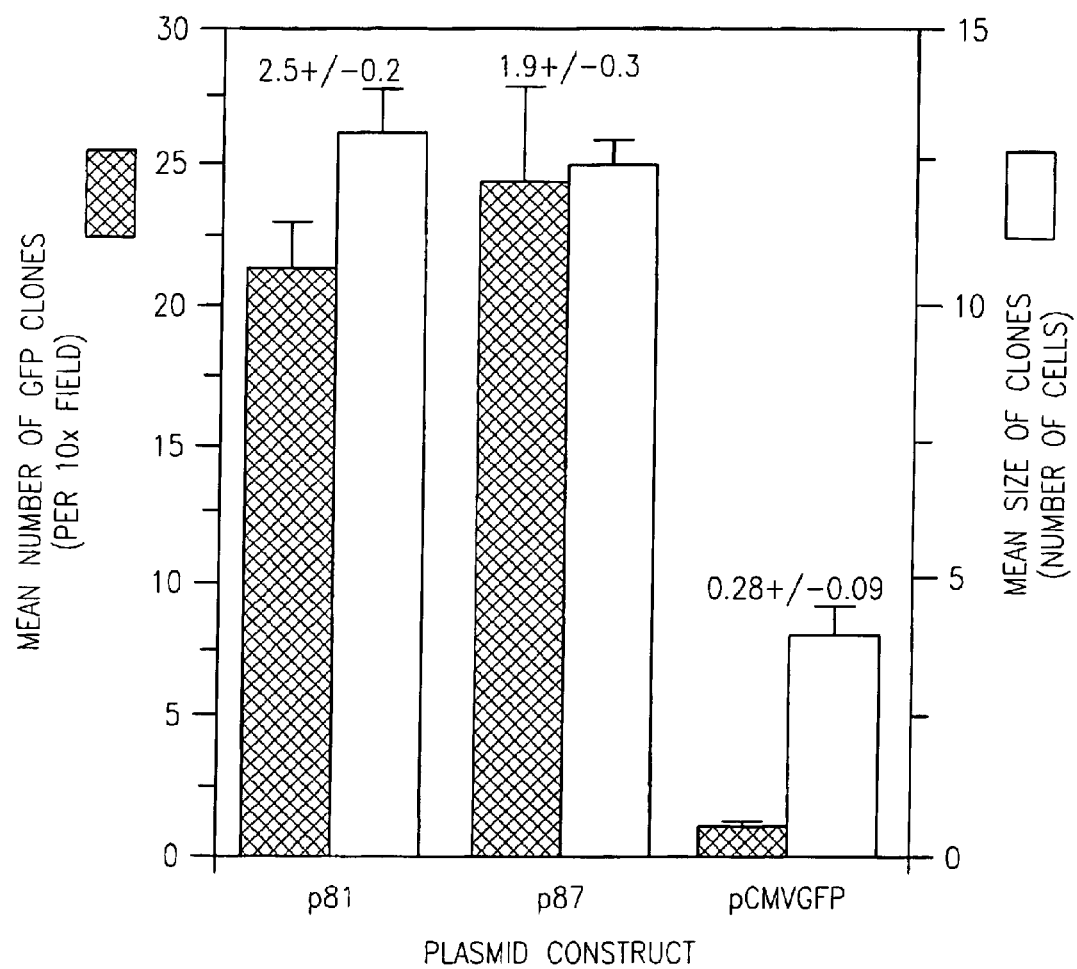

To more closely evaluate the persistence of AAV head-to-tail circular intermediates, several in vitro experiments were performed by transfecting these intermediates into Hela cells and assessing the stability of plasmid DNA and transgene expression by GFP clonal expansion. Results from Hela cell transfection experiments demonstrated that two monomer head-to-tail circular intermediates (p81 and p87) studied gave rise to a 10-fold higher number of five and ten day transgene-expressing clones, as compared to a control pCMVGFP plasmid lacking the ITR sequences (FIGS. 7A and B). Additionally, the size of GFP positive colonies at 5 days post-transfection was three-fold larger in Hela cells transfected with p81 and p87, as compared to the pCMVGFP control vector (FIGS. 7A and B). These studies suggest the AAV circular intermediates have increased stability of transgene expression and substantiate findings in muscle.

Figure 7C:
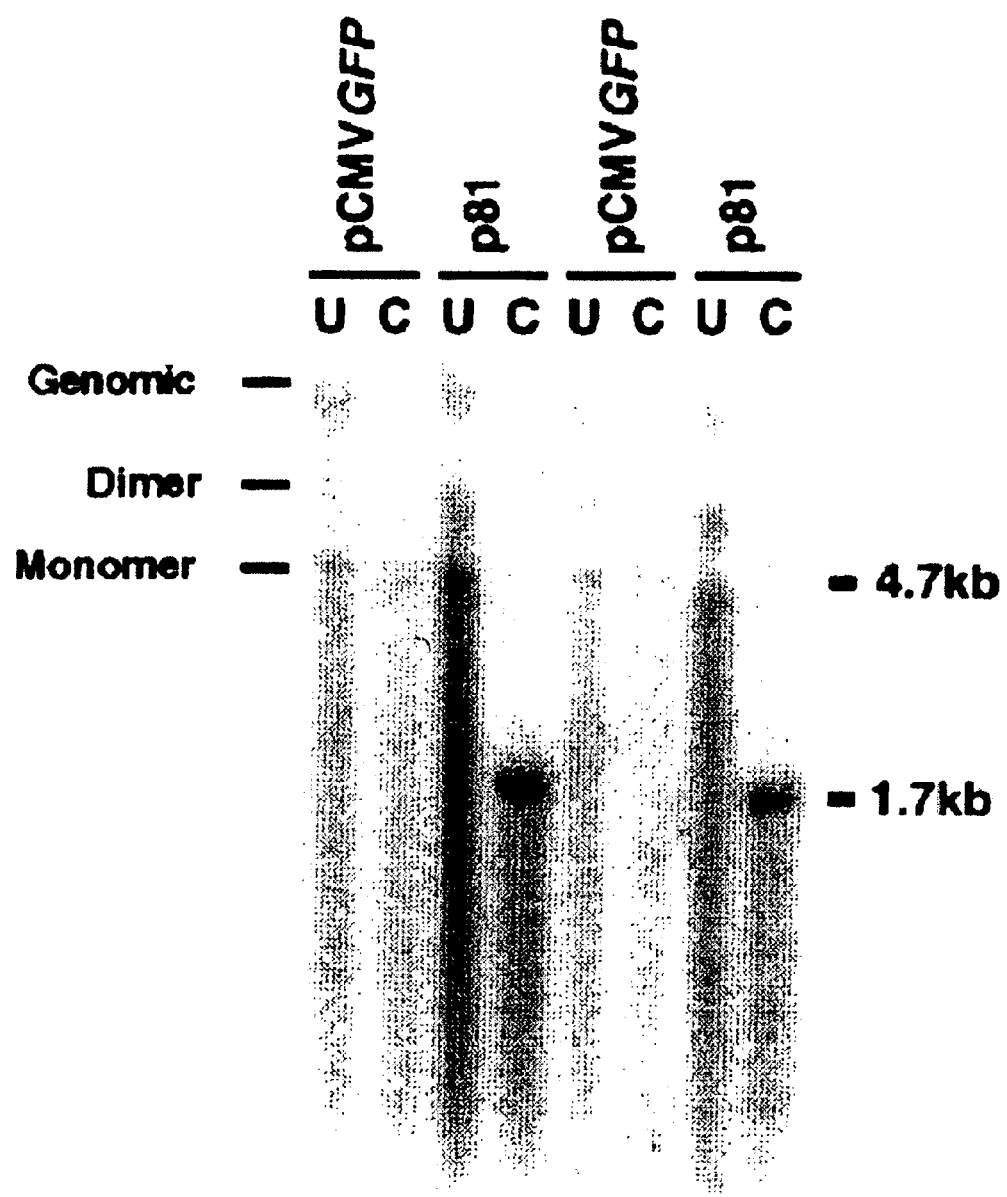

To confirm the increased molecular persistence of head-to-tail circular intermediates following transfection into Hela cells, total DNA (low and high molecular weight) was isolated from cultures of pCMVGFP and p81 transfected Hela cells at various passages post-transfection and analyzed by Southern blotting. Southern blots hybridized to $^{32}$P-labeled GFP probes demonstrated a significantly higher level of p81 plasmid DNA at passage-7 as compared to the control vector lacking the head-to-tail ITR sequence (FIG. 7C). The majority of signal in undigested DNA samples was associated with a 4.7 kb band migrating at the approximate size of the uncut monomer plasmids. Together with the fact that the majority of signal from all cell cultures in FIG. 7C disappeared by passage-10, these data suggest that these plasmids predominantly remained episomal. Thus, in both muscle and Hela cells, increased persistence of AAV circular intermediates is correlated with stable transgene expression.

ITR Arrays are Responsible for Increased Persistence.

Figure 7D:
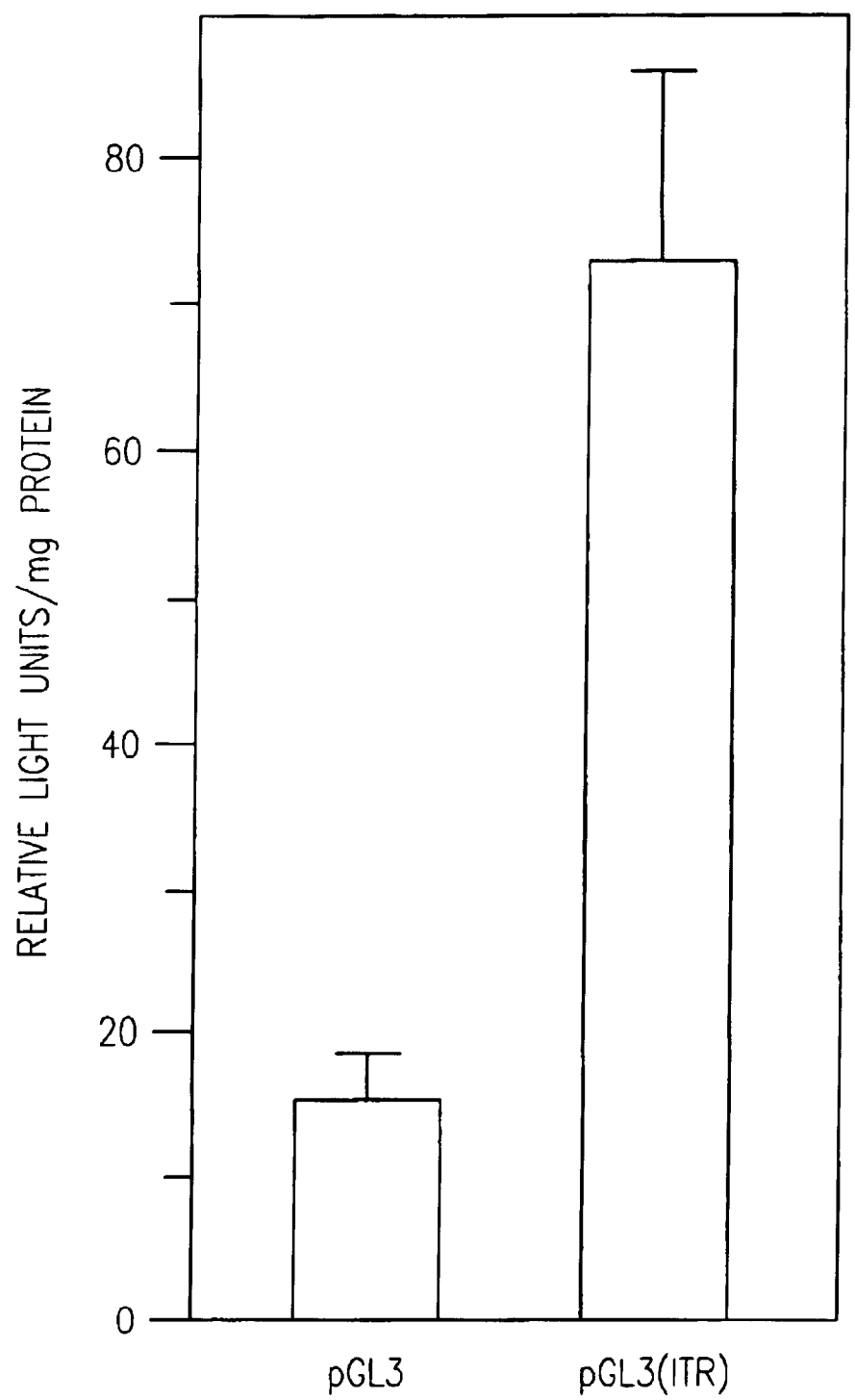
Figure 8A:
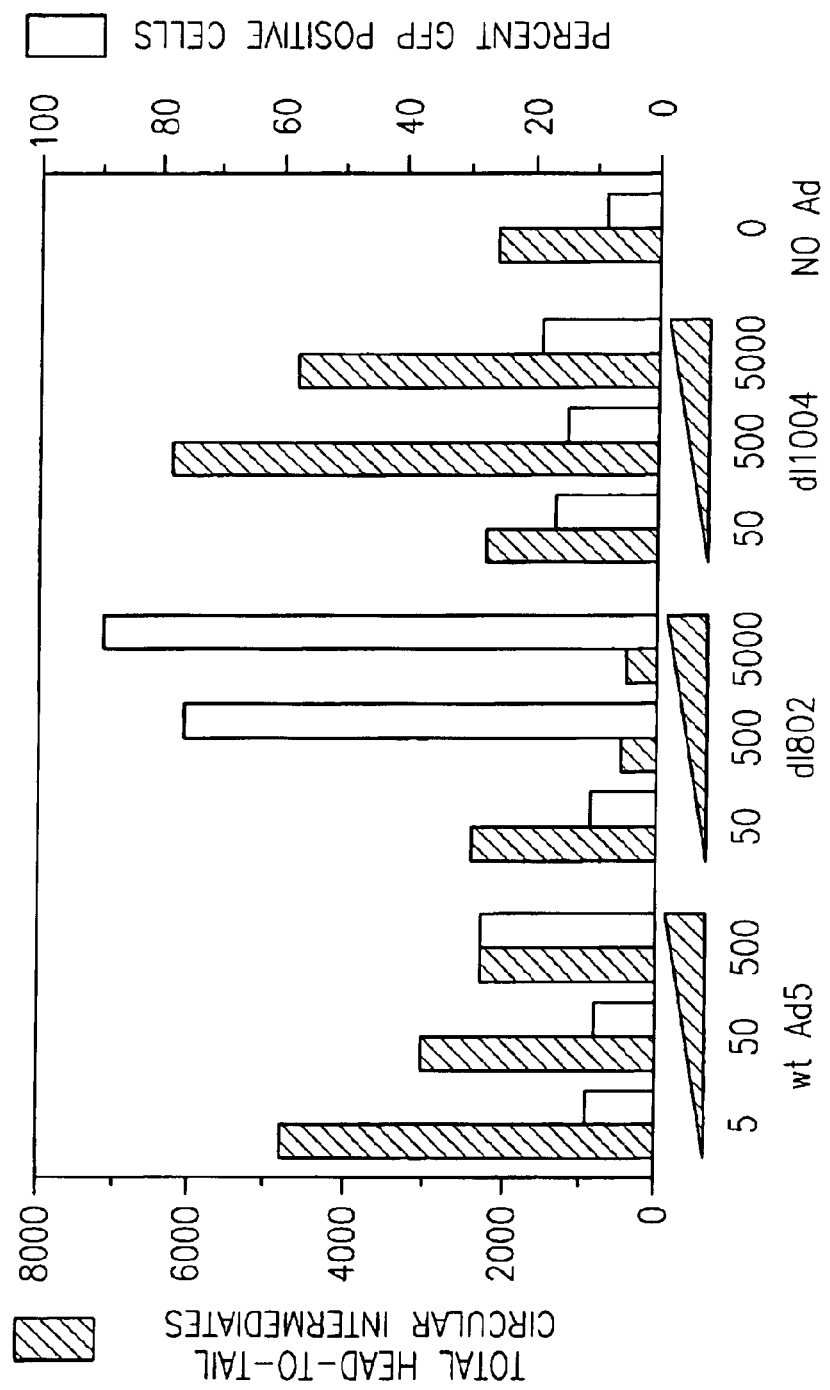
FIG. 8(Parts A–B). Identification of adenoviral genes responsible for augmentation of AAV circular intermediate formation. Hela cells were infected with AV.GFP3ori (1000 DNA particles/cell) in the presence of wtAd5, dl802 (E2a-deleted), and dl 1004 (E4-deleted) adenovirus (at the indicated MOIs). Total number of head-to-tail circular intermediates from Hirt DNA and the level of augmentation of GFP transgene expression (as determined by FACS) was quantified at 24 hours post-infection (Panel A). Results are the average of duplicate experiments. Panel B depicts results from Southern blot analysis of Hirt DNA following hybridization to a GFP $P^{32}$-labeled probe. DNA loads were 10% of the total Hirt yield from a 35 mm plate of Hela cells. Infections were carried out identically to that described for Panel A. Arrows mark replication form concatamers ($Rf_c$), dimers ($Rf_d$), monomers ($Rf_m$), and single-stranded AAV genomes (ssDNA).
Figure 8B:
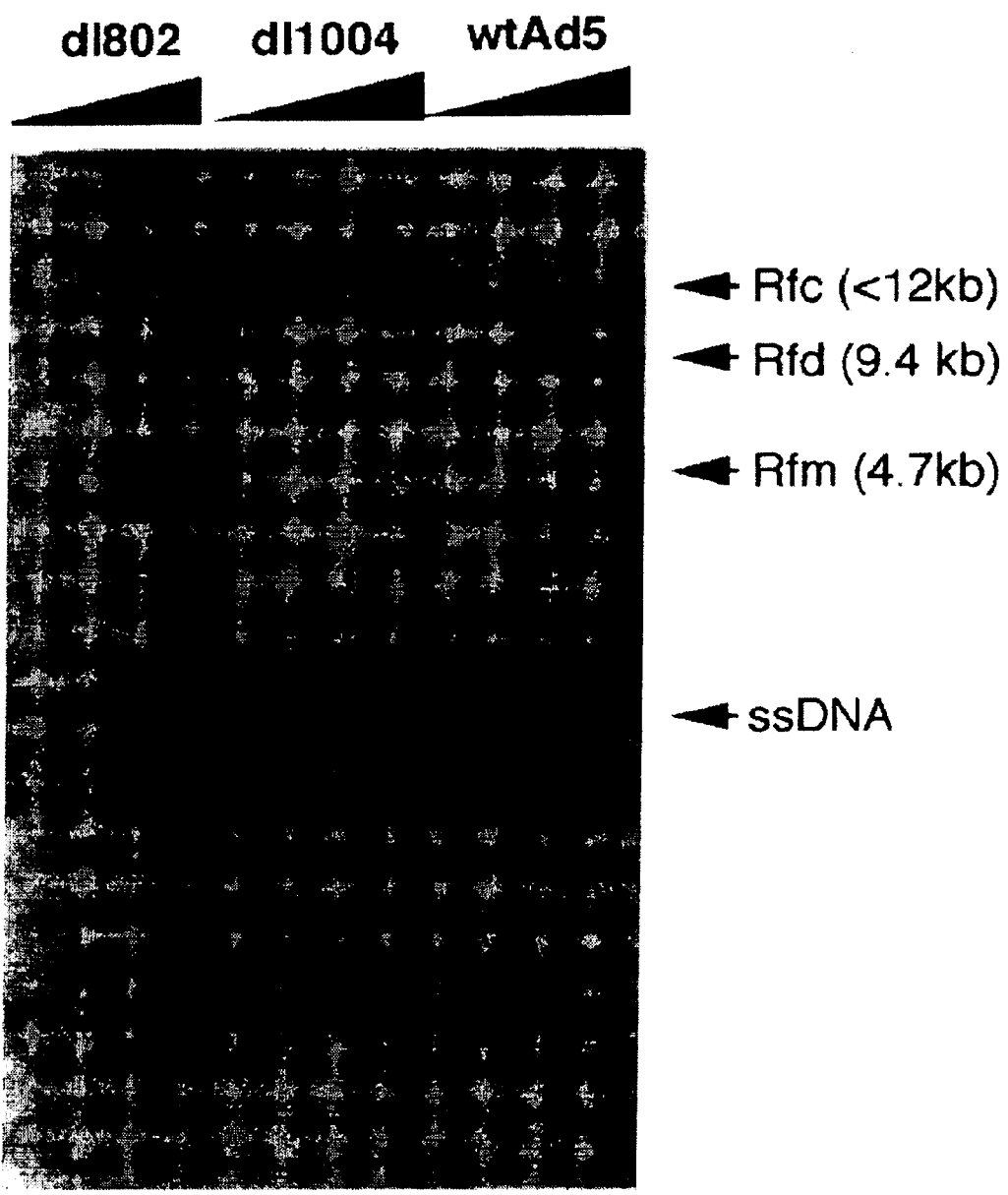
Figure 9:
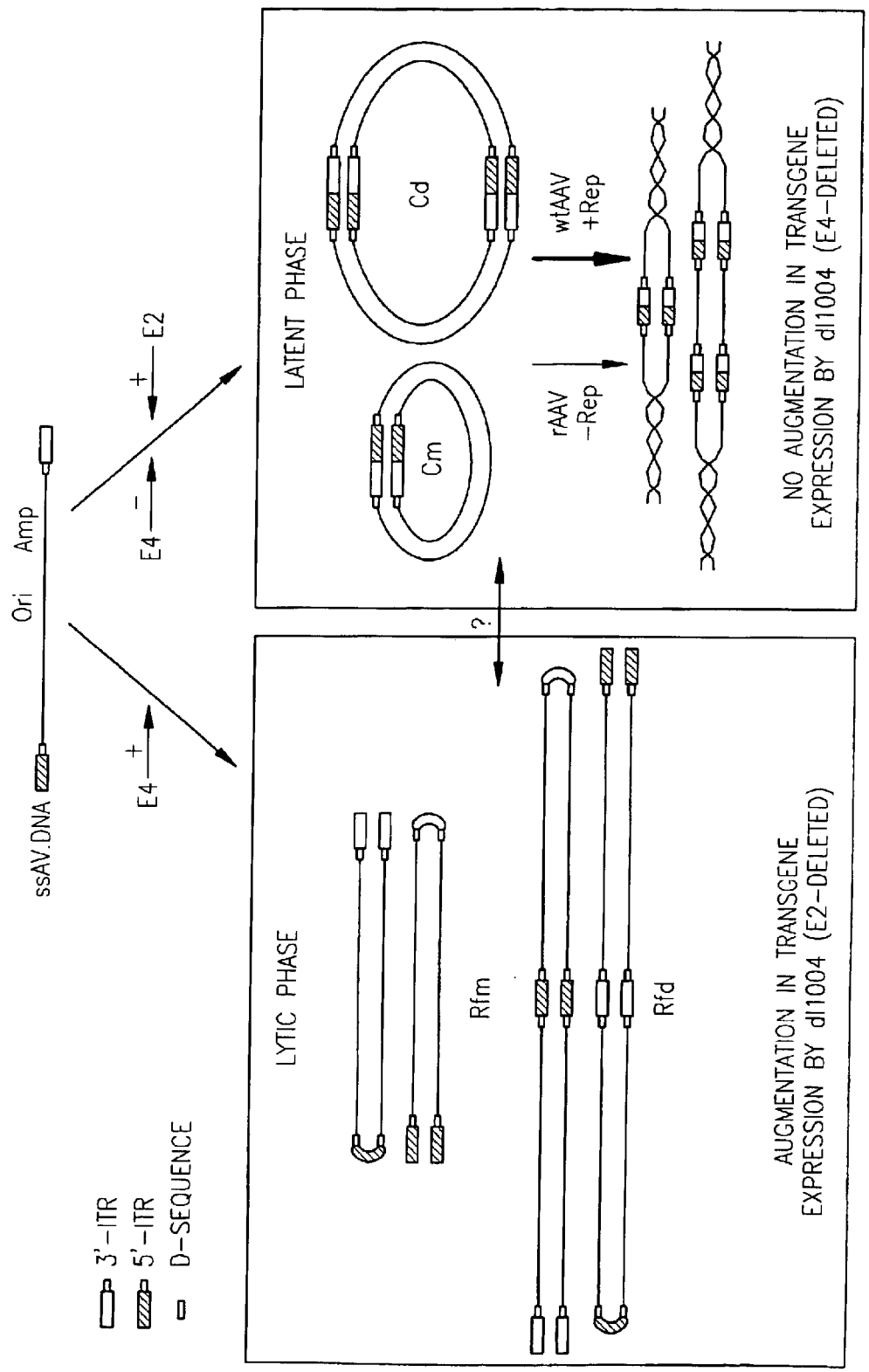
FIG. 9. Model for independent mechanistic interactions of adenovirus with lytic and latent phase aspects of the AAV life cycle. The adenoviral E4 gene has been shown to augment the level of rAAV second strand synthesis giving rise to replication form dimers ($Rf_d$) and monomers ($Rf_{m'}$) (FIG. 8B). This augmentation leads to substantial increases in transgene expression from rAAV vectors and most closely mirrors lytic phase replication of wtAAV as head-to-head and tail-to-tail concatamers. In contrast, E4 expression inhibits the formation of head-to-tail circular intermediates of AAV. Hence, it appears that increases in the amount of $Rf_d$ and $Rf_m$ double stranded DNA genomes does not increase the extent of circular intermediate formation. Such findings suggest that conversion of $Rf_m$ and $Rf_d$ to circular intermediates does not likely occur and implicates two mechanistically distinct pathway for their formation. In support of this hypothesis, adenoviral E2a gene expression does not enhance the formation of $Rf_m$ and $Rf_d$ genomes but rather increase the abundance and/or stability of head-to-tail circular intermediates. Furthermore, in the absence of E4, E2a gene expression does not lead to augmentation of rAAV transgene expression. Since circular intermediates have increased episomal stability in muscle and in Hela cells, this molecular structure may be important in the latent phase of AAV persistence. Alternatively, these circular intermediates may represent pre-integration complexes as previously hypothesized for Rep facilitated integration. In the absence of Rep, circular intermediates may accumulate episomally in rAAV infected cells. In summary, these findings support the notion that adenovirus may modulate both latent and lytic aspects of the AAV life cycle.
Figure 12A:
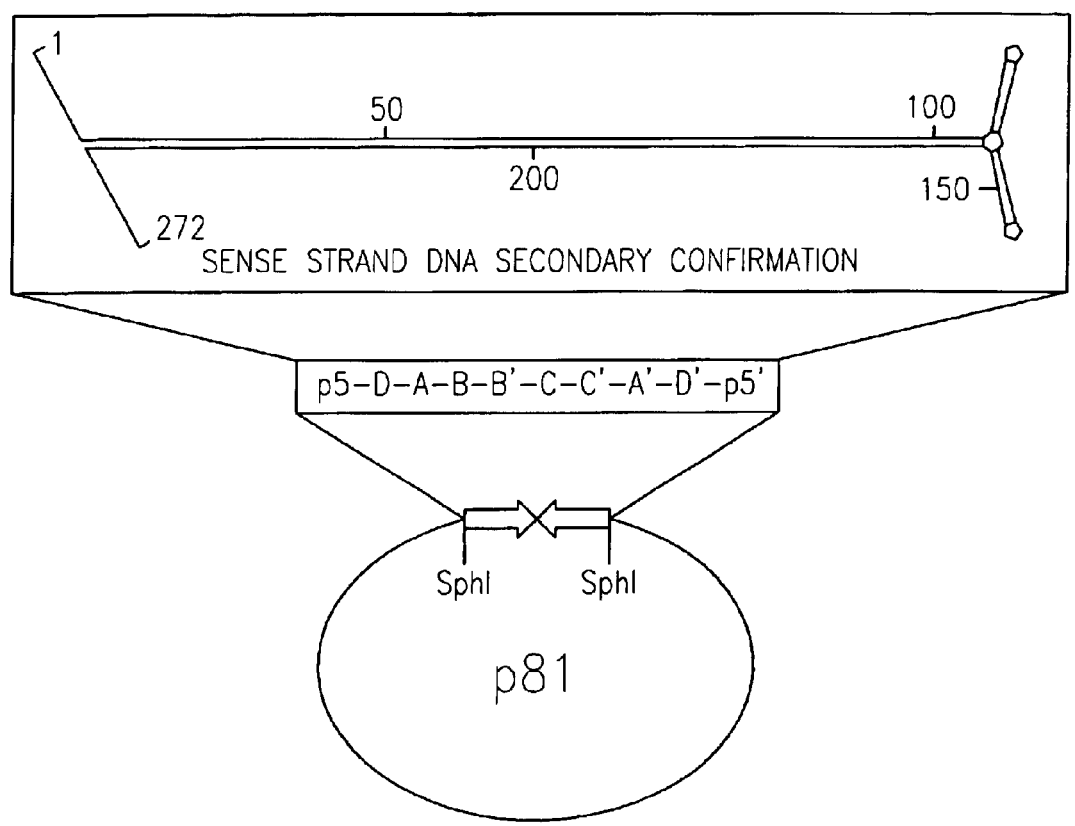
FIG. 12A. Palindromic repeat structure derived from chemical sequencing of AAV circular intermediate isolate p81. Secondary structure of the sense strand is depicted in the top box with plasmid reference given below.
Figure 12B:
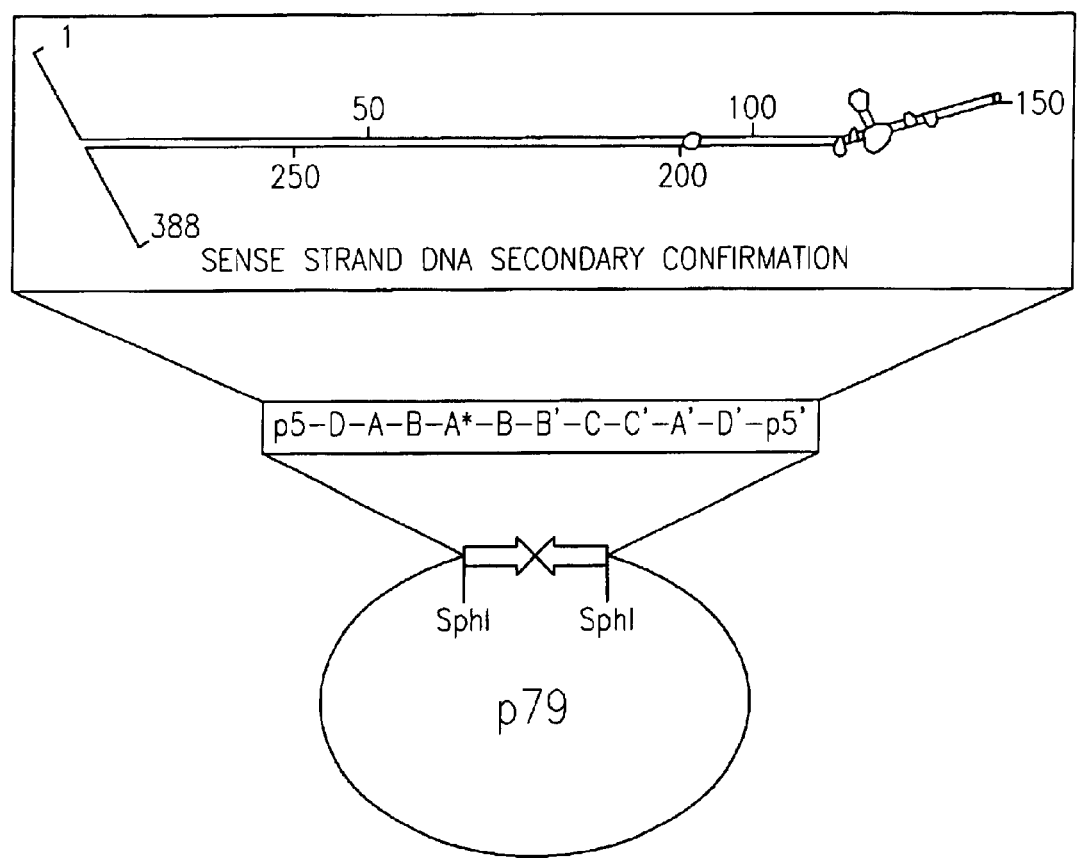
FIG. 12B. Palindromic repeat structure derived from chemical sequencing of AAV circular intermediate isolate p79. Secondary structure of the sense strand is depicted in the top box with plasmid reference given below.
Figure 12C:
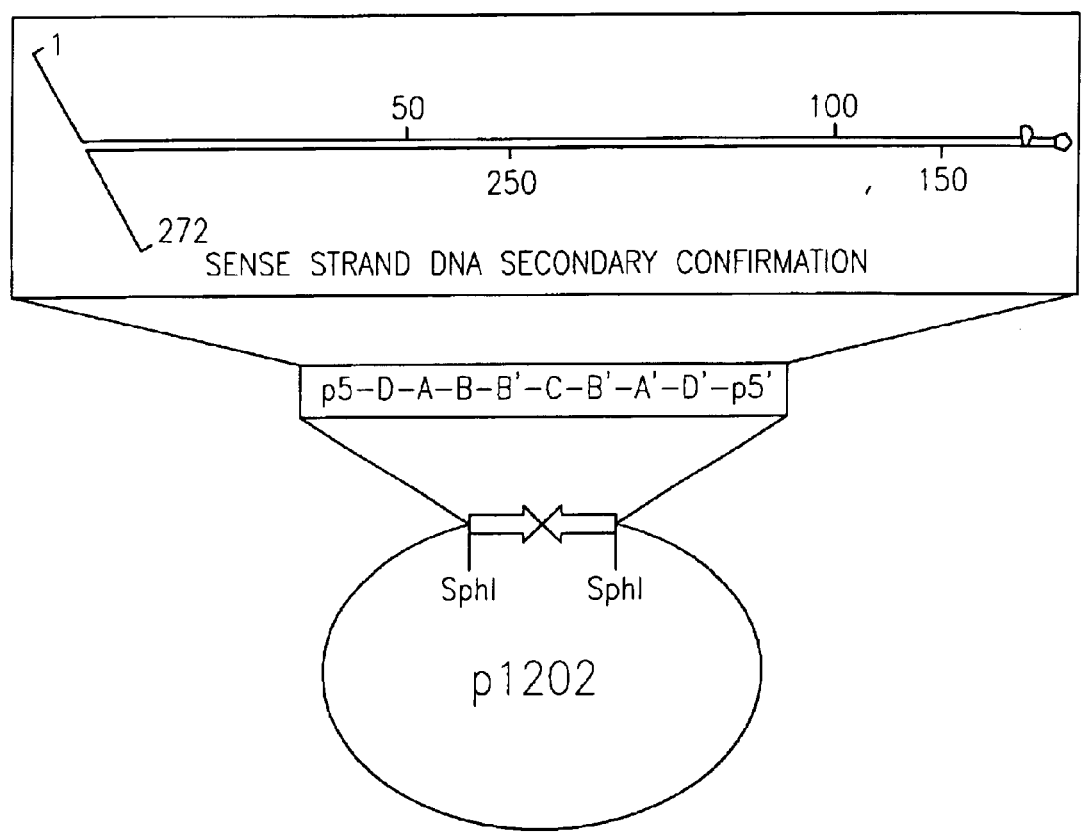
FIG. 12C. Palindromic repeat structure derived from chemical sequencing of AAV circular intermediate isolate p79. Secondary structure of the sense strand is depicted in the top box with plasmid reference given below.

To investigate whether the head-to-tail ITR DNA element was responsible for the increased persistence of circular intermediates, we cloned this DNA element into a secondary luciferase vector (pGL3) to give rise to pGL3(ITR). Transient transfection experiments in Hela cells demonstrated a five-fold increase in the persistence of luciferase expression in serially-passaged cultures at 10 days in pGL3(ITR) as compared to that of pGL3 transfected (FIG. 7D). These findings support the hypothesis that the head-to-tail ITR DNA element contained within circular intermediates is responsible for mediating the increased persistence of transgene expression and suggest a mechanism by which these molecular intermediates may confer stability to AAV genomes in vivo. Furthermore, increases in the stability of transgene expression conferred by this element appear to be primarily context independent, since the head-to-tail ITR element was 3' to the luciferase gene in pGL3(ITR) and 5' to the GFP transgene in AAV circular intermediates.

Discussion

Characterization of integrated proviral structures in different cell lines has demonstrated head-to-tail genomes as the predominant structural forms for both wild type and recombinant AAV (McLaughlin et al., 1988; Cheung et al., 1980; Duan et al., 1997). This is in contrast to the head-to-head and tail-to-tail structures observed in AAV replication intermediates (Rfm and Rfd). Both Rfm and Rfd configurations have also been demonstrated in rAAV infected cells and enhanced conversion of ssAAV genomes to double stranded Rfm and Rfd forms has been suggested as a mechanism for augmentation of rAAV transduction by adenovirus in cell lines (Ferrari et al., 1996; Fisher et al., 1996). However, it is plausible that the mechanisms responsible for the formation of Rfm and Rfd molecules are different from pathways which lead to long-term transgene expression. In support of this hypothesis is a recent study evaluating augmentation of rAAV transgene expression by adenovirus in liver (Snyder et al., 1997). These studies have demonstrated that co-infection of the liver with adenovirus and rAAV enhances short term transgene expression while long term expression was no different than rAAV alone. The exact mechanism for the formation of head-to-tail circular intermediates is not clear, however similar structures have been demonstrated to act as pre-integration intermediates for retrovirus (Varmus, 1982). In this regard, circularized retroviral genomes with one and two viral LTRs have been proposed. In addition, circular pre-integration intermediates have also been suggested by recent studies on wtAAV integration (Linden et al., 1996b). The demonstration that circular intermediates exist in rAAV infected muscle explains several features of latent phase infection with rAAV vectors including proviral structure and stable episomal persistence.

Previous studies have suggested that rAAV genomes delivered to muscle might persist as head-to-tail concatamers (Herzog et al., 1997; Clark et al., 1997; Fisher et al., 1997). However, it is currently unknown whether these concatamers exist as free episomes or as integrated proviruses in the host genome. The results described above, i.e., demonstrating prolonged persistence of head-to-tail circular intermediates at 80 days post-infection, suggest that a large percentage of rAAV genomes may remain episomal. The conversion of monomer circularized genomes to larger circularized multimers appears to be an aspect associated with long term persistence and likely represents recombinational events between monomer intermediates. Although the bacterial rescue strategy was not capable of satisfactorily addressing the size of multimers, our modified approach to size fractionating Hirt DNA prior to bacterial rescue of intermediates lends support to this hypothesis. Additional supportive evidence for increased recombination over time is the finding that greater variability in the length of ITR arrays was observed at longer time points post-infection. For example, at 5–22 days the majority of circular intermediates contained 2 ITRs in a head-to-tail fashion. This is in contrast to 80 day time points where the lengths of ITR arrays ranges from 1–3 ITRs. Such diversity of ITR arrays in muscle infected with AAV has been previously found using PCR approaches (Herzog et al., 1997; Fisher et al., 1997). In addition, the 30% decline in the abundance of circular intermediates in muscle between 22 and 80 days also supports a hypothesis that these molecular forms of AAV may represent pre-integration complexes.

Given the fact that circular intermediates had long term persistence in muscle, certain structural features of these intermediates may affect episomal stability of DNA. Previous studies have noted increased persistence of transgene expression from plasmids encoding AAV ITRs (Philip et al., 1994; Vieweg et al., 1995). However, the physiologic significance of this finding has remained elusive. The present study, demonstrating the head-to-tail ITR arrays isolated from AAV circular intermediates can confer increased episomal persistence to plasmids following transfection in cell lines, gives a mechanistic framework for ITR effects on plasmid persistence. Furthermore, the correlation that AAV circular intermediates have increased persistence in cell lines in vitro, lends support to the hypothesis that these structures represent stable episomal forms following rAAV transduction in muscle. Stability of circular intermediates in vivo might be mediated by the binding of cellular factors to "Holliday-like" junctions in ITR arrays which stabilize or protect DNA from degradation.

rAAV has been shown to be an efficient vector for expressing transgenes in various tissues in addition to muscle, such as brain, retina, liver, lung, and hematopoetic cells (Snyder et al., 1997; Muzyczka, 1992; Kaplitt et al., 1994; Walsh et al., 1994; Halbert et al., 1997; Koeberl et al., 1997; Conrad et al., 1996; Bennett et al., 1997; Flannery et al., 1997). Despite these advances in the application of rAAV, the mechanisms of in vivo rAAV-mediated transduction and persistence of transgene expression still remain unclear. Such questions as to the molecular state of rAAV following in vivo delivery is highly relevant to the clinical application of this viral vector. For example, should rAAV primarily persist as an randomly integrated provirus, the potential for insertional mutagenesis could present a major theoretical obstacle in the use of this vector due to the potential for mutational oncogenesis. The demonstration that rAAV can persist as episomes suggest that random integration and associated risks of malignancy may not be a major concern for this viral vector system. Additionally, the molecular determinants of AAV circular intermediates associated with increased persistence in cell lines appear to be contained within the DNA elements encompassing the inverted ITRs. The isolation of this naturally occurring viral DNA element, which forms as part of the AAV life cycle and acts to stabilize circular episomal DNA, may prove useful in increasing the efficacy of both viral and non-viral gene therapy vectors.

EXAMPLE 3

Figure 13:
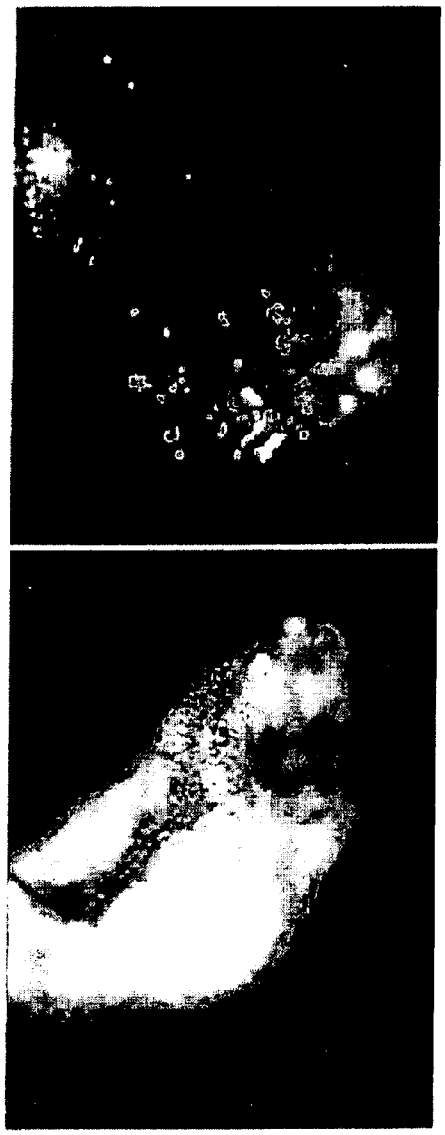
FIG. 13. Persistence of GFP expression in developing Xenopus embryos microinjected with AAV circular intermediate isolate p81. The extent of GFP fluorescence in tadpoles reflects the stability of episomal or integrated microinjected plasmids. Bright field image on the left is of the p81 injected embryo. The p81 injected embryo depicts fluorescence in nearly all cells by one week post-injection. In contrast, a mosaic pattern of expression in a minority of cells in pCisAV.GFPori injected embryos. The pCisAV.GFPori plasmid contains the identical promoter sequences driving GFP gene expression and two ITRs separated by stuffer sequence. These findings demonstrate that specific structural characteristics found within AAV circular intermediates are responsible for increased persistence of transgene expression.

Evidence for Increased Episomal Persistence of AAV Circular Intermediates in a Model for in utero Plasmid-based Gene Therapy Persistence of AAV circular intermediates were assessed by injection of plasmid DNA directly into the pronucleus of fertilized Xenopus oocytes. Twenty-five ng of the p81 isolate of AAV circular intermediates was injected at the single cell stage of fertilized Xenopus oocytes. This plasmid was compared to the proviral plasmid pCisAV.GFP3ori, which contains two ITRs separated by stuffer sequence in an alternative confirmation to ITRs in p81. FIG. 13 depicts the persistence of GFP plasmids as assessed by direct fluorescence of GFP. At this state of tadpole development, the fertilized oocyte has expanded from a single cell to approximately $10^6$ cells.

These studies confirm that AAV circular intermediates (p81) confer a higher level of stability in development Xenopus oocytes than plasmids containing similar transcriptional elements and ITR sequences in an alternative confirmation. Given that in the case of p81 injected oocytes, tadpoles are completely fluorescent, the data suggests that some level of integration may have occurred.

EXAMPLE 4

Liposome Mediated Transfer of Vectors of the Invention to the Airway and Muscle

Studies evaluating the mechanisms of recombinant adeno-associated virus (AAV) transduction have identified a novel molecular intermediate responsible for episomal persistence. This intermediate is characterized by a circularized AAV genome with head-to-tail ITR repeats. Circular intermediates of rAAV were identified using a recombinant shuttle vector capable of propagating circularized viral genomes in bacteria. Pivotal experiments in cell lines demonstrate that the formation and persistence of these circular intermediates are augmented in the presence of helper adenovirus. These findings suggest that cellular factors induced by adenoviral gene expression may modulate both the formation and/or persistence of AAV circular intermediates. Furthermore, studies in muscle have demonstrated that following rAAV infection, the formation and persistence of AAV circular intermediates correlates with the onset and maintenance (at 80 days) of transgene expression, respectively. Moreover, a 300 bp fragment encompassing the head-to-tail inverted ITR repeats found in AAV circular intermediates when cloned into heterologous expression plasmids can confer increased stability to those plasmids in HeLa cells. The structural aspects of AAV circular intermediates may lead to development of non-viral, plasmid based, gene transfer vectors with increased persistence of transgene expression.

To determine whether AAV circular intermediates which differ in length and/or sequence of the ITR array are more efficacious plasmid based vectors for liposome-mediated gene transfer to the airway and muscle, several distinct forms of AAV circular intermediates are evaluated as plasmid-based delivery systems in three model systems of the airway including: 1) in vitro polarized primary airway epithelial monolayers, 2) mouse lung, and 3) human bronchial xenografts. Persistence is evaluated at both the level of transgene expression (using GFP and luciferase reporters) and at the level of episomal and integrated transgene derived DNA. Studies are performed to assess whether integration can be specifically enhanced by co-transfection with Rep DNA or MRNA. These studies also evaluate both the extent of integration and site specificity to AVS1 sites in chromosome 19 of human model systems.

Gene therapy using plasmid-based delivery systems have encountered several obstacles to efficient transgene expression. These obstacles include transient expression of transgenes and rapid degradation of DNA. In contrast, viruses have developed efficient mechanisms for transducing cells and expressing encoded viral genes. The molecular characteristics of AAV circular intermediates which confer increased persistence of transgene expression include a DNA element encompassing the head-to-tail ITR. Based on the findings that circular intermediates have increased episomal persistence in muscle following rAAV transduction, these structures may also have increased persistence as plasmid-based vehicles to the airway. Interestingly, several naturally occurring mutations which are found in approximately 50% of AAV circular intermediates affect the stability of the intermediate.

Several findings evaluating the efficiency of AAV circular intermediate formation from recombinant viral vectors have suggested that these structures are augmented in abundance by the presence of the E2a adenoviral gene product. These molecular structures may represent preintegration intermediates which, in the case of wild-type AAV, would efficiently integrate into the cellular genome by Rep facilitated mechanisms. However, in the case of recombinant AAV genomes (in the absence of Rep proteins), evidence suggests that these structures have increased episomal stability. To test whether exogenous addition of Rep and/or E2a can increase the efficacy of AAV circular intermediates by modulating their stability and/or integration, co-transfection methods with Rep encoding plasmids and mRNA are conducted. Additionally, exogenously supplied E2a DNA binding protein (DBP) may also enhance stability of AAV circular intermediates. Rep may increase the integration of circular intermediates while E2a may increase their episomal stability. Several observations including the association of E2a DBP with AAV genomes in the nucleus support a direct interaction between DBP and AAV circular intermediates. Furthermore, if DBP associates with AAV circular intermediates, its encoded nuclear localization sequence (NLS) may enhance nuclear sequestration of these plasmids in the nucleus. Alternatively, E2a may act to alter the persistence of AAV circular intermediates through the induction of cellular factors which interact with the ITR array.

Liposome mediated gene transfer to the airway has considerable advantages due to the low level of toxicity. However, limitations include transient low level expression in differentiated airway epithelia. Despite this apparent limitation, several laboratories have had considerable success with the use of cationic liposome-mediated gene transfer in several animal models including mouse and rat lung, and numerous laboratories have pursued clinical trials, which suggested that these vehicles may show promise for gene therapy of the cystic fibrosis (CF) lung. Thus, delivery of the present vectors in plasmid form via liposomes may be a safe and effective vehicle for gene transfer to the airway.

To assess whether AAV circular intermediates may also have increased persistence in airway epithelial cells as seen in Hela cells, several distinct forms of circular intermediates delivered by liposome-mediated transfection into primary airway epithelial cells, are evaluated. Based on the diversity of ITR repeat elements between various isolated circular intermediates (i.e., including 0, 1, 2, and 3 ITRs), circular intermediates isolated from later time points in muscle may have been naturally selected for increased stability in vivo. Hence, the structural consistencies between AAV circular intermediates are identified which give increased persistence as plasmid based vectors for gene transfer.

Circular intermediates containing the GFP reporter gene and 1, 2, and 3 ITRs are transfected into primary airway cultures and polarized epithelial cell monolayers using the cationic lipid GL-67 (Genzyme Inc.). DNA to lipid ratios are optimized using a luciferase reporter. Additionally, the addition of EGTA, or the use of calcium-free media, can increase the extent of gene transfer about 10-fold, and may be included to enhance gene transfer to polarized epithelial monolayers. To evaluate persistence and expression of transgenes from circular intermediates, direct fluorescent microscopy and Southern blotting of both Hirt and genomic DNA with GFP $P^{32}$-labeled probes are utilized. Proliferating cultures of primary airway epithelial cells can be passaged up to 4 times during this analysis. In contrast, polarized epithelial monolayers are evaluated at 1 week intervals for DNA persistence for up to 6 weeks. Since GFP transgene expression may be low and difficult to detect by direct fluorescence, GFP is quantitated by fluorometer of cell lysates.

Following AAV transduction, circular intermediates may form within cells and certain structures of these intermediates may persist by virtue of affinity for cellular factors which bind at ITR arrays. If this is true, then it may be possible to select for and isolate optimal circular intermediates with increased persistence in airway cells by batch screening of circular intermediates pools from rAAV infected airway epithelia.

Primary airway epithelia cell cultures are infected with AV. GFP3ori (MOIs of 1000 to 10,000 DNA part/cell) and low molecular Hirt DNA is prepared at 5–15 days post-infection. Hirt DNA containing circular intermediates from rAAV infected cells is used to then transfect primary airway epithelial cells from which Hirt DNA is prepared at 5–15 days post-transfection. This second Hirt isolation is then used to isolate replication competent plasmids following transformation into bacteria. This selection process may give rise to those populations of circular intermediates with increased episomal persistence in airway epithelial cells. Selected clones of circular intermediate plasmids isolated by this procedure are then tested individually for increased persistence following liposome mediated transfection. These studies are performed in a batch type screening in 24 well plates using two serial passages for persistence. Once plasmids having increased persistence are isolated, their structure and sequence of ITR arrays are characterized. Since screening is performed on small-scale cultures, it may be necessary to implement semi-quantitative screening for DNA persistence within the first round of transfection using PCR methods. Candidate plasmids with a high level of increased persistence as compared to control plasmids which lack ITR sequences but contain the identical promoter-reporter element, are evaluated on a larger scale transfection amenable to analysis by Southern blotting of total DNA.

To evaluate selected circular intermediate structures in vivo, two models including mouse lung and the human bronchial xenograft are employed. 10 wk BalbC mice are transfected with GL-67/DNA complexes at a ratio of 25 µg plasmid/25 µg lipid in an iso-osmotic solution of Dextrose. At 1, 5, 10, 15, and 20 days post-transfection lungs of mice are harvested for immunofluorescent detection of GFP in formalin fixed sections and for quantitative fluorometry of tissue lysates. Southern blots are employed to evaluate the persistence of plasmids in Hirt and genomic DNA. In addition to evaluating the persistence of selected circular intermediates which have the highest level of persistence with in vitro models, luciferase constructs are evaluated in which the ITR array has been cloned either 5' or 3' to the reporter gene. Furthermore, the use of luciferase reporters allows for more sensitive assessment of transgene activity in cell lysates.

Similarly, in vivo persistence of transfected circular intermediates and heterologous plasmids containing ITR arrays found within circular intermediates is evaluated in human bronchial xenografts.

Findings evaluating the effects of adenoviral co-infection on circular intermediate formation and persistence have suggested that E2a DBP leads to a 10-fold increase in the abundance of circular intermediates as compared to E2 deleted virus. Furthermore, studies with E1-deleted virus have demonstrated that the persistence of circular intermediates in Hela cells is increased at 72 hours post-infection. These studies suggest that E2a DBP may augment circular intermediate formation and/or increase the stability of these structures by an unknown mechanism. E2a DBP may interact directly with circularized genomes and/or induce cellular factors which interact with sequences in these AAV genomes. Since DBP encodes an NLS, this protein may act to shuttle circular intermediates to regions of nucleus that allow for increased stability of these structures. NLS sequences have been shown to cooperatively interact with nucleolar targeting sequences and hence we will also evaluate if subnuclear targeting is important in maintaining the increased stability of circular intermediates containing ITR arrays. Furthermore, it is currently unknown where circular intermediates form in the cell and it remains plausible that they may form in the cytoplasm or nucleus. Hence, if DBP associates directly with circular intermediates, it may act as an NLS for DNA to enter the nucleus as well.

Several in vitro reconstitution models are used to investigate the interaction of circular intermediates with DBP and their affect on in vivo persistence following DNA transfection in Hela cells. Furthermore, results evaluating the affects of various mutant adenoviral vectors on circular intermediate and Rfm/Rfd formation have suggested that these two types of intermediates occur by independent pathways indicative of latent and lytic infection, respectively. In the setting of wild type AAV, circular intermediates may be pre-integration complexes, which in the presence of Rep, efficiently integrate into the host genome. In contrast, in the absence of Rep, circular intermediates may accumulate episomally in rAAV infected cells. To this end, methods of supplementing Rep function may be capable of enhancing integration of plasmid based delivery of AAV circular intermediates. Thus, experiments in which co-transfection of circular intermediate plasmids with Rep expression plasmids or mRNA are conducted.

To investigate whether DBP can augment the stability of circular intermediates by increasing targeting to the nucleus, a Hela cell line (gmDBP6) is utilized which encodes an inducible E2a gene under a dexamethasone responsible element. This cell line gives rise to high levels of DBP in nuclear extracts by Western blot following treatment with dexamethasone. gmDBP6 cells (+/−DEX) are transfected with various AAV circular intermediate plasmids containing 0, 1, 2, and 3 ITRs and total cellular and nuclear plasmid content evaluated by subcellular fractionation using Southern blotting against GFP probes. The time course of these studies is initially within the range of 12 hours to 4 days post-transfection. Transgene expression is evaluated by fluorometry (in cell lysates), and fluorescent microscopy (in viable cells), for GFP and luminescence for luciferase. Hela cells have demonstrated that immediate increases in transgene expression from AAV GFP circular intermediates as compared to control GFP plasmids occur as early as 24 hours post-transfection. Thus, certain cellular factors may facilitate an immediate accumulation of circular intermediates in the nucleus. DBP may invoke this increase by either direct interactions with ITR sequences or by the induction of cellular factors. To evaluate the potential for direct interactions between DBP and circular intermediates, various form of ITR arrays found within circular intermediates are end-labeled with $\gamma$-ATP$^{32}$ and evaluated for binding by electrophoretic mobility shift assays to nuclear extracts from gmDBP6 cells (+/−DEX). Supershifts, with DBP antibodies and competition experiments with cold ITR sequences and non-specific DNA, are used as controls for specific binding.

In a second model system aimed at evaluating the potential of DBP for shuttling and/or sequestering of circular intermediates to the nucleus, microinjection experiments in oocytes are performed with 50 ng of plasmid DNA of circular intermediates with and without 50 ng of DBP mRNA. Experiments initially evaluate the time course of GFP transgene expression (+/−DBP cRNA) by direct fluorescent microscopy. If major differences are seen, quantitative fluorometry of individual whole oocytes in 96 well plates is conducted. Similar studies on nuclear targeting in the presence of DBP can also be evaluated in this model by pooling microinjected oocytes for nuclear isolation and Southern blot analysis.

A third experimental model to evaluate nuclear targeting and/or accumulation of circular intermediate vectors in the presence and absence of DBP involves the microinjection of fluorescently labeled plasmid DNA into the cytoplasm and real time imaging to follow the nuclear accumulation of DNA. The DNA fluorescent dye, TOTO-1, is used to label DNA prior to injection. This dye forms an extremely stable complex with negligible diffusion and re-incorporation into nuclear DNA following transfection into polarized airway epithelial cell monolayers. Co-localization of DBP with wtAAV DNA genomes at focal hot spots within the nucleus supports the observation that nucleolar targeting may be important for persistence. These experiments are also performed in primary airway epithelial cells and in vivo models of the airway by either co-transfection of circular intermediates with DBP expressing plasmids and/or mRNA.

The effects of Rep co-transfection on the integration of circular intermediate plasmids is also evaluated. Two methods are used to express Rep including: 1) co-transfection with Rep expressing plasmids, and 2) co-transfection with Rep encoding mRNA. Initially, Hela, CFT1, and IB-3 cells are tested, as transformed cells may be more amenable to expansion and evaluation of integration. Both CFT1 and IB-3 cells represent airway epithelial cells. Experiments are performed by cationic liposome (GL-67) mediated transfection of circular intermediate DNA with varying doses of a Rep-containing expression vector, e.g., pCMVRep. The extent of integration is also evaluated by two criteria, Southern blotting of Hirt and genomic DNA and clonal expansion of GFP expressing cells. Since Southern blot has an approximate limit of sensitivity of 1 integrated plasmid molecule per 10 cellular genomes, clonal expansion may be necessary to evaluate persistence in less transfectable cells such as CFT1 and IB-3 cells. Cell lines are evaluated over the course of 1–10 passages.

Sustained expression of Rep by plasmid mediated co-transfection may be toxic to cells, hence co-transfection with Rep MRNA is also evaluated. Cationic liposome:mRNA mediated transfection has been previously shown to work in cell lines and although the level of expression is much more transient than for DNA, in these studies it may be an advantage. Initial studies are performed with in vitro transcribed Rep mRNA alone to evaluate the $\mu$g amount of mRNA needed for Rep expression as determined by Western blot. Once the threshold for detectable Rep expression is established, increasing amounts of Rep mRNA are co-transfected with circular intermediate DNA. Similar assays are used as described above to evaluate the extent of AAV circular intermediate integration. If findings suggest that increased integration if facilitated by Rep, the site specificity of this integration can be evaluated by cloning GFP expressing cells after the 10th passage by serial dilution. These GFP expressing clones are expanded and genomic Southern blots assessed with both GFP and AVS1 specific probes. By evaluating a number of restriction enzymes which either do not cut or cut once within the circular intermediate plasmid, it will be determined whether integration has occurred at the AVS1 loci.

To test whether secondary structure rather than primary sequence is the important determinant of increased episomal stability of AAV circular intermediates, synthetic DNA sequences are generated with identical secondary structure to several ITR arrays in circular intermediates. The primary sequence is completely altered and bares no resemblance to sequences contained within native AAV ITRs. These synthetic DNA sequences are tested for their ability to confer increased episomal stability to heterologous plasmids in several model systems including: 1) the airway, 2) muscle, 3) and developing *Xenopus* embryos. The developing *Xenopus* embryo model is ideal for testing integration and persistence of plasmid based vectors for application of in utero gene therapy. If synthetic DNA sequences with similar secondary structure to ITRs are found to confer increased persistence to plasmid based vectors, then determinants for protein binding which facilitate persistence are independent of primary base sequence. These studies allow the optimization of the secondary structural requirements by synthesizing a wide range of DNA molecules with varying degrees of palindromic repeats. Furthermore, the secondary structure may not bind proteins directly but facilitate recombination of plasmids to large concatamers which have increased episomal stability or enhanced integration efficiencies.

EXAMPLE 5
Delivery of Multiple Genes through Intermolecular Concatamerization Methods
Recombinant AAV Vectors.

Two rAAV vector stocks were generated for use in these studies, AV.GFP3ori (Example 1) and AV.Alkphos (also known as CWRAPSP, a gift of Dusty Miller) (Halbert et al., 1997). Virus stocks were generated by co-transfection of 293 cells with either pCisAV.GFP3ori or pCWRAPSP along with pRep/Cap, followed by co-infection with recombinant Ad.CMVlacZ helper virus (Example 2). rAAV was then purified through three rounds of CsCl density gradient centrifugation as previously described byDuan et al. (1997). Purified viral fractions were heated at 60° C. for 1 hour to inactivate any residual contaminating helper adenovirus. The yields for AV.GFP3ori and AV.Alkphos were $1\times10^{12}$ and $7\times10^{11}$ particles per ml, respectively, as determined by slot blot hybridization with $^{32}$P-labeled GFP or Alkphos probes. Infectious titers determined by infection of 293 cells with rAAVs were $1.1\times10^9$ IU/ml (AV.GFP3ori) or $8.6\times10^8$ IU/ml (AV.Alkphos). Controls testing for contamination of rAAV stocks with wtAAV by anti-Rep immunocytochemical staining in rAAV/Ad.CMVlacZ co-infected 293 cells were negative (limit of sensitivity is less than 1 infectious wtAAV particle per $10^{10}$ DNA particles of rAAV). Similarly, histochemical staining for $\beta$-galactosidase in rAAV infected 293 cells showed no detectable contamination with helper adenovirus in $10^{10}$ DNA particles of rAAV (limit of sensitivity).

Infection of Muscle Tissue and Evaluation of Transgene Expression.

The C57BL/6 mice used for these experiments were housed in a virus-free animal care facility and were maintained under strict University of Iowa and NIH guidelines, using a protocol approved by the Animal Care and Use Committee and facility veterinarians. Four to five week old mice received bilateral 30 $\mu$l injections of a mixture of both AV.GFP3ori and AV.Alkphos into the tibialis anterior muscle ($5\times10^9$ DNA particles of each virus per muscle). Controls included uninjected muscles and muscles receiving injections of one of the viruses alone. At 14, 35, 80, and 120 days post-infection, animals were euthanized and tissues were harvested for evaluation of transgene expression and preparation of low molecular weight Hirt DNA. For each experimental time point, at least 3 independently injected muscles were evaluated.

In all experiments, GFP fluorescence was visualized in freshly excised muscle tissue prior to processing. A portion of the same muscle was fixed with 2% paraformaldehyde in phosphate buffered saline, and cryoprotected in graded sucrose solutions before embedding in optimal cutting temperature medium (OCT). Sections (6 $\mu$m) were then evaluated for GFP expression directly and Alkphos expression following heat inactivation of endogenous Alkphos and histochemical staining for Alkphos activity (Engelhardt et al., 1995). To confirm dual localization of GFP and Alkphos expression in the same muscle fibers, either serial sections were evaluated for GFP and Alkphos expression or the same section was first photographed for GFP expression followed by histochemical staining for Alkphos and re-imaging of the same field.

Rescue of Circular Intermediates from Muscle Hirt DNA.

Low molecular weight Hirt DNA was prepared from 20 mg specimens of injected muscles from 3 animals at each time point (Example 2). Hirt DNA (4 $\mu$l; ⅕ of the total volume) was then used to transform 50 $\mu$l of electrocompetent SURE cells (Stratagene) using a BioRad *E. coli* electroporater and 0.1 $\mu$m cuvettes. Colonies resulting from each bacterial transformation were quantified, and plasmids from 20 colonies from each muscle Hirt DNA sample were purified for analysis. It should be noted that only circular forms carrying the Amp resistance gene and the bacterial origin of replication from AV.GFP3ori are rescued by bacterial transformation (Duan et al., 1998). Control experiments reconstituting $5 \times 10^{10}$ viral DNA particles into uninfected muscle extracts prior to Hirt DNA preparation failed to give rise to replication competent plasmids in the rescue assay (Duan et al., 1998). Additional controls in Duan et al. (1998) using AV.GFP3ori virus also demonstrated that linear double stranded and single stranded purified viral DNA genomes do not give rise to replication competent plasmids following transformation into *E coli*.

Characterization of Encoded Genes in Rescued Circular Intermediates.

Several assays were used to characterize the extent of intermolecular recombination between independent circular viral genomes by evaluating the number and type of encoded genes in rescued plasmids from Hirt DNA of muscles co-infected with AV.GFP3ori and AV.Alkphos. Initial analysis involved the bulk evaluation of 60 rescued plasmids (20 from each of three muscle samples for each time point) by dot blot hybridization of mini-prep DNA with EGFP, Alkphos, and Amp $^{32}$P-labeled DNA probes. In these studies, Amp hybridization served as a control to show that there was a sufficient quantity of DNA for the analysis. The percentages of Alkphos and/or GFP hybridizing plasmids were calculated by this method for each muscle sample. From this percentage, the total number of plasmids hybridizing to each probe in the Hirt DNA sample was calculated from the total CFU obtained in each transformation. In this analysis, each muscle sample was evaluated independently to determine the mean (+/−SEM) total Alkphos and/or GFP hybridizing plasmids. A second evaluation involved the transfection of rescued plasmids into 293 cells using lipofectamine, followed by evaluation of GFP fluorescence and histochemical staining for Alkphos. To confirm that GFP and Alkphos co-expressing plasmids were indeed clonal and that both genes were encoded on the same plasmid, a selected group of five co-expressing plasmids were retransformed into *E. coli* and colonies were re-isolated prior to repeating the transfection studies. In all cases, plasmids co-expressing the two reporter genes remained clonal through this subsequent re-isolation.

Structural Analysis of Concatamer rAAV Circular Intermediates.

To further characterize the nature of isolated circular intermediates co-expressing both GFP and Alkphos transgenes, plasmid structure was mapped by Southern blotting and restriction enzyme analysis. The structural of five co-expressing circular intermediate plasmids were determined by digestion with AhdI, HindIII, NotI, HindIII/NotI, ClaI/AseI, and/or SnaBI and Southern blotting was performed with $^{32}$P-labeled GFP, Alkphos, and ITR probes.

Results

Strategy for Characterizing Mechanisms of rAAV Circular Intermediate Formation.

Figure 14A:
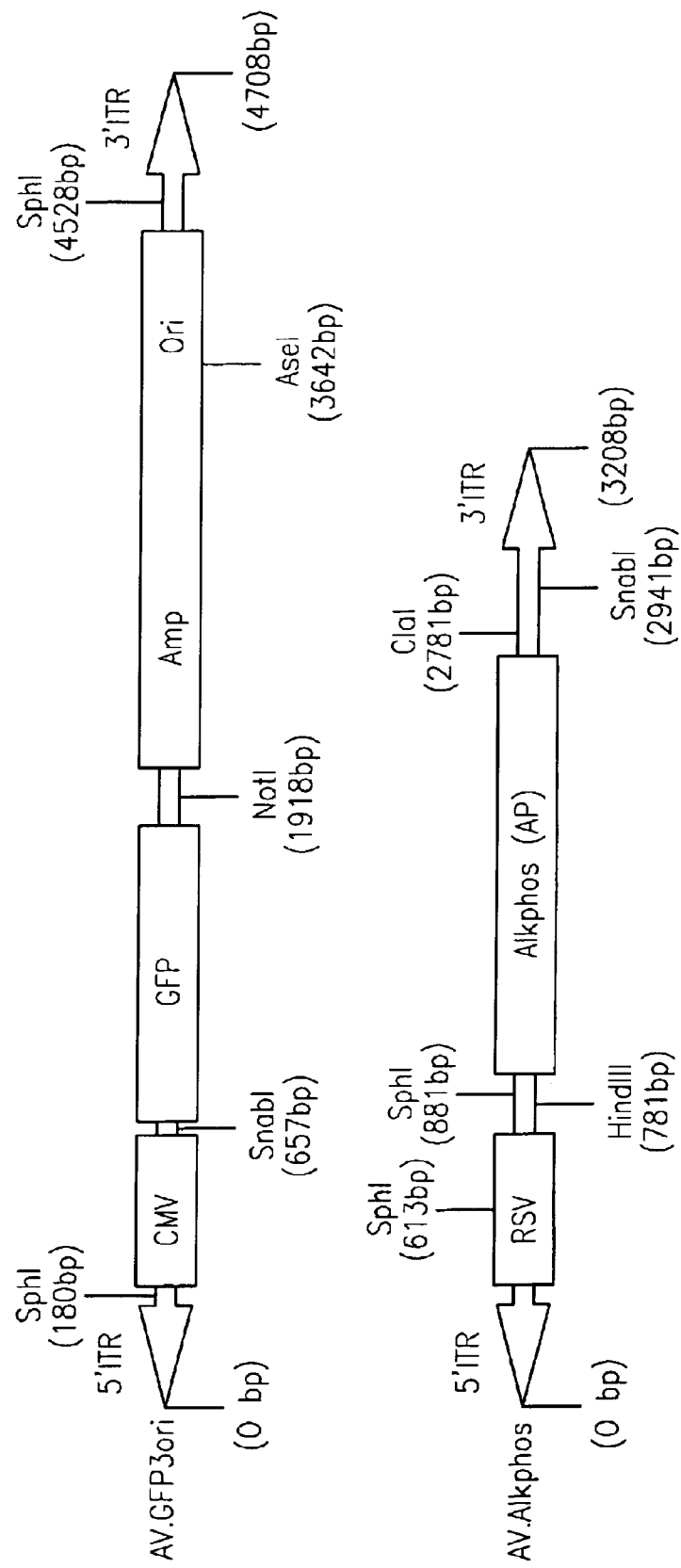
FIG. 14(Parts A–C). Mechanistic scheme for determining pathways for rAAV circular concatamer formation. The two independent vectors used in these studies, AV.Alkphos and AV.GFP3.ori, are shown in Panel A. Restriction sites important in the structural analysis of circular intermediates are also shown. In Panel B, a schematic representation of two potential models for circular concatamer formation is depicted, along with the methods to experimentally differentiate which of these processes is active in muscle. Following co-infection of the tibialis muscle with AV.Alkphos and AV.GFP3.ori, all subsequently rescued plasmids arise solely from circular intermediates containing AV.GFP3ori genomes. If rolling circular replication is the sole mechanism of concatamerization, only GFP expressing plasmids should be rescued. In contrast, if intermolecular recombination between independently formed monomer circular intermediates is the mechanism of concatamerization, both GFP and GFP/Alkphos expressing plasmids should be rescued.
Figure 14B:
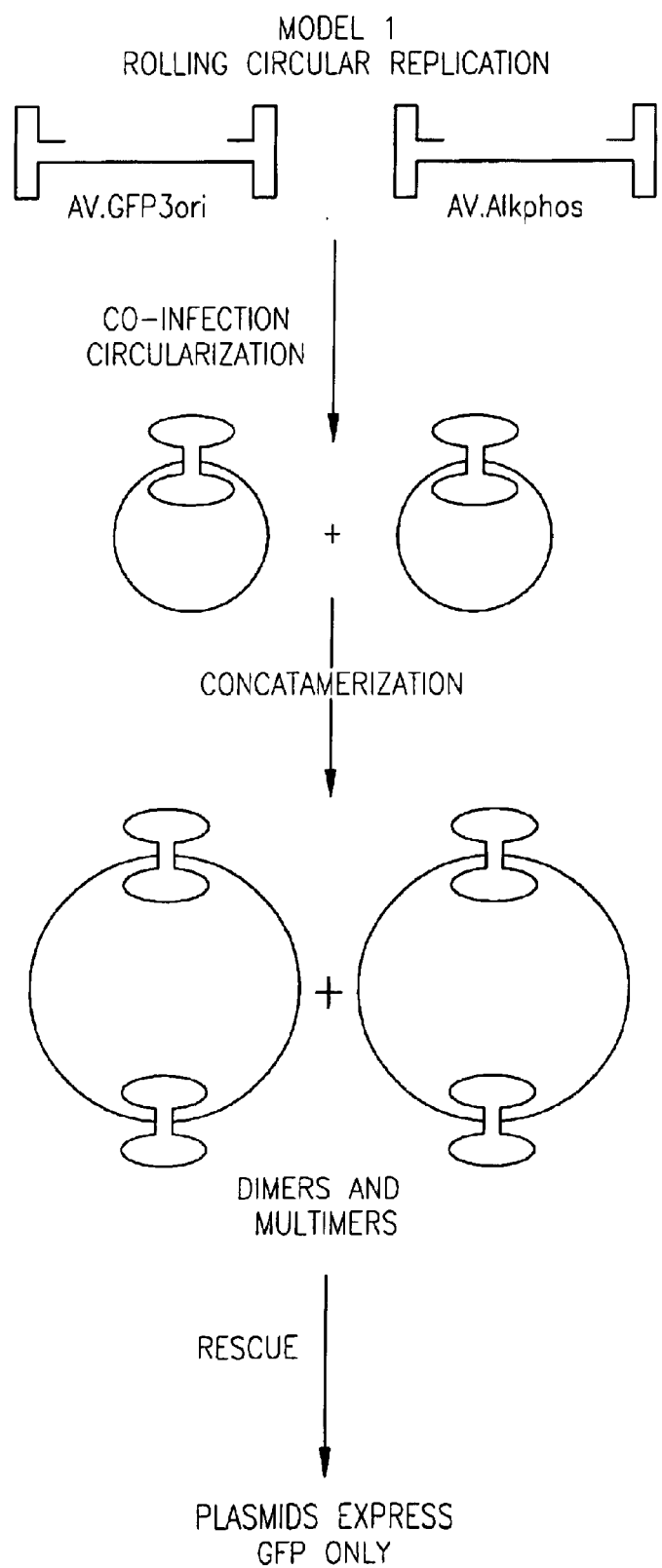
Figure 14C:
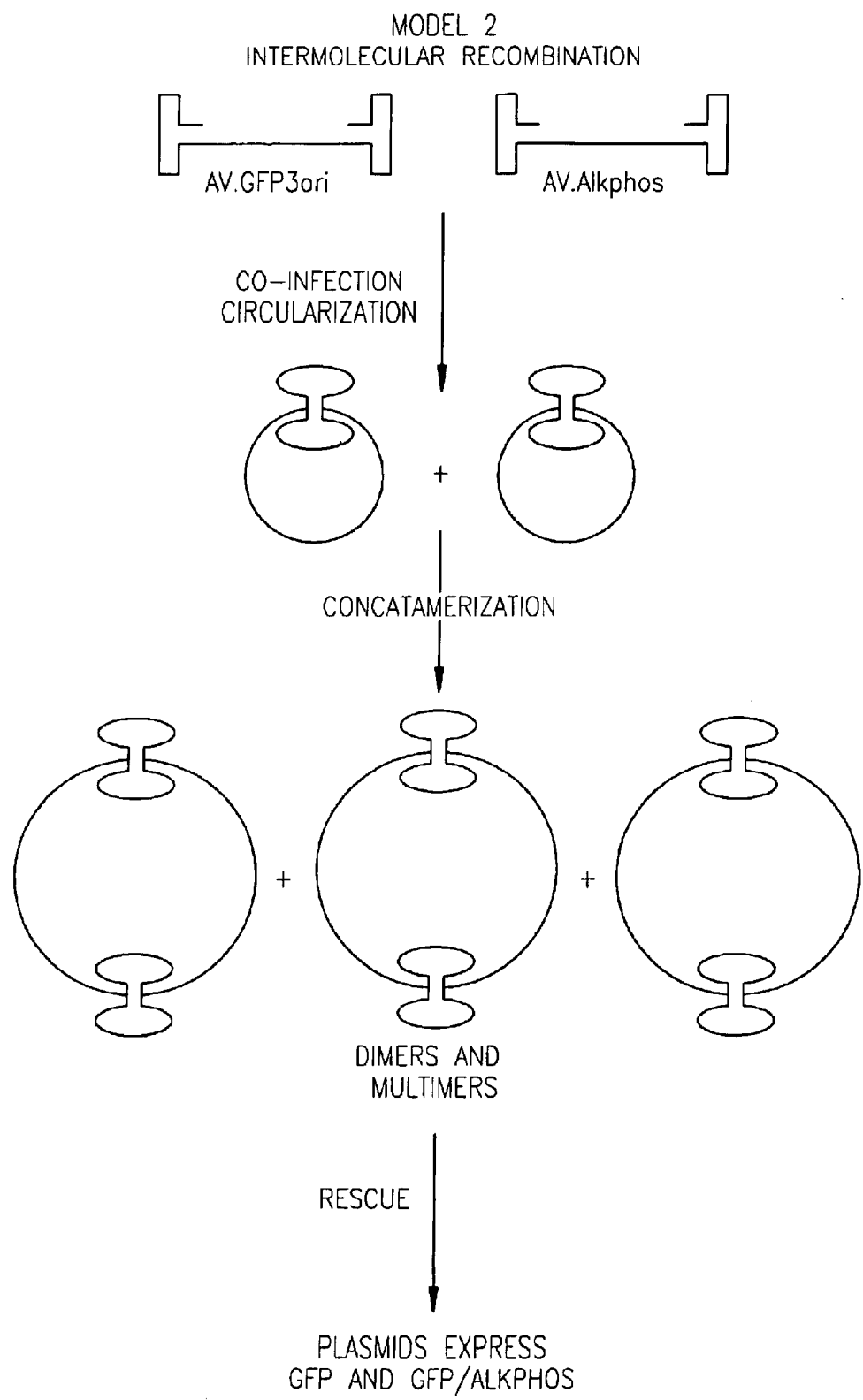

Efficient circularization of rAAV genomes has been previously demonstrated to occur in muscle in a time dependent fashion (Example 2). Furthermore, the conversion of monomeric to multimeric circular rAAV intermediates occurred over time and was associated with long-term episomal persistence of AAV genomes. High molecular weight AAV circular genomes might form by either of the following two mechanisms, one involving the replication of monomer structures and the other through intermolecular recombination between independent monomers. A rescue assay was developed using two separate rAAV vectors, AV.GFP3ori and AV.Alkphos (FIG. 14A), which allowed for the identification of independent viral genomes through unique transgenes. In this assay, circular form genomes were rescued in bacteria by virtue of Amp/ori sequences encoded in one of the two vectors (AV.GFP3ori). A method for characterizing the extent of intermolecular recombination between independent circular rAAV genomes was shown in FIG. 14B.

Co-expression of Independently Encoded rAAV Transgenes in Muscle Myofibers.

Figure 15C:
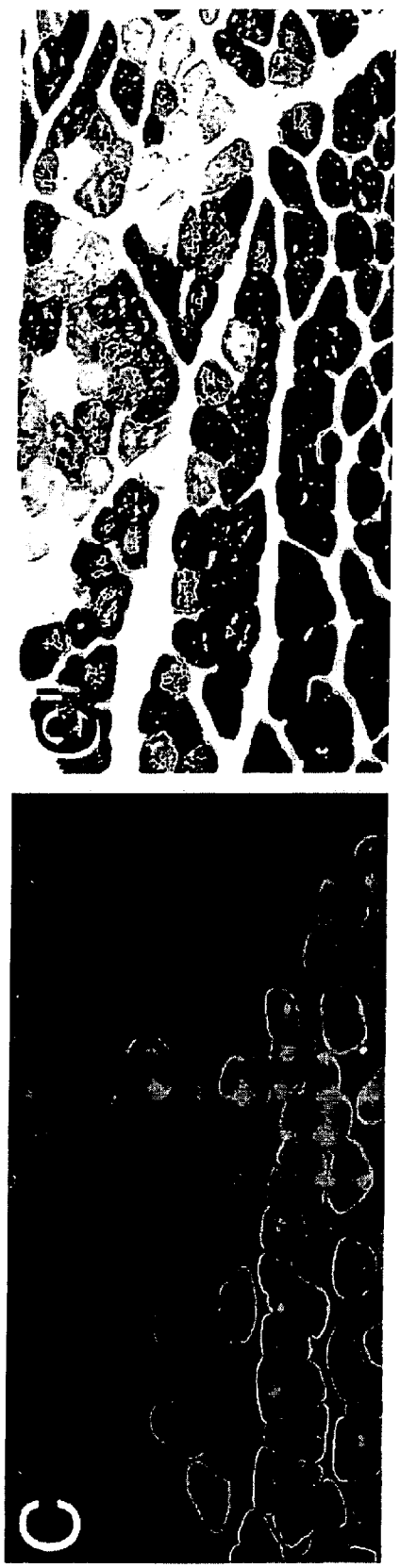
FIG. 15(Parts A–D). Co-infection of tibialis muscle of mice with AV.Alkphos and AV.GFP3ori. Transgene expression of rAAV infected tibialis muscle was determined at 14, 35, 80 (Panels A and A'), and 120 (Panels B–D) days following co-infection with $5 \times 10^9$ DNA particles each of AV.Alkphos and AV.GFP3ori. The time course of transgene expression started around 14 days and peaked by 35–80 days. The extent of co-infection of myofibers with both Alkphos and GFP rAAV was determined in serial sections of 80 and 120 day post-infection muscle samples. Panels A–C represent GFP fluorescence of formalin fixed, cryoprotected sections, while panels A'–C' depict the histochemical staining for Alkaline phosphatase in adjacent serial sections. A short staining time (7 minutes) was necessary to observe variation in staining levels for comparison to GFP. It was found that longer staining times (30 minutes) saturated the Alkphos signal. The boxed region in panels B and B' are enlarged in panels C and C', respectively. A more precise correlation of GFP and Alkphos staining in myofibers is given in Panel D in which co-localization of GFP and Alkphos expression was examined in the same section of a 120 day post-infected sample. This was performed by photographing the GFP fluorescent image prior to staining for Alkphos activity. The left panel of D shows a high power Nomarski photomicrograph of a group of myofibers (traced in red), while the corresponding GFP and Alkphos staining patterns are shown in the right panel. Photomicrographs of Alkphos staining were taken with a red filter to allow for superimposition of staining patterns with GFP fluorescence. Co-expression of Alkphos and GFP is shown within myofibers as a yellow/orange color. Myofibers are marked as follows: (−) negative for both Alkphos and GFP, (*) positive for only GFP, and (+) positive for both GFP and Alkphos.

To confirm that myofibers can be co-infected at a high efficiency with the two rAAV vectors, the tibialis anterior muscle of mice was co-infected with $5 \times 10^9$ DNA particles of both AV.GFP3ori and AV.Alkphos. At 14, 35, 80, and 120 days post-infection, muscles were harvested and analyzed for transgene expression. Transgene expression from both reporters was weak but clearly visible in 14 day muscle samples. By 80 days post-infection, transgene expression was maximal and serial sections demonstrated expression of both Alkphos and GFP transgenes in overlapping regions of the muscle (FIGS. 15A–C). At this time point, approximately 50% of the fibers in the tibialis muscle expressed both transgenes. To confirm that co-infection of myofibers occurred with the two independent vectors, co-localization studies were performed on muscle sections by a serial staining procedure. These studies, depicted in FIG. 15D, demonstrate four classes of myofiber transgene expression: 1) GFP positive only, 2) Alkphos positive only, 3) GFP/Alkphos positive, and 4) no transgene expression. The largest fraction of myofibers expressed both GFP and Alkphos transgenes. These results confirm that at the titers of virus used for infection, co-infection occurred in greater than 90% of transgene expressing myofibers.

Rescue of Bi-functional rAAV Circular Intermediates Increases Over Time.

Figure 16A:
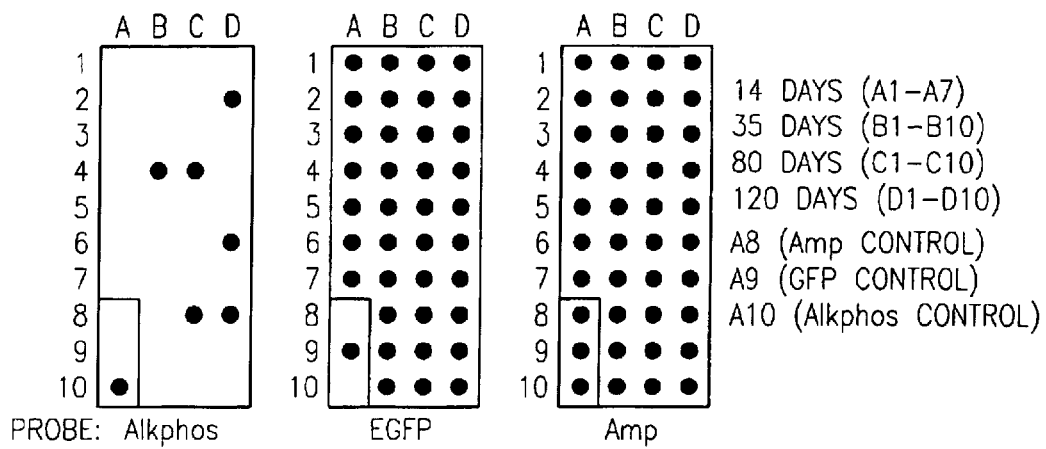
FIG. 16(Parts A–C). Rescue of circular intermediates and characterization of DNA hybridization patterns. Using the ampicillin resistance gene (amp) and bacterial ori incorporated into the AV.GFP3ori vector, the extent of circular intermediate formation was assessed by rescuing amp resistant plasmids following transformation of ⅕ the isolated Hirt DNA into E. coli Sure cells. Twenty plasmids from each muscle sample were prepared and analyzed by slot blot hybridization against GFP, Alkphos, and Amp $^{32}$P-labeled DNA probes. A representative group demonstrating the hybridization patterns is shown in Panel A. Panel B depicts the mean (+/−SEM) number of rescued bacterial plasmids that hybridized to either GPF alone, or to both GFP and Alkphos probes, following transformation of ⅕$^{th}$ of the Hirt DNA. These numbers were calculated from the percentage of plasmids hybridizing to GPF and/or Alkphos and the total CFU plating efficiency derived from the original transformation. In total, 3 independent muscle samples were analyzed for a total of 60 plasmids at each time point. The percentage of GFP hybridization positive rescued plasmids that also demonstrated hybridization to Alkphos is shown in Panel C. These data demonstrate an increase in the abundance of rescued GFP/Alkphos co-encoding circular intermediates over time.
Figure 16B:
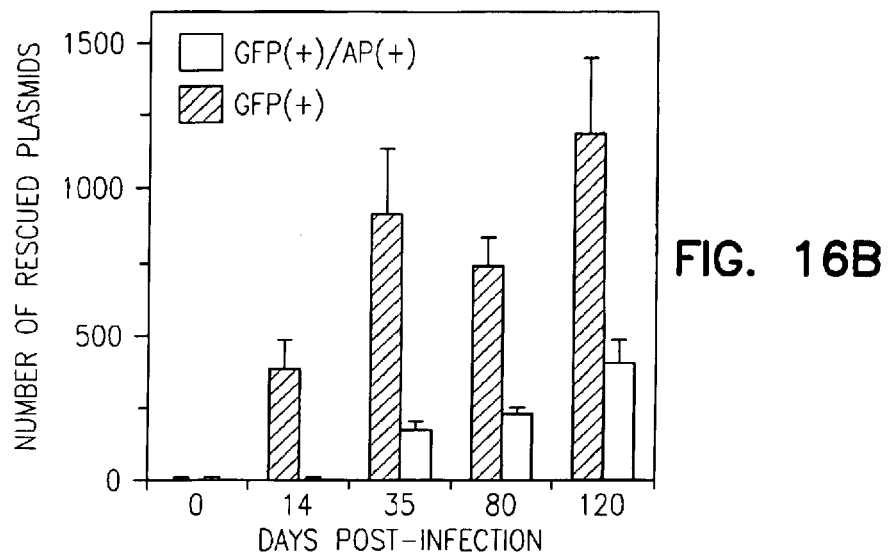
Figure 16C:
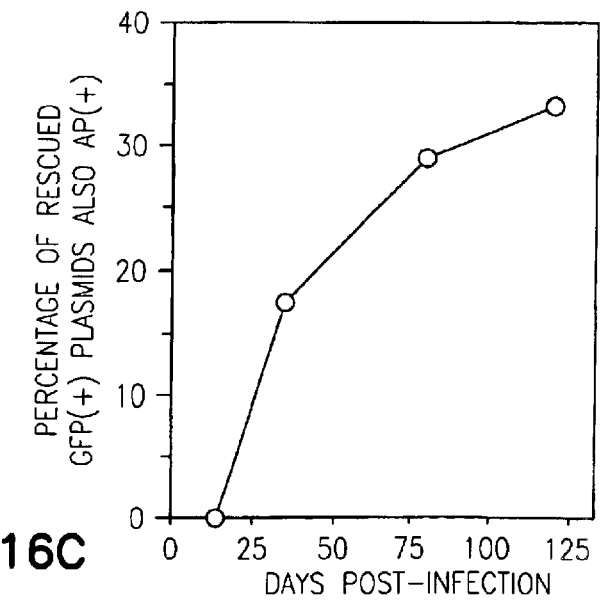

To determine the extent of recombination between circular AAV genomes, circular form genomes were rescued as plasmids from low molecular weight Hirt DNA of muscle tissue co-infected with AV.GFP3ori and AV.Alkphos. Following transformation of *E.coli* Sure cells with Hirt DNA purified from infected muscles, the total number of GFP and Alkphos hybridizing Amp resistant bacterial plasmids was quantitated for each time point post-infection (FIG. 16A and B) (Duan et al., 1995), the abundance of circular AAV genomes rescued from AV.GFP3ori increased over time. For each muscle sample (three for each time point) twenty plasmid clones were evaluated for hybridization to GFP and Alkphos DNA probes and the total number of plasmids was back calculated from the total CFU for each individual muscle sample. FIG. 16B demonstrates the mean (+/−SEM, N=3) total plasmids that hybridized to GFP or GFP/Alkphos probes at each time point. At 14 days post-infection, GFP/Alkphos co-hybridizing plasmids were never observed. In contrast, at time points after 35 days the percentage of GFP/Alkphos co-hybridizing plasmids increased with time and reached 33% by 120 days (FIG. 16C). Since bacterial plasmid rescue can only occur through AV.GFP3ori genomes, this data suggests that recombination between independent Alkphos and GFP rAAV genomes takes place over time. These results are consistent with studies described hereinabove demonstrating a time dependent concatamerization of monomer circular rAAV genomes in muscle.

Figure 17A:
FIG. 17(Parts A–C). Transgene expression from rescued circular intermediates. Rescued circular intermediate plasmids were transfected into 293 cells for assessment of their ability to express encoded transgenes. In these studies all GFP hybridization positive clones from at least two muscles were tested for each time point and scored for their ability to express GFP and Alkaline phosphatase. In total at least 40 clones were evaluated for each time point. Three patterns of transgene expression were observed following transfection of these plasmids: I) no gene expression (Panel A), II) GFP expression only (Panel B), and III) GFP and Alkphos expression (Panel C). Panels A–C depict Nomarski photomicrographs (left) of GFP fluorescent fields (center) and Alkphos staining of a different field from the same culture (right). The percentage of GFP hybridization positive clones that also expressed GFP is shown in Panel D. Additionally, this panel illustrates the percentage of GFP expressing clones also expressing Alkphos.
Figure 17B:
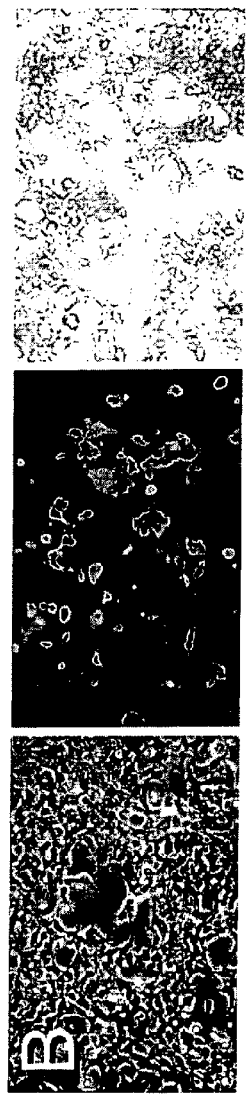
Figure 17C:
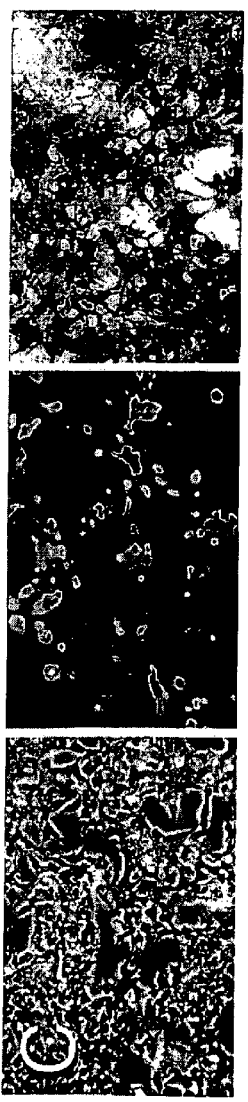
Figure 18A:
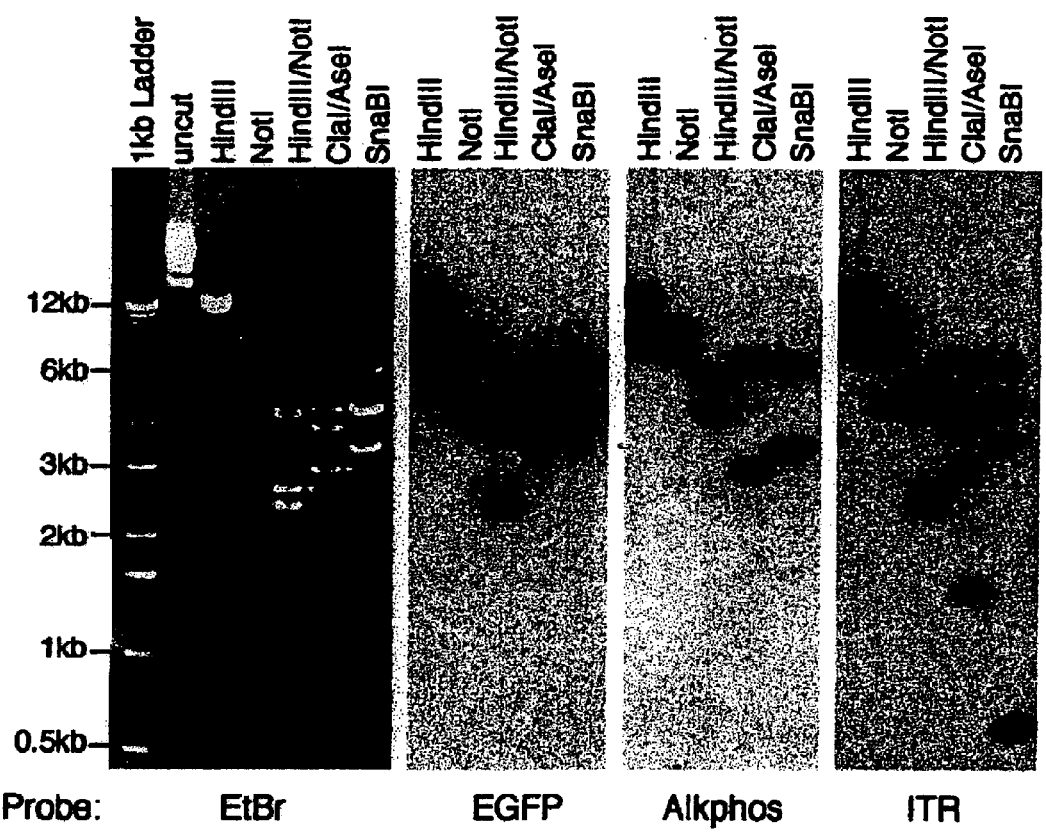
FIG. 18(Parts A–D). Structural analysis of bi-functional concatamer circular intermediates. To filly characterize the nature of GFP and Alkphos co-expressing circular intermediates, detailed structural analyses were performed using restriction enzyme mapping and Southern blot hybridization with GFP, Alkphos, and ITR $^{32}$P-labeled probes. Results from Southern blot analysis of plasmid clone #33 (Panel A) and clone #5 (Panel C) are given as representative examples of circular intermediates isolated from 80 and 35 day Hirt DNA of rAAV infected muscle, respectively. Agarose gels were run in triplicate for each of these clones and Southern blot filters were hybridized with one of the three DNA probes as indicated below each autoradiogram. Molecular weights (kb) are indicated to the left of the ethidium stained agarose gel and restriction enzymes are marked on the top of each gel/filter. Panels B and D give the deduced structure of plasmid clones #33 and #5, respectively, as based on Southern blot analysis. For ease of comparison with the restriction maps of the viral genomes given in FIG. 14A, the position of restriction enzyme sites (kb) are marked with the indicated orientation of intact viral genomes. However, in clone #33 a deletion occurred between the AseI and HindIII site of a head-to-tail array between AV.Alkphos and AV.GFP3ori, as reflected by a 900 bp reduction in the anticipated size of HindIII/NotI and ClaI/AseI fragments (marked by asterisks in Panel A). Furthermore, the SphI site flanking an ITR was ablated in clone #5 (bands effected by this deletion are marked by asterisks in Panel C). The deletion is not reflected in the overall concatamer since the exact region involved and/or the size of the deletion is unclear. Additionally, chemical sequence evidence of rescued circular intermediates suggests that the predominant form of ITR arrays may be in a double-D structure (ie., one ITR flanked by two D-sequence rather than two ITRs) and hence ITR arrays containing fragments may appear 147 bp shorter than indicated. However, to more easily depict the orientation of viral genomes, the position of 5 ' and 3' ITRs is indicated rather than representing a single ITR at these junctions.
Figure 18B:
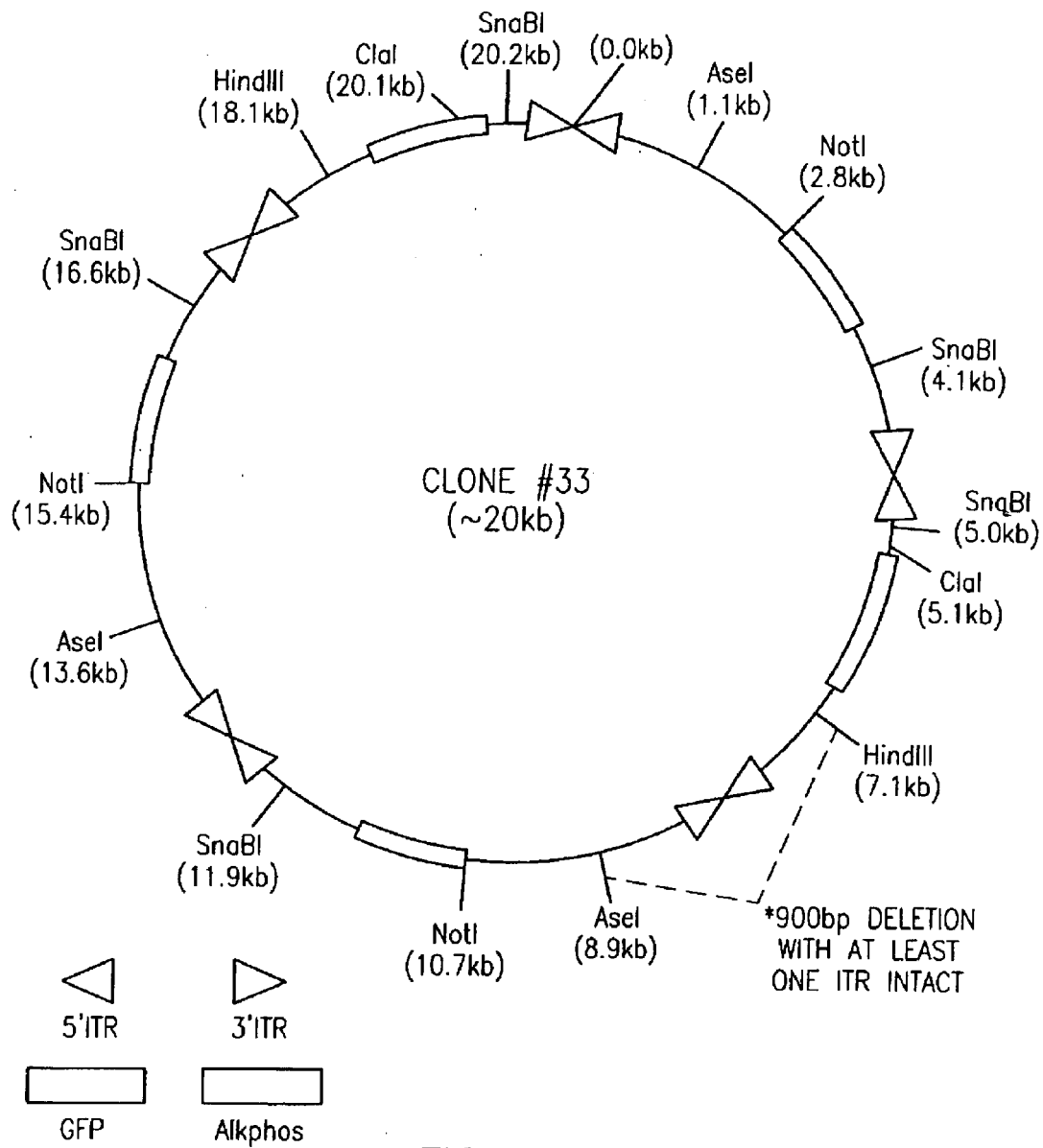
Figure 18C:
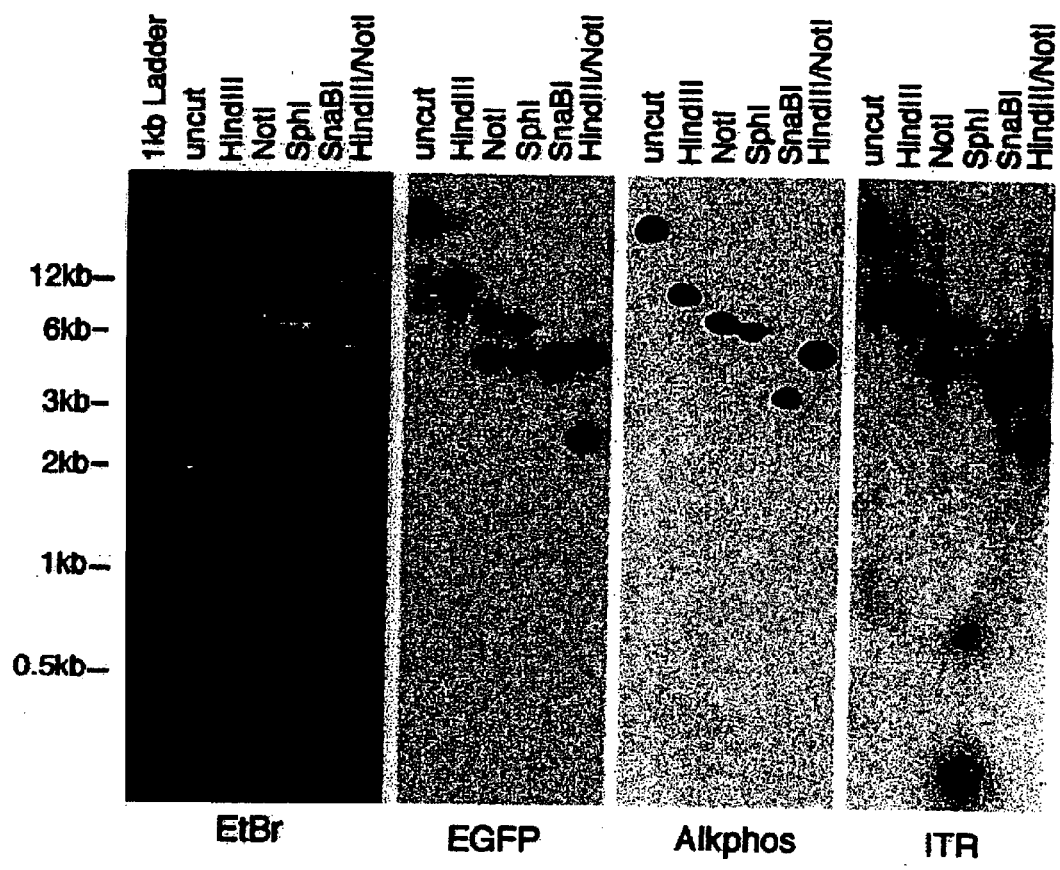
Figure 18D:
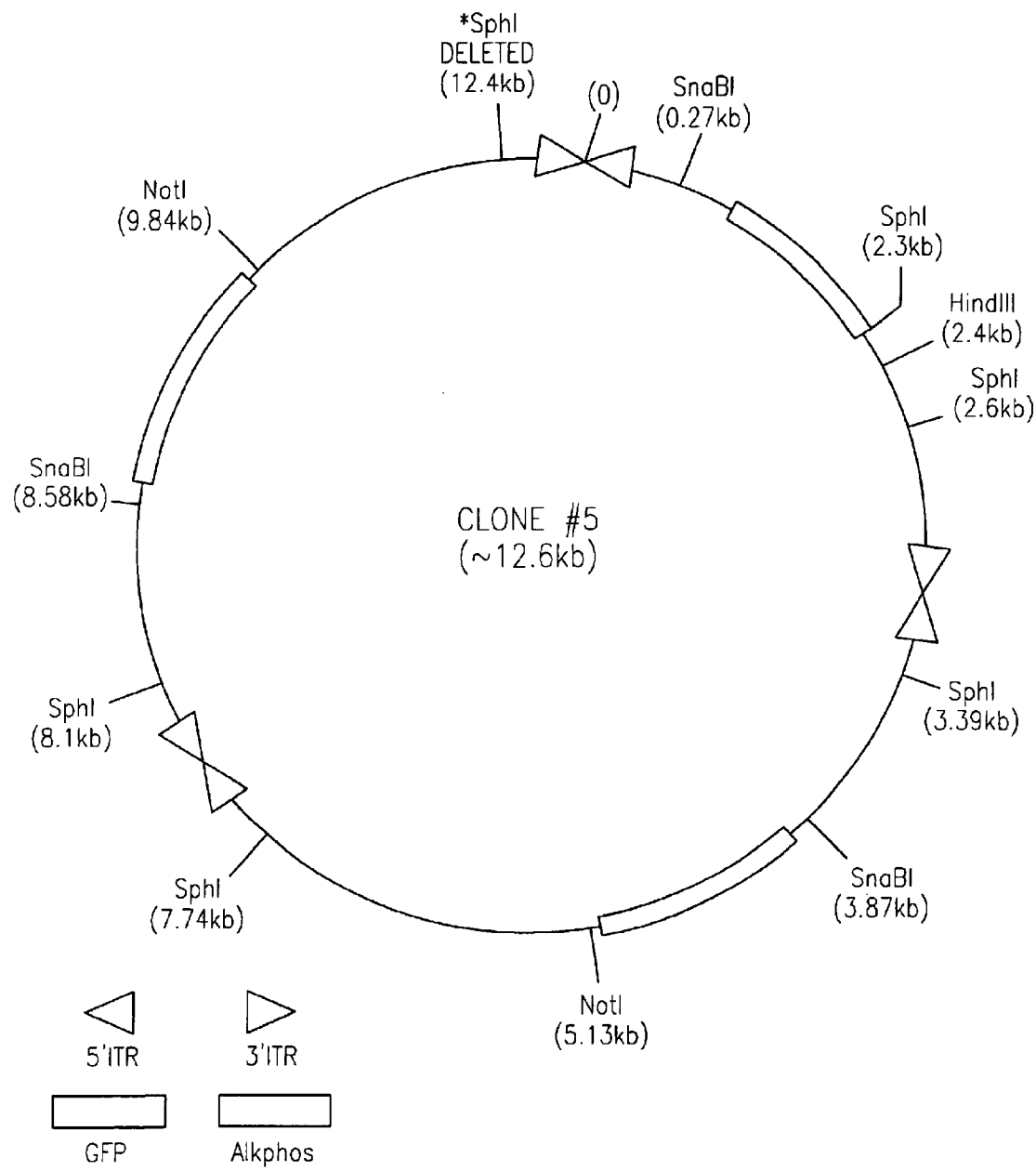

To evaluate the ability of circular intermediates to express encoded transgenes, transient transfection studies were performed in 293 cells with rescued circular intermediate plasmids (FIGS. 17A–C). Between 85–90% of rescued plasmids hybridizing to GFP probes on slot blots also expressed the GFP transgene in this transfection assay (FIG. 17D). The percentage of GFP expressing plasmids that also expressed Alkphos rose over time in concordance with the hybridization data (FIG. 17D). However, approximately 40–50% of plasmids which were hybridization positive for Alkphos did not express the Alkphos transgene. This may represent recombinational deletion of the RSV promoter driving Alkphos expression which occurred during concatamerization at sites near the 5' ITR. These results demonstrate that intermolecular recombination between Alkphos and GFP derived circular intermediates occurs as part of the time dependent concatamerization process of rAAV in muscle. To confirm that amplified plasmids stocks expressing both reporter genes were actually clonal (i.e., one plasmid rather than two independent plasmids resulting from contamination), a select number of bacterial clones expressing both transgenes were re-isolated and the transfection assays were repeated. In all cases, plasmids expressing the two reporter genes remained clonal through two rounds of bacterial cloning. Hence, dual reporter expression was not due to contamination of independent GFP and Alkphos expressing plasmids.

Concatamerization of AAV Circular Intermediates Occurs Through Uniform Intermolecular Recombination Between ITRs of Independent Viral Genomes.

To better understand the mechanisms of circular concatamer formation, a detailed structural analysis was performed of five bi-functional circular concatamers isolated from rAAV infected muscle samples. As previously described for the AV.GFP3ori genome (Example 2), the conversion of monomeric circular AAV genomes to large multimeric circular concatamers with a predominant head-to-tail structure increased with time in muscle. To evaluate the structure of bi-functional circular concatamers, restriction enzyme mapping and Southern blot analysis using $^{32}$P-labeled EGFP, Alkphos, and ITR probes was employed. Results from five analyzed plasmids demonstrated between 3–6 genomes within these circular concatamers. Two representative structures from 35 and 80 day time points are shown in FIG. 18. Several interesting conclusions can be made from this structural analysis. As described, head-to-tail oriented genomes could be seen in all isolated concatamers. However, several examples of head-to-head and tail-to-tail genome combinations of AV.Alkphos and AV.GFP3ori were also seen. Since head-to-head and tail-to-tail genome concatamers were never seen in muscles infected with AV.GFP3ori alone, there must be a selective disadvantage for bacterial replication when ori sequences are in either of these conformations. However, since the AV.Alkphos genomes do not contain a bacterial origin of replication, this orientation is permitted in chimeric concatamers. Second, noticeable deletions and/or loss of restriction sites close to ITRs were noted (FIG. 17). It is not known whether deletions close to the ITR are a common event in the concatamerization process, but if so, this could account for the fact that only 60% of GFP/Alkphos hybridizing circular intermediates also expressed the Alkphos transgene.

Discussion

Concatamerization of rAAV genomes has long been recognized in integrated proviral genomes. Recently, the association of this concatamerization process with the formation of high molecular circular genomes in muscle has suggested that this process may also be important in episomal persistence. The findings described herein demonstrated rescue of independent viral genomes within the same circular concatamer, suggesting that this process of concatamerization occurs through intermolecular recombination. Furthermore, at 14 days the predominant form of viral genome in muscle was circular monomers (Example 2), which correlates with the results described above demonstrating only GFP expression in rescued circular intermediates at this time point. Together with the fact that bi-functional rescued circular concatamners increase with time, these results suggest that large concatamers form by recombination of monomeric circular precursor genomes. Furthermore, since an alternative model of concatamerization by rolling circular replication would be expected to yield only GFP expressing rescued plasmids in this system, this mechanism does not appear responsible for concatamerization.

Based on the structural analysis of these bi-functional circular intermediates, recombination between monomeric circular rAAV genomes is likely facilitated through ITR sequences. Directionality of this recombinational event does not appear to play a significant role, since head-to-tail, head-to-head, and tail-to-tail oriented intermolecular concatamers were found. In addition, the extent to which recombination within ITR repeat regions occurs in bacteria is presently unknown and may account for the deletions and/or restriction site losses near ITR arrays. However, serial passaging of bi-functional circular AAV genomes in bacteria has suggested that the structure of these large concatamers is impressively stable in bacteria.

Figure 19A:
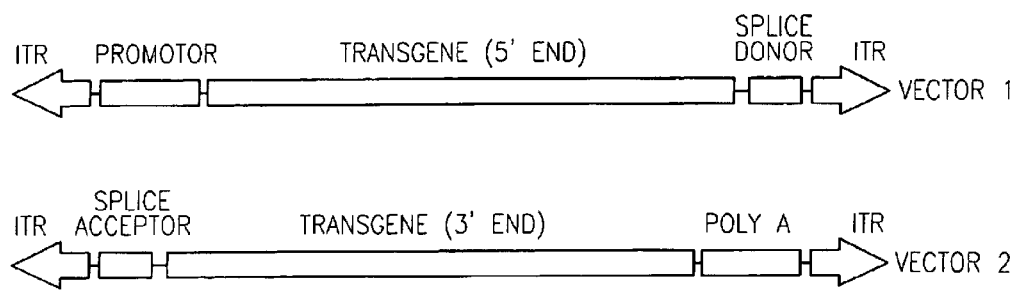
FIG. 19(Parts A–B). Application of rAAV circular concatamers to deliver vectors with large gene inserts. Panel A depicts two rAAV vectors encoding two halves of a cDNA (red) flanked by splice site consensus sequences (brown). Panel B depicts one potential type of intermolecular concatamer following co-infection of cells with the independent vectors shown in panel A. Full length transgene mRNA can then be produced by splicing between these two vector encoded sequences within circular concatamers.
Figure 19B:
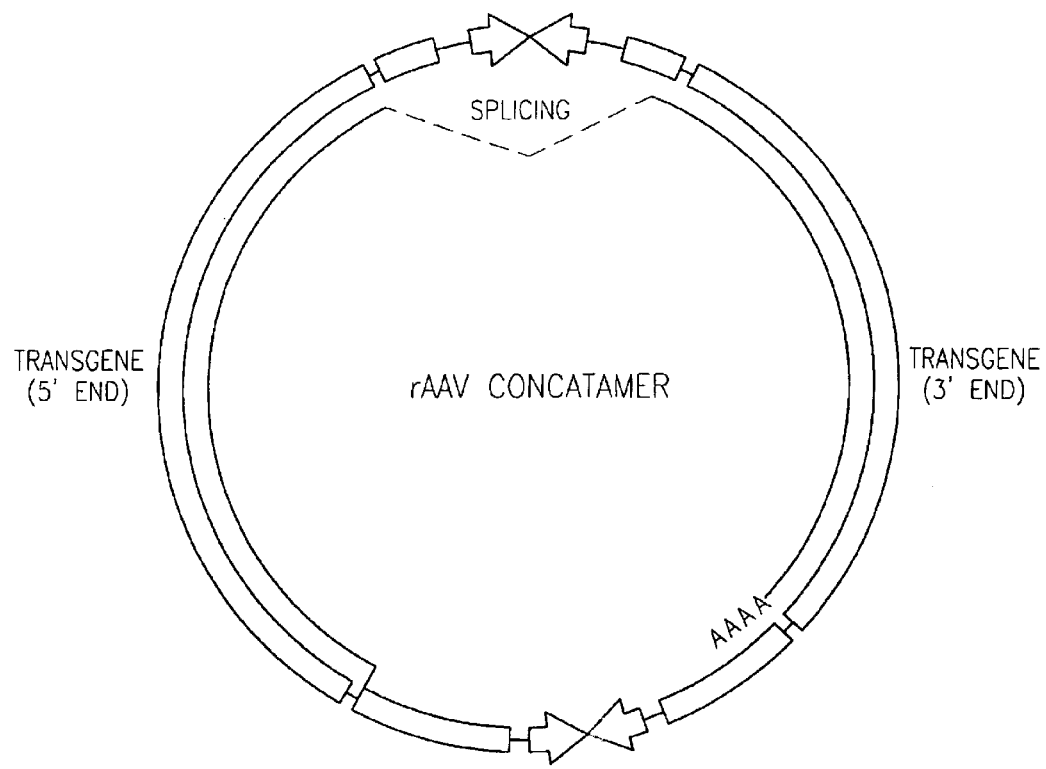

Intermolecular recombination of rAAV genomes to form single circular episomes may be particularly useful for gene therapy. For example, large regulatory elements and genes beyond the packaging capacity of rAAV may become linked after co-infecting tissue with two independent vectors (FIG. 19). This strategy could also involve splicing of transcripts from vectors encoding two independent regions of a gene which are brought together to form an intact splicing unit by circular concatamerization.

For example, two independent vectors encoding two halves of the CFTR gene flanked by donor and acceptor splice site sequences are prepared. Expression of functional CFTR protein results after splicing of RNA transcribed from a concatamerized genome comprising both halves of the gene in the sense orientation. One rAAV vector may comprise the first 3.3 kb of the CFTR gene under the control of the RSV promoter and an in-frame splice donor site at the 3' end of the CFTR cDNA. The second rAAV vector encodes a splice acceptor intronic sequence, the 3' 1.4 kb of the CFTR gene, and SV40 poly-adenylation sequences. To test for efficient splicing, a chimeric vector (pcDNA3.1 CFTR-Donor/Acceptor) is introduced to Xenopus oocytes by nuclear injection of the vector, followed by two electrode voltage (TEV) clamp recording functional analysis of CFTR (Jiang et al., 1998). mRNA transcripts are also analyzed for correct splicing following transfection of pcDNA3.1CFTR-Donor/Acceptor into MDCK cells. Polarized airway epithelial cells grown at the air-liquid interface are co-infected with the donor and acceptor CFTR AAV vectors CFTR gene expression in these cells is then monitored by both immunofluorescent localization and functional analysis of short circuit currents (Smith et al., 1992; Smith et al., 1990). Hirt analyses of episomal AAV species are used to correlate the efficacy and persistence of CFTR gene expression with the formation of AAV circular intermediates.

References

Afione, S. A., Conrad, C. K., Kearns, W. G., Chunduru, S., Adams, R., Reynolds, T. C., Guggino, W. B., Cotting, G. R., Carter, B. J., and Flotte, T. R. In vivo model of adeno-associated virus vector persistence and rescue. *J. Virol.* 70, 3235–3241 (1996).

Ali, R. R. et al. Gene transfer into the mouse retina mediated by an adeno-associated viral vector. *Hum Mol Genet* 5, 591–594 (1996).

Bennett, J., Duan, D., Engelhardt, J. F., and Maguire, A. M. Real-time noninvasive in vivo assessment of adenoassociated virus-mediated retinal transduction. *Invest. Ophthalmol. Vis. Sci.* 38, 2857–2963 (1997).

Berns, K. I. Parvovirus replication. *Microbiol Rev* 54, 316–329 (1990).

Berns, K. I. & Giraud, C. Biology of adeno-associated virus. *Curr. Top. Microbiol Immunol.* 218, 1–23 (1996).

Cheung, A. K., Hoggan, M. D., Hauswirth, W. W. & Berns, K. I. Integration of the adeno-associated virus genome into cellular DNA in latently infected human Detroit 6 cells. *J. Virol.* 33, 739–748 (1980).

Clark, K. R., Sferra, T. J. & Johnson, P. R. Recombinant adeno-associated viral vectors mediate long-term transgene expression in muscle. *Hum. Gene Ther.* 8, 659–669 (1997).

Conrad, C. K., Allen, S. S., Afione, S. A., Reynolds, T. C., Beck, S. E., Fee-Maki, M., Barrazza-Ortiz, X., Adams, R., Askin, F. B., Carter, B. J., Guggino, W. B., and Flotte, T. R. Safety of single-dose administration of an adeno-associated virus (AAV)-CFTR vector in the primate lung. *Gene Ther.* 3, 658–668 (1996).

Duan, D., Fisher, K. J., Burda, J. F. & Engelhardt, J. F. Structural and functional heterogeneity of integrated recombinant AAV genomes. *Virus Res* 48, 41–56 (1997).

Duan, D. et al. Circular Intermediates of Recombinant Adeno-Associated Virus have Defined Structural Characteristics Responsible for Long Term Episomal Persistence In Muscle. *J. Virol.* 72, 8568–8577 (1998b).

Duan, D., Yue, Y., Yan, Z., McCray, P. B. & Engelhardt, J. F. Polarity influences the efficiency of recombinant adeno-associated virus infection in differentiated airway epithelia. *Human Gene Therapy* 9, 2761–2776 (1998a).

Engelhardt, J. F., Schlossberg, H., Yankaskas, J. R. & Dudus, L. Progenitor cells of the adult human airway involved in submucosal gland development. *Development* 121, 2031–2046 (1995).

Ferrari, F. K., Samulski, T., Shenk, T., and Samulski, R. J. Second-strand synthesis is a rate-limiting step for efficient transduction by recombinant adeno-associated virus vectors. *J. Virol* 70, 3227–3234 (1996).

Fisher, K. J., Gao, G. P., Weitzman, M. D., DeMatteo, R., Burda, J. F., and Wilson, J. M. Transduction with recombinant adeno-associated virus for gene threapy is limited by leading-strand synthesis. *J. Virol.* 70, 520–532 (1996).

Fisher, K. J. et al. Recombinant adeno-associated virus for muscle directed gene therapy. *Nat. Med.* 3, 306–312 (1997).

Fisher-Adams, G., Wong, K. K.,Jr., Podsakoff, G., Forman, S. J. & Chattejee, S.
Integration of adeno-associated virus vectors in cd34+ human hematopoietic progenitor cells after transduction. *Blood* 88, 492–504 (1996).

Flannery, J. G. et al. Efficient photoreceptor-targeted gene expression in vivo by recombinant adeno-associated virus. *Proc. Natl. Acad. Sci. USA* 84, 6916–6921 (1997).

Flotte, T. R., Afione, S. A. & Zeitlin, P. L. Adeno-associated virus vector gene expression occurs in nondividing cells in the absence of vector DNA integration. *Amer. J. Resp. Cell Mol. Biol.* 11, 517–521 (1994).

Halbert, C. L. et al. Transduction by adeno-associated virus vectors in the rabbit airway: Efficiency, persistence and readministration. *J. Virol.* 71, 5932–5941 (1997).

Herzog, R. W., Hagstrom, J. N., Kung, S. H., Tai, S. J., Wilson, J. M., Fisher, K. J., and High, K. A. Stable gene transfer and expression of human blood coagulation factor IX after intramuscular injection of recombinant adeno-associated virus. *Proc. Natl. Acad. Sci. USA* 94, 5804–5809 (1997).

Hirt, B. Selective extraction of polyoma DNA from infected mouse cell culture. *J. Mol. Biol.* 26, 365–369 (1967).

Hyde, H., Daviesm, A. A., Benso, F. E., West, S. C. Resolution of recombination intermediates by a mammalian activity functionally analogous to *Escherichia coil* RuvC resolvase. *J. Biol. Chem.* 269, 5202–5209 (1994).

Jiang, Q., Mak, D., Devidas, S., Schweibert, E. M., Bragin, A., Zhang, Y., Skach, W. R., Guggino, W. B., Foskett, J. K., and Engelhardt, J. F. Cystic fibrosis transmembrane conductance regulator-associated ATP release is controlled by a chloride sensor. *J. Cell Biol.* 143(3):645–57.

Kaplitt, M. G., Leone, P., Samulski, R. J., Xiao, X., Pfaff, D. W., O'Malley, K. L., and During, M. J. Long-term gene expression and phenotypic correction using adeno-associated virus vectors in the mammalian brain. *Nat. Genet.* 8, 148–154 (1994).

Kearns, W. G. et al. Recombinant adeno-associated virus (AAV-CFTR) vectors do not integrate in a site-specific fashion in an immortalized epithelial cell line. *Gene Ther.* 3, 748–755 (1996).

Kessler, P. D. et al. Gene delivery to skeletal muscle results in sustained expression and systemic delivery of a therapeutic protein. *Proc. Natl. Acad. Sci. USA* 93, 14082–14087 (1996).

Koeberl, D. D., Alexander, I. A., Halbert, C. L., Russell, D. W. & Miller, A. D. Persistent expression of human clotting factor IX from mouse liver after intravenous injection of adeno-associated virus vectors. *Proc. Natl. Acad. Sci.* USA 94, 1426–1431 (1997).

Kotin, R. M., Linden, R. M. & Bems, K. I. Characterization of a preferred site on human chromosome 19q for integration of adeno-associated virus DNA by non-homologous recombination. *Embo J.* 11, 5071–5078 (1992).

Lee, J., Voziyanov, Y., Pathania, S., Jayaram, M. Resolution of recombination intermediates by a mammalian activity functionally analogous to *Escherichia coli* RuvC resolvase. Structural alterations and conformational dynamics in Holliday junctions induced by binding of a site-specific recombinase. *Mol. Cell* 1, 483–493 (1998).

Linden, R. M., Ward, P., Giraud, C., Winocour, E., and Bems, K. I. Resolution of recombination intermediates by a mammalian activity functionally analogous to *Escherichia coli* RuvC resolvase. Site-specific integration by adeno-associated virus. *Proc. Natl. Acad. Sci. USA* 93, 11288–11294 (1996a).

Linden, R. M., Winocour, E. & Bems, K. I. The recombination signals for adeno-associated virus site specific integration. *Proc Natl. Acad. Sci. USA* 93, 7966–7972 (1996b).

Lobel, L. I., Murphy, J. E., and Goff, S. P. Resolution of recombination intermediates by a mammalian activity functionally analogous to *Escherichia coli* RuvC resolvase. The palindromic LTR-LTR junction of Moloney murine leukemia virus is not an efficient substrate for proviral integration. *J. Virol.* 63, 2629–2637 (1989).

McLaughlin, S. K., Collis, P., Hermonat, P. L. & Muzyczka, N. Adeno-associated virus general transduction vectors: Analysis of proviral structures. *J. Virol.* 62, 1963–1973 (1988).

Miao, C. H. et al. The kinetics of rAAV integration in the liver [letter]. *Nat Genet* 19, 13–15 (1998).

Muzyczka, N. Use of adeno-associated virus as a general transduction vector for mammalian cells. *Curr. Top. Microbiol. Immunol.* 158, 97–129 (1992).

Panganiban, A. T. Retroviral DNA integration. *Cell* 42, 5–6 (1985).

Phillip, R. et al. Efficient and sustained gene expression in primary T lymphocytes and primary and cultured tumor cells mediated by adeno-associated virus plasmid DNA complexed to cationic liposomes. *Mol. Cell. Biol.* 14, 2411–2418 (1994).

Ponnazhagan, S., Erikson, D., Kearns, W. G., Zhou, S. Z., Nahreini, P., Wang, X. S., and Srivastava, A. Lack of site-specific integration of the recombinant adeno-associated virus 2 genomes in human cells. *Hum. Gene Ther.* 8, 275–284 (1997).

Qing, K., Khuntirat B., Mah C., Kube D. M., Wang X., Ponnazhagan, S., Zhou S., Dwarki V. J., Yoder M. C., Srivastava, A. Adeno-associated virus type 2-mediated gene transfer: correlation of tyrosine phosphorylation of the cellular single-stranded D sequence-binding protein with transgene expression in human cells in vitro and murine tissues in vivo. *J. Virol.* 72, 1593–1599 (1998).

Qing, K. et al Role of tyrosine phosphorylation of a cellular protein in adeno-associated virus 2-mediated transgene expression. *Proc Natl Acad Sci U S A* 94, 10879–10884 (1997).

Qing, K. et al. Adeno-associated virus type 2-mediated gene transfer: correlation of tyrosine phosphorylation of the cellular single-stranded D sequence-binding protein with transgene expression in human cells in vitro and murine tissues in vivo. *J. Virol* 72, 1593–1599 (1998).

Qing, K. et al. Human fibroblast growth factor receptor 1 is a co-receptor for infection by adeno-associated virus 2. *Nat Med* 5, 71–77 (1999).

Reich, N. C., Sarnow, P., Duprey, E., and Levine, A. J. (1983). Monoclonal antibodies which recognize native and denatured forms of the adenovirus DNA-binding protein. *Virology* 128, 480–484.

Rutledge, E. A. & Russell, D. W. Adeno-associated virus vector integration junctions. *J. Virol.* 71, 8429–8436 (1997).

Samulski, R. J., Chang, L. S. & Shenk, T. A recombinant plasmid from which an infectious adeno-associated virus genome can be excised in vitro and its use to study viral replication. *J. Virol.* 61, 3096–3101 (1987).

Samulski, R. J., Chang, L. S. & Shenk, T. Helper-free stocks of recombinant adeno-associated viruses: normal integration does not require viral gene expression. *J. Virol.* 63, 3822–3828 (1989).

Samulski, R. J. Adeno-associated virus: integration at a specific chromosomal locus. *Curr. Opin. Genet. Dev.* 3, 74–80 (1993).

Smith J. J., et al. cAMP stimulates bicarbonate secretion across normal, but not cystic fibrosis airway epithelia. *J. Clin .Invest.* 89(4):1148–53 (1992).

Smith J. J., et al. Bradykinin stimulates airway epithelial Cl-secretion via two second messenger pathways. *Am. J. Physiol.* 258:L369–77 (1990).

Summerford, C. & Samulski, R. J. Membrane-associated heparan sulfate proteoglycan is a receptor for adeno-associated virus type 2 virions. *J. Virol.* 72, 1438–1445 (1998).

Summerford, C., Bartlett, J. S. & Samulski, R. J. AlphaV-beta5 integrin: a co-receptor for adeno-associated virus type 2 infection. *Nat Med* 5, 78–82 (1999).

Synder, R. O., MIAO, C. H., Patijn, G. A., Spratt, S. K., Danos, O., Nagy, D., Gown, A. M., Winther, B., Meuse, L., Cohen, L. K., Thompson, A. R., Kay, M. A. Persistent and therapeutic concentration of human factor IX in mice after hepatic gene transfer of recombinant AAV vectors. *Nat. Genet.* 16, 270–276 (1997).

Varmus, H. E. Form and function of retroviral proviruses. *Science* 216, 812–820 (1982).

Vieweg, J. et al., Efficient gene transfer with adeno-associated virus-based plasmids complexed to cationic liposomes for gene therapy of human prostate cancer. *Cancer Res.* 55, 2366–2372 (1995).

Vincent-Lacaze, N. et al. Structure of adeno-associated virus vector DNA following transduction of the skeletal muscle *J Virol* 73, 1949–1955 (1999).

Walsh, C. E., Nienhuis, A. W., Samulski, R. J., Brown, M. G., Miller, J. L., Young, N. S., and Liu, J. M. Phenotypic correction of fanconi anemia in human hematopoietic cells with a recombinant adeno-associated virus vector. *J. Clin. Invest.* 94, 1440–1448 (1994).

Wang X., Ponnazhagan, S., Srivastava, A. Adeno-associated virus type 2 DNA replication in vivo: mutation analyses of the D sequence in viral inverted terminal repeats. *J. Virol.* 71, 3077–3082 (1997).

West, S. C. Processing of recombination intermediates by the RuvABC proteins. *Annu. Rev. Genet.* 31:213–244 (1997).

Westfall, T. D., Kennedy, C. & Sneddon, P. The ecto-ATPase inhibitor ARL 67156 enhances parasympathetic neurotransmission in the guinea-pig urinary bladder. *Eur. J. Pharmacol.* 329, 169–173 (1997).

Wu, P., Phillips, M. I., Bui, J. & Terwilliger, E. F. Adeno-associated virus vector-mediated transgene integration into neurons and other nondividing cell targets. *J. Virol.* 72, 5919–5926 (1998).

Xiao, X., Li, J. & Samulski, R. J. Efficient long-term gene transfer into muscle tissue of immunocompetent mice by adeno-associated virus vector. *J. Virol.* 70, 8098–8108 (1996).

Yang, C. C. et al. Cellular recombination pathways and viral terminal repeat hairpin structures are sufficient for adeno-associated virus integration in vivo and in vitro. *J. Virol.* 71, 9231–9247 (1997).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A composition comprising:
   a first adeno-associated virus vector comprising linked:
   i) a first nucleic acid segment comprising a 5'-inverted terminal repeat of adeno-associated virus;
   ii) a second nucleic acid segment comprising a portion of a gene which includes a transcriptional regulatory region;
   iii) a third nucleic acid segment comprising a splice donor site; and
   iv) a fourth nucleic acid segment comprising a 3'-inverted terminal repeat of adeno-associated virus; and
   b) a second adeno-associated virus vector comprising linked:
   i) a first nucleic acid segment comprising a 5'-inverted terminal repeat of adeno-associated virus;
   ii) a second nucleic acid segment comprising a splice acceptor site;
   iii) a third nucleic acid segment comprising a portion of a gene which together with the nucleic acid segment of a)(ii) comprises a gene comprising an open reading frame which encodes a functional polypeptide; and iv) a fourth nucleic acid segment comprising a 3'-inverted terminal repeat of adeno-associated virus.

2. The composition of claim 1 further comprising a delivery vehicle.

3. The composition of claim 1 wherein the nucleic acid segment of a)ii) comprises a promoter.

4. The composition of claim 1 wherein the nucleic acid segment of a)ii) comprises a enhancer.

5. A method to express a polypeptide in a host cell comprising contacting the host cell with the composition of claim 1 so as to express the functional polypeptide.

6. A method to express a polypeptide in a host cell, comprising:
   contacting a host cell comprising a first adeno-associated virus vector comprising linked:
   a) i) a first nucleic acid segment comprising a 5'-inverted terminal repeat of adeno-associated virus;
      ii) a second nucleic acid segment comprising a portion of a gene which includes a transcriptional regulatory region;
      iii) a third nucleic acid segment comprising a splice donor site; and
      iv) a fourth nucleic acid segment comprising a 3'-inverted terminal repeat of adeno-associated virus;
   with a second adeno-associated virus vector comprising linked:
   b) i) a first nucleic acid segment comprising a 5'-inverted terminal repeat of adeno-associated virus;
      ii) a second nucleic acid segment comprising a splice acceptor site;
      iii) a third nucleic acid segment comprising a portion of a gene which together with the nucleic acid segment of a)ii) comprises a gene comprising an open reading frame which encodes a functional polypeptide; and
      iv) a fourth nucleic acid segment comprising a 3'-inverted terminal repeat of adeno-associated virus;
   so as to yield a host cell which expresses the functional polypeptide.

7. A method to express a polypeptide in a host cell, comprising:
   contacting a host cell comprising a first adeno-associated virus vector comprising linked:
   a) i) a first nucleic acid segment comprising a 5'-inverted terminal repeat of adeno-associated virus;
      ii) a second nucleic acid segment comprising a splice acceptor site;
      iii) a third nucleic acid segment comprising a portion of a gene; and
      iv) a fourth nucleic acid segment comprising a 3'-inverted terminal repeat of adeno-associated virus;
   with a second adeno-associated virus vector comprising linked:
   b) i) a first nucleic acid segment comprising a 5'-inverted terminal repeat of adeno-associated virus;
      ii) a second nucleic acid segment comprising a portion of a gene which includes a transcriptional regulatory region and which together with the nucleic acid segment of a)iii) comprises a gene comprising an open reading frame which encodes a functional polypeptide;
      iii) a third nucleic acid segment comprising a splice donor site; and
      iv) a fourth nucleic acid segment comprising a 3'-inverted terminal repeat of adeno-associated virus;
   so as to yield a host cell which expresses the functional polypeptide.

8. A method to express a polypeptide in a host cell, comprising:
   contacting a host cell with a first adeno-associated virus vector and a second adeno-associated virus vector, wherein the first adeno-associated virus vector comprises linked:
   a) i) a first nucleic acid segment comprising a 5'-inverted terminal repeat of adeno-associated virus;
      ii) a second nucleic acid segment comprising a portion of a gene which includes a transcriptional regulatory region;
      iii) a third nucleic acid segment comprising a splice donor site; and
      iv) a fourth nucleic acid segment comprising a 3'-inverted terminal repeat of adeno-associated virus;
   wherein the second adeno-associated virus vector comprises linked:
   b) i) a first nucleic acid segment comprising a 5'-inverted terminal repeat of adeno-associated virus;
      ii) a second nucleic acid segment comprising a splice acceptor site;
      iii) a third nucleic acid segment comprising a portion of a gene which together with the nucleic acid segment of a)ii) comprises a gene comprising an open reading frame which encodes a functional polypeptide; and
      iv) a fourth nucleic acid segment comprising a 3'-inverted terminal repeat of adeno-associated virus;
   so as to yield a host cell which expresses the functional polypeptide.

9. The method of claim 6 or 8 wherein the nucleic acid segment of a)ii) comprises a promoter.

10. The method of claim 6 or 8 wherein the nucleic acid segment of a)ii) comprises an enhancer.

11. The method of claim 7 wherein the nucleic acid segment of b)ii) comprises a promoter.

12. The method of claim 7 wherein the nucleic acid segment of b)ii) comprises an enhancer.

13. The method of claim 5, 6, 7 or 8 wherein the host cell is a muscle cell, brain cell, retinal cell, liver cell, lung cell or hematopoietic cell.

14. The method of claim 5, 6, 7 or 8 wherein the polypeptide is the cystic fibrosis transmembrane receptor, polypeptide, β-globin, γ-globin, tyrosine hydroxylase, glucocerebrosidase, arylsulfatase A, factor VIII, dystrophin, or erythropoietin.

15. The method of claim 5, 6, 7 or 8 wherein the host cell is a mammalian cell.

16. The method of claim 15 wherein the host cell is a muscle cell, brain cell, retinal cell, liver cell, lung cell or hematopoietic cell.

17. The method of claim 5, 6, 7 or 8 wherein the host cell is selected from the group consisting of an avian cell, a bovine cell, a swine cell, an equine cell, an ovine cell, a canine cell, a feline cell, an amphibian cell, a reptilian cell and a fish cell.

18. The method of claim 17 wherein the host cell is a muscle cell, brain cell, retinal cell, liver cell, lung cell or hematopoietic cell.

19. The method of claim 5, 6, 7 or 8 wherein the vectors comprise DNA.

20. A first composition comprising:
   a first adeno-associated virus vector comprising linked:
   a) i) a first nucleic acid segment comprising a s'-inverted terminal repeat of adeno-associated virus;
      ii) a second nucleic acid segment comprising a portion of a gene which includes a transcriptional regulatory region;

iii) a third nucleic acid segment comprising a splice donor site; and iv) a fourth nucleic acid segment comprising a 3'-inverted terminal repeat of adeno-associated virus;

and a second composition comprising a second adeno-associated virus vector comprising linked:

b) i) a first nucleic acid segment comprising a 5'-inverted terminal repeat of adeno-associated virus;

ii) a second nucleic acid segment comprising a splice acceptor site;

iii) a third nucleic acid segment comprising a portion of a gene which together with the nucleic acid segment of a)(ii) comprises a gene comprising an open reading frame which encodes a functional polypeptide;

iv) a fourth nucleic acid segment comprising a 3'-inverted terminal repeat of adeno-associated virus;

which vectors in a host cell yield a RNA transcript which comprises sequences from the first adeno-associated virus vector linked to sequences from the second adeno-associated virus vector, which sequences are positioned so that the splice donor site is 5' to the splice acceptor site, and which transcript is spliced to a mRNA which encodes the functional protein.

21. A first composition comprising:

a first adeno-associated virus vector comprising linked:

a) i) a first nucleic acid segment comprising a 5'-inverted terminal repeat of adeno-associated virus;

ii) a second nucleic acid segment comprising a splice acceptor site;

iii) a third nucleic acid segment comprising a portion of a gene; and iv) a fourth nucleic acid segment comprising a 3'-inverted terminal repeat of adeno-associated virus;

and a second composition comprising a second adeno-associated virus vector comprising linked:

b) i) a first nucleic acid segment comprising a 5'-inverted terminal repeat of adeno-associated virus;

ii) a second nucleic acid segment comprising a portion of a gene which together with the nucleic acid segment of a)ii) comprises a gene comprising an open reading frame which encodes a functional polypetide, wherein the portion of the gene of b)ii) includes a transcriptional regulatory region;

iii) a third nucleic acid segment comprising a splice donor site;

iv) a fourth nucleic acid segment comprising a 3'-inverted terminal repeat of adeno-associated virus;

which vectors in a host cell yield a RNA transcript which comprises sequences from the first adeno-associated virus vector linked to sequences from the second adeno-associated virus vector, which sequences are positioned so that the splice donor site is 5' to the splice acceptor site, and which transcript is spliced to a mRNA which encodes the functional protein.

\* \* \* \* \*

UNITED STATES PATENT AND TRADEMARK OFFICE
CERTIFICATE OF CORRECTION

PATENT NO. : 6,897,045 B2
DATED : May 24, 2005
INVENTOR(S) : Engelhardt et al.

It is certified that error appears in the above-identified patent and that said Letters Patent is hereby corrected as shown below:

Column 6,
Line 41, delete "concataniers" and insert -- concatamers --, therefor.
Line 42, delete "AseI" and insert -- AseI --, therefor.

Column 9,
Line 29, delete "($Rf_m$.)" and insert -- ($Rf_m$) --, therefor.

Column 11,
Line 60, delete "filly" and insert -- fully --, therefor.

Column 12,
Line 14, delete "AseI" and insert -- AseI --, therefor.

Column 21,
Line 33, delete "(hydrogel)" and insert -- (hydro-gel) --, therefor.

Column 32,
Table 1, line 36, delete "ligased$^d$" and insert -- ligase$^d$ --, therefor.

Column 43,
Line 16, delete "MRNA" and insert -- mRNA --, therefor.

Column 44,
Line 6, delete "byDuan" and insert -- by Duan --, therefor.

Column 48,
Line 1, delete "concatamners" and insert -- concatamers --, therefor.
Line 42, delete "pcDNA3.1 CFTR" and insert -- pcDNA3.1CFTR --, therefor.

Column 49,
Line 48, delete "Chattejee" and insert -- Chatterjee --, therefor.

Column 50,
Line 5, delete "coil" and insert -- coli --, therefor.
Lines 30, 42 and 47, delete "Bems" and insert -- Berns --.

Column 52,
Line 46, insert -- a) -- before "a first".

UNITED STATES PATENT AND TRADEMARK OFFICE
CERTIFICATE OF CORRECTION

PATENT NO. : 6,897,045 B2
DATED : May 24, 2005
INVENTOR(S) : Engelhardt et al.

It is certified that error appears in the above-identified patent and that said Letters Patent is hereby corrected as shown below:

Column 53,
Line 8, delete "a" and insert -- an --, therefor.

Column 55,
Line 13, delete "(ii)" and insert -- ii) --, therefor.

Column 56,
Line 13, delete "ii)" and insert -- iii) --, therefor.
Line 15, delete "polypetide" and insert -- polypeptide --, therefor.

Signed and Sealed this

Twenty-third Day of August, 2005

JON W. DUDAS
*Director of the United States Patent and Trademark Office*